(12) United States Patent
Wang et al.

(10) Patent No.: US 12,365,685 B2
(45) Date of Patent: Jul. 22, 2025

(54) SUBSTITUTED FUSED AROMATIC RING DERIVATIVE, COMPOSITION AND USE THEREOF

(71) Applicant: Shenzhen TargetRx, Inc., Guangdong (CN)

(72) Inventors: Yihan Wang, Guangdong (CN); Qingfeng Xing, Guangdong (CN); Yixin Ai, Shenzhen (CN)

(73) Assignee: Shenzhen TargetRx, Inc., Guangdong (CN)

( * ) Notice: Subject to any disclaimer, the term of this patent is extended or adjusted under 35 U.S.C. 154(b) by 927 days.

(21) Appl. No.: 17/426,373

(22) PCT Filed: Feb. 13, 2020

(86) PCT No.: PCT/CN2020/074983
§ 371 (c)(1),
(2) Date: Jul. 28, 2021

(87) PCT Pub. No.: WO2020/168963
PCT Pub. Date: Aug. 27, 2020

(65) Prior Publication Data
US 2022/0098204 A1 Mar. 31, 2022

(30) Foreign Application Priority Data
Feb. 18, 2019 (CN) .......................... 201910127767.3

(51) Int. Cl.
C07D 487/04 (2006.01)
A61P 35/00 (2006.01)
A61P 35/02 (2006.01)
C07D 471/04 (2006.01)

(52) U.S. Cl.
CPC ......... C07D 487/04 (2013.01); C07D 471/04 (2013.01)

(58) Field of Classification Search
CPC ..... C07D 487/04; C07D 471/04; A61P 35/00; A61P 35/02
See application file for complete search history.

(56) References Cited

U.S. PATENT DOCUMENTS

2022/0380375 A1* 12/2022 Wang ...................... A61P 35/00

FOREIGN PATENT DOCUMENTS

| CN | 101128461 A | 2/2008 |
|---|---|---|
| CN | 102266341 A | 12/2011 |
| CN | 104513252 A | 4/2015 |
| CN | 108948002 A | 12/2018 |
| CN | 109232440 A | 1/2019 |
| EP | 1 382 603 A1 | 1/2004 |
| JP | 2008-531574 A | 8/2008 |
| JP | 2008-532926 A | 8/2008 |
| JP | 2008-538356 A | 10/2008 |
| JP | 2014-525464 A | 9/2014 |
| JP | 2017-519818 A | 7/2017 |
| WO | WO 2004/078756 A2 | 9/2004 |
| WO | WO 2006/091671 A1 | 8/2006 |
| WO | WO 2006/108640 A1 | 10/2006 |
| WO | WO 2007/112093 A2 | 10/2007 |
| WO | WO 2009/014620 A1 | 1/2009 |
| WO | WO 2010/017047 A1 | 2/2010 |
| WO | WO 2015/187818 A1 | 12/2015 |
| WO | WO 2018/035061 A1 | 2/2018 |
| WO | WO 2021/057877 A1 | 4/2021 |

OTHER PUBLICATIONS

International Search Report and Written Opinion for Application No. PCT/CN2020/074983, mailed May 9, 2020.
Office Action for Chinese Application No. 202010089809.1, mailed Apr. 6, 2021.
No Author Listed, RN908329-69-1 etc. Entered STN: Feb. 20, 2018. 107 pages.
No Author Listed, RN2309151-24-2 etc. Entered STN: May 16, 2019. 19 pages.
No Author Listed, RN1347947-26-5 etc. Entered STN: Dec. 4, 2011. 1 page.
Berge et al., Pharmaceutical Salts. J Pharm Sci. Jan. 1977;66(1):1-19. doi: 10.1002/jps.2600660104.
Chen et al., Developing and applying a gene functional association network for anti-angiogenic kinase inhibitor activity assessment in an angiogenesis co-culture model. BMC Genomics. Jun. 2, 2008;9:264. doi: 10.1186/1471-2164-9-264.
Fleisher et al., Improved oral drug delivery: solubility limitations overcome by the use of prodrugs. Advanced Drug Delivery Reviews. 1996; 19: 115-130.
Extended European Search Report for Application No. 20759406.0, mailed Feb. 11, 2022.

(Continued)

*Primary Examiner* — Sun Jae Yoo
(74) *Attorney, Agent, or Firm* — Wolf, Greenfield & Sacks, P.C.

(57) ABSTRACT

Provided are a substituted fused aromatic ring derivative, a composition containing the compound, and a use thereof. The substituted fused aromatic ring derivative is a compound represented by formula (I) or a tautomer, stereoisomer, prodrug, crystal form, pharmaceutically acceptable salt, hydrate or solvate thereof. The compound and the composition can be used to treat various protein tyrosine kinase-mediated diseases or disorders.

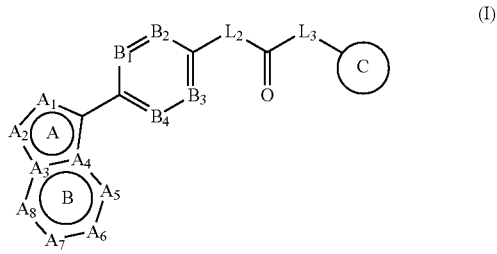

(I)

12 Claims, No Drawings

(56) References Cited

OTHER PUBLICATIONS

Japanese Office Action for Application No. 2021-548215, mailed Nov. 15, 2022.
EP20759406.0, Feb. 11, 2022, Extended European Search Report.
CN202010089809.1, Apr. 6, 2021, Chinese Office Action and English translation thereof.
PCT/CN2020/074983, May 9, 2020, International Search Report and Written Opinion.

* cited by examiner

SUBSTITUTED FUSED AROMATIC RING DERIVATIVE, COMPOSITION AND USE THEREOF

CROSS REFERENCE TO RELATED APPLICATIONS

This application is a national application of PCT/CN2020/074983, filed on Feb. 13, 2020, which claims the priority of Chinese Patent Application No. 201910127767.3 filed on Feb. 18, 2019, the entire content of which is incorporated by reference as a part of this application.

FIELD OF THE INVENTION

The present disclosure belongs to the technical filed of medicine, and in particular relates to a substituted aromatic fused ring derivative with an inhibitory action on a protein tyrosine kinase, a pharmaceutical composition containing the same, and a preparation method and use thereof.

BACKGROUND OF THE INVENTION

Protein kinases (PKs) are enzymes that catalyze the phosphorylation of specific serine, threonine or tyrosine in cellular proteins. Post-translational modifications of these substrate proteins act as molecular switches that play key roles in various biological processes, such as the control of cell growth, metabolism, tumor microenvironment (e.g., VEGFR), differentiation, and apoptosis. Abnormal, excessive or more generally inappropriate PK activity has been observed in several disease states, including malignant proliferative diseases, such as functional mutations in medullary thyroid carcinoma (MTC) and other human malignant tumors, ITD (Internal tandem duplication)-mutations in FLT3 of acute myeloid leukemia (AML), c-Kit mutations in gastrointestinal stromal tumor (GIST), and RET obtained from BCR-ABL rearrangement in chronic myelogenous leukemia (CML). In addition, the activation and/or overexpression of tyrosine kinases (e.g., TrkA, TrkB, TrkC, and RET) cause cancer. Many tyrosine kinases are homologous to each other: inhibiting one tyrosine kinase can also produce a certain inhibitory activity on other tyrosine kinases. For example, imatinib has been used as a therapeutic agent not only for CML patients (based on the inhibition of BCR-ABL kinases), but also for GIST cancer patients (based on the inhibition of c-Kit kinase). Several targets for cancer therapy and the problems involved are briefly described below.

RET

RET (Rearranged during transfection) belongs to the family of receptor tyrosine kinase proteins and is a cell surface molecule that signaling cell growth and differentiation. RET gene mutation or RET gene fusion has been identified as a driving factor for certain cancers. The incidence of RET gene fusion in non-small cell lung cancer is about 2%, and the incidence of RET gene fusion in papillary thyroid cancers (PTCs) is 10%~20%. The most common fusion partners include KIF5B, TRIM33, CCDC6 and NCOA4. The incidence of RET gene mutation in medullary thyroid cancers (MTCs) is about 60%, and the most common mutation site is M918T. RET inhibitor resistance mutations include, but are not limited to, amino acid position 804 (V804M, V804L, V804E), amino acid position 805 (E805K), and amino acid position 806 (Y806C, Y806E).

TRK

Trk (tropomyosin-related kinase) is high affinity receptor tyrosine kinase activated by a group of soluble growth factors called neurotrophin (NT). Trk receptor family has three members, namely TrkA, TrkB and TrkC. The neurotrophin includes (1) nerve growth factor (NGF) which can activate TrkA, (2) brain-derived neurotrophic factor (BDNF) and NT4/5 which can activate TrkB, and (3) NT3 which can activate TrkC. Trk is widely expressed in neuronal tissues and is involved in the maintenance, signaling and survival of neuronal cells. Literatures also show that the overexpression, activation, amplification and/or mutation of Trk is associated with many cancers including neuroblastoma, ovarian cancer, breast cancer, prostate cancer, pancreatic cancer, multiple myeloma, astrocytoma and medulloblastoma, glioma, melanoma, thyroid cancer, pancreatic cancer, large cell neuroendocrine tumor and colorectal cancer. In addition, inhibitors of Trk/neurotrophin pathway have been shown to be effective in a variety of preclinical animal models for the treatment of pain and inflammatory diseases.

FLT3

FLT3 (FMS-like tyrosine kinase 3) belongs to the kinase protein of the class III receptor tyrosine kinase family. FLT3 is a receptor tyrosine kinase that plays a role in regulating production of normal hematopoietic cells and is overexpressed in leukemic embryonic cells. Mutations in the FLT3 gene are characterized by 30% of AML cases. Internal tandem duplication (ITD) mutation (accounting for about 23% of AML cases) in FLT3 is associated with a particularly poor prognosis. The problems involved in the prognosis of FLT3/D835 point mutations found in about 7% of cases in diagnosis have not yet been established. It may be advantageous to inhibit FLT3 and mutations thereof.

c-Kit c-KIT (also known as CD117) is a type of transmembrane receptor protein with tyrosine kinase activity encoded by the retroviral proto-oncogene c-kit. The c-KIT kinase consists of an extracellular domain, a transmembrane domain and an intracellular domain. The ligand of c-KIT is a stem cell factor (SCF), which binds to the extracellular domain of c-KIT to induce receptor dimerization and activate downstream signal transduction pathways. Mutations in c-KIT usually occur in the DNA (exon 11) that encodes the domain of juxtamembrane regions. They also occur in exons 7, 8, 9, 13, 14, 17, and 18 at a lower frequency. The mutations make the function of c-KIT independent of activation by SCF, resulting in high cell division rate and possible genomic instability. The mutations of c-KIT have been involved in the pathogenesis of several diseases and conditions, including systemic mastocytosis (SM), gastrointestinal stromal tumor (GIST), acute myeloid (myelocytic) leukemia (AML), melanoma and seminoma. Thus, there is a need to develop therapeutic agents inhibiting c-KIT, and in particular drugs inhibiting mutant c-KIT.

PDGFR

PDGFR (Platelet Derived Growth Factor Receptor) is a cell surface tyrosine kinase receptor that is a member of the platelet-derived growth factor (PDGF) family. PDGF subunits PDGFα and PDGFβ are vital factors in regulation of cell proliferation, cell differentiation, cell growth, development, and various diseases including cancers. D842V mutation of PDGFRα has been found in different subsets of gastrointestinal stromal tumor (GIST), usually from the stomach. The D842V mutation is known to be associated with resistance to tyrosine kinase inhibitors.

VEGFR

VEGFR (vascular endothelial growth factor) is a vital signal transduction protein involved in angiogenesis and vasculogenesis. As the name implies, the activity of VEGFR is mainly limited to vascular endothelial cells, although VEGFR also has an effect on a limited number of other cell types. In vitro, it has been confirmed that the VEGFR stimulates mitogenesis and migration of endothelial cells. VEGFR also promotes microvascular permeability, and is sometimes referred to as a vascular permeability factor. The VEGFR kinase has been used as a target for solid tumors, such as highly vascularized malignant tumors such as kidney cancer, glioblastoma, and liver cancer.

SUMMARY OF THE INVENTION

The present disclosure provides a novel aromatic fused ring derivative, a composition containing the compound, and use thereof. The aromatic fused ring derivative has better inhibitory activity and selectivity for some wild-type and mutant RET, KIF5B-RET, CCDC6-RET, TrkA, TrkB, TrkC, FLT3, c-Kit, PDGFR, and VEGFR kinases, and has better pharmacodynamic and/or pharmacokinetic properties. The aromatic fused ring derivative can treat diseases mediated by protein kinases.

In this regard, the following technical solutions are used in the present disclosure:

In one aspect, the present disclosure related to a compound of formula (I):

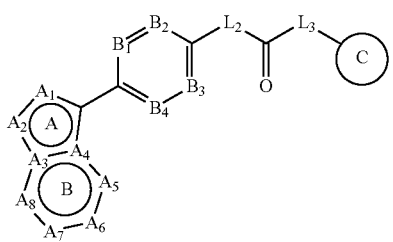

(I)

wherein
ring A and ring B form an aromatic fused ring;
$A_1$ is selected from N atom and C atom, which are optionally substituted with $R_1$;
$A_2$ is selected from N atom and C atom, which are optionally substituted with $R_2$;
wherein each instance of $R_1$ and $R_2$ is each independently selected from H, D, halogen, —CN, $C_{1-6}$ alkyl, $C_{1-6}$ haloalkyl, $C_{3-7}$ cycloalkyl, $C_{1-6}$ alkoxyl, $C_{1-6}$ haloalkoxyl, and —O$C_{3-7}$ cycloalkyl; wherein the above groups are optionally substituted with one or more D, until fully deuterated;
$A_3$ and $A_4$ are each independently selected from C atom and N atom;
$A_5$ and $A_6$ are each independently selected from N atom and C atom, which are optionally substituted with R;
$A_7$ and $A_8$ are each independently selected from N atom and C atom, which are optionally substituted with R';
wherein R and R' are each independently selected from H, D, halogen, —CN, $C_{1-6}$ alkyl, $C_{1-6}$ haloalkyl, $C_{3-7}$ cycloalkyl, $C_{1-6}$ alkoxyl, $C_{1-6}$ haloalkoxyl, —O$C_{3-7}$ cycloalkyl, and -$L_1$-$R_a$; wherein the above groups are optionally substituted with one or more D, until fully deuterated;
wherein $L_1$ is selected from bond, O, and NH; $R_a$ is selected from phenyl, and 5- to 6-membered heteroaryl containing 1-3 heteroatoms selected from N, O and S, wherein the groups are optionally substituted with one or more $R_b$;

$B_1$, $B_2$, $B_3$ and $B_4$ are each independently selected from CR* and N;
wherein each instance of R* is each independently selected from H, D, halogen, —CN, —$R_c$, —C(O)$R_c$, —C(O)O$R_c$, —C(O)N$R_cR_c$, —N$R_cR_d$, —N$R_c$C(O)$R_c$, —N$R_c$C(O)O$R_c$, —N$R_c$C(O)N$R_cR_d$, —O$R_c$, —OC(O)$R_c$, —OC(O)O$R_c$, and —OC(O)N$R_cR_d$;
$L_2$ and $L_3$ are each independently selected from bond, NH, $CH_2$, CHD and $CD_2$;
ring C is selected from phenyl, and 5- to 6-membered heteroaryl containing 1-3 heteroatoms selected from N, O and S, wherein the groups are optionally substituted with one or more $R_{b'}$;
wherein each instance of $R_b$ and $R_{b'}$ is each independently selected from H, D, —OH, —$NH_2$, halogen, —CN, —$R_c$, —C(O)$R_c$, —C(O)O$R_c$, —C(O)N$R_cR_d$, —N$R_cR_d$, —N$R_c$C(O)$R_c$, —N$R_c$C(O)O$R_c$, —N$R_c$C(O)N$R_cR_d$, —O$R_c$, —OC(O)$R_c$, —OC(O)O$R_c$, and —OC(O)N$R_cR_d$, or two $R_b$ groups or two $R_{b'}$ groups attached to the same atom or adjacent atoms can together form $C_{3-7}$ cycloalkyl, 3- to 7-membered heterocyclyl, $C_{6-10}$ aryl, or 5- to 10-membered heteroaryl, wherein $C_{3-7}$ cycloalkyl, 3- to 7-membered heterocyclyl, $C_{6-10}$ aryl, and 5- to 10-membered heteroaryl is optionally substituted with one or more $R_e$;
each instance of $R_c$ and $R_d$ is each independently selected from $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl, and 5- to 10-membered heteroaryl, or $R_c$ and $R_d$ together with the N atom to which they are attached form a 3- to 7-membered heterocyclyl, or 5- to 10-membered heteroaryl; wherein the groups are optionally substituted with one or more $R_e$;
each instance of $R_e$ is independently selected from H, D, —OH, —$NH_2$, halogen, —CN, —$R_f$, —C(O)$R_f$, —C(O)O$R_f$, —C(O)N$R_fR_g$, —N$R_fR_g$, —N$R_f$C(O)$R_f$, —N$R_f$C(O)O$R_f$, —N$R_f$C(O)N$R_fR_g$, —O$R_f$, —OC(O)$R_f$, —OC(O)O$R_f$, and —OC(O)N$R_fR_g$, or two $R_e$ groups attached to the same atom or adjacent atoms can together form $C_{3-7}$ cycloalkyl, 3- to 7-membered heterocyclyl, $C_{6-10}$ aryl, or 5- to 10-membered heteroaryl; wherein each group in the definition of $R^e$ is optionally substituted with one or more D, until fully deuterated;
each instance of $R_f$ and $R_g$ is each independently selected from $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl, and 5- to 10-membered heteroaryl, or $R_f$ and $R_g$ together with the N atom to which they are attached form a 3- to 7-membered heterocyclyl, or 5- to 10-membered heteroaryl; wherein each group in the definition of $R_f$ and $R_g$ is optionally substituted with one or more D, until fully deuterated;
or a tautomer, stereoisomer, prodrug, crystal form, pharmaceutically acceptable salt, hydrate or solvate thereof.

In another aspect, the present disclosure provides a pharmaceutical composition, which comprises a compound disclosed herein, or a pharmaceutically acceptable salt, hydrate or solvate thereof, and pharmaceutically acceptable excipient (s). In a specific embodiment, the compound disclosed herein is provided in a therapeutically effective amount. In a specific embodiment, the compound disclosed herein is provided in a prophylactically effective amount.

In another aspect, the present disclosure provides use of a compound disclosed herein, or a pharmaceutically acceptable salt, hydrate or solvate thereof, or a pharmaceutical composition disclosed herein in the manufacture of a medicament for the treatment of diseases mediated by protein kinases.

In another aspect, the present disclosure provides a method of treating diseases, such as diseases mediated by protein kinases, in a subject, comprising administering to the subject a compound disclosed herein, or a pharmaceutically acceptable salt, hydrate or solvate thereof, or a pharmaceutical composition disclosed herein.

In another aspect, the present disclosure provides a compound disclosed herein, or a pharmaceutically acceptable salt, hydrate or solvate thereof, or a pharmaceutical composition disclosed herein, for treating diseases, such as diseases mediated by protein kinases.

In a specific embodiment, the diseases are mediated by at least one of wild-type or mutant RET, KIF5B-RET, CCDC6-RET, Trk, FLT3, c-Kit, PDGFR, or VEGFR kinases. In a specific embodiment, the mutant RET, KIF5B-RET, and CCDC6-RET are selected from V804L, V804M, V804E, M918T, E805K, Y806C, Y806E, C634Y, and C634W. In a specific embodiment, the Trk kinase is selected from Trk A, TrkB, and TrkC; in a specific embodiment, the mutant TrkA is G595R. In a specific embodiment, the mutant FLT3 is selected from F691L, D835Y, D835V, D835H, D835F, D835E, Y842C, Y842D, Y842H, Y842N, and Y842S; in a specific embodiment, the mutant FLT3 is FLT3-ITD mutation. In a specific embodiment, the mutant c-Kit is selected from D816V, D816Y, D816F, D816K, D816A, and D816G. In a specific embodiment, the mutant PDGFR is D842V.

Other objects and advantages of the present disclosure will be apparent to those skilled in the art from the following specific embodiments, examples, and claims.

Definition

Chemical Definition

The definitions of specific functional groups and chemical terms are described in more detail below.

When a range of values is listed, it is intended to encompass each value and sub-range within the range. For example, "$C_{1-6}$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"$C_{1-6}$ alkyl" refers to a linear or branched, saturated hydrocarbon group having 1 to 6 carbon atoms, and is also referred to herein as "lower alkyl". In some embodiments, $C_{1-4}$ alkyl is alternative. Examples of alkyl include, but are not limited to: methyl ($C_1$), ethyl ($C_2$), n-propyl ($C_3$), iso-propyl ($C_3$), n-butyl ($C_4$), t-butyl ($C_4$), sec-butyl ($C_4$), iso-butyl ($C_4$), n-pentyl ($C_5$), 3-pentyl ($C_5$), pentyl ($C_5$), neo-pentyl ($C_5$), 3-methyl-2-butyl ($C_5$), t-pentyl ($C_5$) and n-hexyl ($C_6$). Regardless of whether or not the alkyl group is modified with "substituted", each alkyl group is independently optionally substituted, for example, with 1 to 5 substituents, 1 to 3 substituents or 1 substituent. Appropriate substituents are defined as follows.

"$C_{2-6}$ alkenyl" refers to a linear or branched, hydrocarbon group having 2-6 carbon atoms and one or more carbon-carbon double bonds (e.g., 1, 2, or 3 carbon-carbon double bonds). One or more carbon-carbon double bonds can be internal (e.g., in 2-butenyl) or terminal (e.g., in 1-butenyl). In some embodiments, $C_{2-4}$ alkenyl is alternative. Examples of alkenyl include, but are not limited to: vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. Regardless of whether or not the alkenyl group is modified with "substituted", each alkenyl group is independently optionally substituted, for example, with 1 to 5 substituents, 1 to 3 substituents or 1 substituent. Appropriate substituents are defined as follows.

"$C_{2-6}$ alkynyl" refers to a linear or branched, hydrocarbon group having 2-6 carbon atoms, one or more carbon-carbon triple bonds (e.g., 1, 2 or 3 carbon-carbon triple bonds) and optionally one or more carbon-carbon double bonds (e.g., 1, 2 or 3 carbon-carbon double bonds). In some embodiments, $C_{2-4}$ alkynyl is alternative. In some embodiments, alkynyl does not contain any double bonds. One or more carbon-carbon triple bonds can be internal (e.g., in 2-butynyl) or terminal (e.g., in 1-butynyl). Examples of alkynyl include, but are not limited to: ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), etc. Regardless of whether or not the alkynyl group is modified with "substituted", each alkynyl group is independently optionally substituted, for example, with 1 to 5 substituents, 1 to 3 substituents or 1 substituent. Appropriate substituents are defined as follows.

"$C_{1-6}$ alkoxyl" refers to a —OR group, wherein R is substituted or unsubstituted $C_{1-6}$ alkyl. In some embodiments, $C_{1-4}$ alkoxyl is alternative. Specifically, alkoxyl includes, but is not limited to: methoxy, ethoxy, n-propoxy, iso-propoxy, n-butoxy, t-butoxy, sec-butoxy, n-pentyloxy, n-hexyloxy and 1,2-dimethylbutoxy.

"Halo" or "halogen" refers to fluoro (F), chloro (Cl), bromo (Br) and iodo (I). In some embodiments, the halo group is F, Cl or Br. In some embodiments, the halo group is F or Cl. In some embodiments, the halo group is F.

Therefore, "$C_{1-6}$ haloalkyl" and "$C_{1-6}$ haloalkoxyl" refer to the above "$C_{1-6}$ alkyl" and "$C_{1-6}$ alkoxyl" substituted with one or more halo groups. In some embodiments, $C_{1-4}$ haloalkyl is alternative, and $C_{1-2}$ haloalkyl is yet alternative. In some embodiments, $C_{1-4}$ haloalkoxyl is alternative, and $C_{1-2}$ haloalkoxyl is yet alternative. Examples of haloalkyl include, but are not limited to: —$CF_3$, —$CH_2F$, —$CHF_2$, —$CHFCH_2F$, —$CH_2CHF_2$, —$CF_2CF_3$, —$CCl_3$, —$CH_2Cl$, —$CHCl_2$, 2,2,2-trifluoro-1,1-dimethyl-ethyl, etc. Examples of haloalkoxyl include, but are not limited to: —$OCH_2F$, —$OCHF_2$, —$OCF_3$, etc.

"$C_{3-10}$ cycloalkyl" refers to a non-aromatic cyclic hydrocarbon group having 3-10 ring carbon atoms and zero heteroatoms. In some embodiments, $C_{3-7}$ cycloalkyl is alternative, $C_{3-6}$ cycloalkyl is alternative, and $C_{5-6}$ cycloalkyl is yet alternative. Cycloalkyl also includes a ring system in which the above cycloalkyl ring is fused with one or more aryl or heteroaryl groups, wherein the point of attachment is on the cycloalkyl ring, and in such instances, the number of carbons continue to designate the number of carbons in the cycloalkyl system. Examples of cycloalkyl include, but are not limited to: cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptyl ($C_7$), bicyclo[2.2.2]octyl ($C_8$), cyclononyl ($C_9$), cyclononenyl ($C_9$), cyclodecyl ($C_{10}$), cyclodecenyl ($C_{10}$), octahydro-1H-indenyl ($C_9$), decahydronaphthyl ($C_{10}$), spiro[4.5]decyl ($C_{10}$), etc. Regardless of whether or not the cycloalkyl group is modified with "substituted", each cycloalkyl group is independently optionally substituted, for example, with 1 to 5 substituents, 1 to 3 substituents or 1 substituent. Appropriate substituents are defined as follows.

"3- to 10-membered heterocyclyl" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon. In heterocyclyl groups that contain one or more nitrogen atoms, the point of attachment can be a carbon or nitrogen atom, as valency permits. In some embodiments, 3- to 7-membered heterocyclyl is alternative, and it is a 3- to 7-membered non-aromatic ring system having ring carbon atoms and 1-3 ring heteroatoms. In some embodiments, 3- to 6-membered heterocyclyl is alternative, and it is a 3- to 6-membered non-aromatic ring system having ring carbon atoms and 1-3 ring heteroatoms. 5- to 6-membered heterocyclyl is yet alternative, and it is a 5- to 6-membered non-aromatic ring system having ring carbon atoms and 1-3 ring heteroatoms. "Heterocyclyl" also includes ring systems wherein the heterocyclyl, as defined above, is fused with one or more cycloalkyl, aryl or heteroaryl groups wherein the point of attachment is on the heterocyclyl ring, and in such instances, the number of ring members continues to designate the number of ring members in the heterocyclyl ring system. Regardless of whether or not the heterocyclyl group is modified with "substituted", each heterocyclyl group is independently optionally substituted, for example, with 1 to 5 substituents, 1 to 3 substituents or 1 substituent. Appropriate substituents are defined as follows.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$aryl ring (also referred to herein as a 5,6-bicyclic heterocyclyl) include, without limitation, indolinyl, isoindolinyl, dihydrobenzofuranyl, dihydrobenzothienyl, benzoxazolinonyl, and the like. Exemplary 6-membered heterocyclyl groups fused to a $C_6$aryl ring (also referred to herein as a 6,6-bicyclic heterocyclyl) include, without limitation, tetrahydroquinolinyl, tetrahydroisoquinolinyl, and the like.

"$C_{6-14}$ aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms. In some embodiments, an aryl group has six ring carbon atoms ("$C_6$aryl"; e.g., phenyl). In some embodiments, an aryl group has ten ring carbon atoms ("$C_{10}$aryl"; e.g., naphthyl such as 1-naphthyl and 2-naphthyl). In some embodiments, an aryl group has fourteen ring carbon atoms ("$C_{14}$aryl"; e.g., anthracyl). In some embodiments, $C_{6-10}$ aryl is alternative, and $C_6$aryl is yet alternative. "Aryl" also includes ring systems wherein the aryl ring, as defined above, is fused with one or more cycloalkyl or heterocyclyl groups wherein the point of attachment is on the aryl ring, and in such instances, the number of carbon atoms continues to designate the number of carbon atoms in the aryl ring system. Regardless of whether or not the aryl group is modified with "substituted", each aryl group is independently optionally substituted, for example, with 1 to 5 substituents, 1 to 3 substituents or 1 substituent. Appropriate substituents are defined as follows.

"5- to 10-membered heteroaryl" refers to a radical of a 5- to 10-membered monocyclic or bicyclic 4n+2 aromatic ring system (e.g., having 6 or 10 pi electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more cycloalkyl or heterocyclyl groups wherein the point of attachment is on the heteroaryl ring, and in such instances, the number of carbon atoms continues to designate the number of carbon atoms in the heteroaryl ring system. In some embodiments, 5- to 6-membered heteroaryl is alternative, and it is a 5- to 6-membered monocyclic or bicyclic 4n+2 aromatic ring system having ring carbon atoms and 1-4 ring heteroatoms. Regardless of whether or not the heteroaryl group is modified with "substituted", each heteroaryl group is independently optionally substituted, for example, with 1 to 5 substituents, 1 to 3 substituents or 1 substituent. Appropriate substituents are defined as follows.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Exemplary substituents on carbon atoms include, but are not limited to: halo, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$_{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$_{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, haloalkyl, alkenyl, alkynyl, carbocyclyl, heterocyclyl, aryl and heteroaryl, wherein, each of alkyl, alkenyl, alkynyl, carbocyclyl, heterocyclyl, aryl and heteroaryl is independently substituted with 0, 1, 2, 3, 4 or 5 Rad groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR—, =NNR$^{bb}$S(=O)$_2$R$^{aa}$, =NR$^{bb}$ or =NOR$^{cc}$;

each R$^{aa}$ is independently selected from alkyl, haloalkyl, alkenyl, alkynyl, carbocyclyl, heterocyclyl, aryl and heteroaryl, or two R$^{aa}$ groups are bound to form heterocyclyl or heteroaryl ring, wherein, each of alkyl, alkenyl, alkynyl, carbocyclyl, heterocyclyl, aryl and heteroaryl is independently substituted with 0, 1, 2, 3, 4 or 5 Rad groups;

each R$^{bb}$ is independently selected from: hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$_c$, —SO$_2$OR$^{cc}$, —SOR$^{aa}$, —C(=S)N(R$_c$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, carbocyclyl, heterocyclyl, aryl and heteroaryl, or two R$^{bb}$ groups are bound to form heterocyclyl or heteroaryl ring, wherein, each of alkyl, alkenyl, alkynyl, carbocyclyl, heterocyclyl, aryl and heteroaryl is independently substituted with 0, 1, 2, 3, 4 or 5 Rad groups;

each R$^{cc}$ is independently selected from hydrogen, alkyl, haloalkyl, alkenyl, alkynyl, carbocyclyl, heterocyclyl, aryl and heteroaryl, or two R$^{cc}$ groups are bound to form heterocyclyl or heteroaryl ring, wherein, each of alkyl, alkenyl, alkynyl, carbocyclyl, heterocyclyl, aryl and heteroaryl is independently substituted with 0, 1, 2, 3, 4 or 5 Rad groups;

each Rad is independently selected from: halo, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{cc}$, —OC(=O)R$^{ee}$, —OCO$_2$R$^{ee}$, —C(=O)N(R$^{f}$)$_2$, —OC(=O)N(R$^{ff}$)$_2$, —NR$^{ff}$C(=O)R$^{ee}$, —NR$^{ff}$CO$_2$R$^{ee}$, —NR$_f$C(=O)N(R$^{ff}$)$_2$, —C(=NR$^{ff}$)OR$^{ee}$, —OC(=NR$^{ff}$)R$^{ee}$, —OC(=NR$^{ee}$)OR$^{ee}$, —C(=NR$^{ff}$)N(R$^{ff}$)$_2$, —OC(=NR$^{ff}$)N(R$^{ff}$)$_2$, —NR$^{ee}$C(=NR$^{ff}$)N(R$^{ff}$)$_2$, —NR$^{ee}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, haloalkyl, alkenyl, alkynyl, carbocyclyl, heterocyclyl, aryl, and heteroaryl, wherein, each of alkyl, alkenyl, alkynyl, carbocyclyl, heterocyclyl, aryl and heteroaryl is independently substituted with 0, 1, 2, 3, 4 or 5 R$^{gg}$ groups, or two geminal Rad substituents can be bound to form =O or =S;

each R$^{ee}$ is independently selected from alkyl, haloalkyl, alkenyl, alkynyl, carbocyclyl, aryl, heterocyclyl and heteroaryl, wherein, each of alkyl, alkenyl, alkynyl, carbocyclyl, heterocyclyl, aryl and heteroaryl is independently substituted with 0, 1, 2, 3, 4 or 5 R$^{gg}$ groups;

each R$^{ff}$ is independently selected from hydrogen, alkyl, haloalkyl, alkenyl, alkynyl, carbocyclyl, heterocyclyl, aryl and heteroaryl, or two R$^{ff}$ groups are bound to form heterocyclyl or heteroaryl ring, wherein, each of alkyl, alkenyl, alkynyl, carbocyclyl, heterocyclyl, aryl and heteroaryl is independently substituted with 0, 1, 2, 3, 4 or 5 R$^{gg}$ groups;

each R$^{gg}$ is independently: halo, —CN, —NO$_2$, —N$_3$, —SO$_2$H, —SO$_3$H, —OH, —OC$_{1-6}$alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_2$-C$_6$ alkenyl, C$_2$-C$_6$ alkynyl, C$_3$-C$_7$ carbocyclyl, C$_6$-C$_{10}$ aryl, C$_3$-C$_7$ heterocyclyl, or C$_5$-C$_{10}$ heteroaryl; or two geminal R$^{gg}$ substituents can be bound to form =O or =S; wherein, X$^-$ is a counter ion.

Exemplary substituents on the nitrogen atom include but are not limited to: hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, carbocyclyl, heterocyclyl, aryl and heteroaryl, or two R$^{cc}$ groups connected to the nitrogen atom are bound to form heterocyclyl or heteroaryl ring, wherein, each of alkyl, alkenyl, alkynyl, carbocyclyl, heterocyclyl, aryl and heteroaryl is independently substituted with 0, 1, 2, 3, 4 or 5 R$^{dd}$ groups, and wherein R$^{aa}$, R$^{bb}$, R$^{cc}$ and R$^{dd}$ are as defined above.

"Deuterated", "deuteration", or "D" means that one or more hydrogens in a compound or group are replaced by deuterium; Deuteration can be mono-, di-, poly-, or fully-substituted. The term "substituted with one or more deuteriums" can be used interchangeably with "deuterated one or more times".

"Non-deuterated compound" refers to a compound whose content of deuterium atoms is not higher than the natural content (0.015%) of deuterium isotope.

The content of deuterium isotope at a deuterated position is at least greater than the natural content of deuterium isotope (0.015%), alternatively greater than 30%, yet alternatively greater than 50%, yet alternatively greater than 75%, yet alternatively greater than 95%, or yet alternatively greater than 99%.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences (1977) 66:1-19. Pharmaceutically acceptable salts of the compounds disclosed herein include those derived from suitable inorganic and organic acids and bases. Examples of pharmaceutically acceptable, nontoxic acid addition salts are salts formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid. Salts formed using conventional methods in the art such as ion exchange are also included. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Active metabolite" refers to a pharmacologically active product obtained by metabolism of a compound of formula (I) or a salt thereof in vivo. Prodrugs and active metabolites of compounds can be determined using conventional techniques known or available in the art.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In some embodiments, the subject is a human. In some embodiments, the subject is a non-human animal. The terms "human," "patient," and "subject" are used interchangeably herein.

"Disease", "disorder" and "condition" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

"Combination", "combined", and related terms refer to the simultaneous or sequential administration of the therapeutic agents of the present disclosure. For example, the compound disclosed herein may be administered with another therapeutic agent simultaneously or sequentially in separate unit dosage forms, or together in a single unit dosage form.

DETAILED DESCRIPTION OF THE INVENTION

Compound

In the present disclosure, "compound of the present disclosure" or "compound disclosed herein" refers to the following compound of formula (I) (including various kinds of subsets), or a pharmaceutically acceptable salt, hydrate or solvate thereof.

In one embodiment, the present disclosure related to a compound of formula (I):

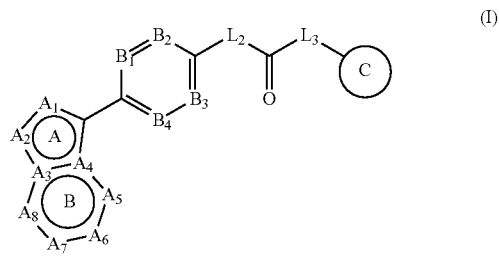

wherein
ring A and ring B form an aromatic fused ring;
$A_1$ is selected from N atom and C atom, which are optionally substituted with $R_1$;
$A_2$ is selected from N atom and C atom, which are optionally substituted with $R_2$;
wherein each instance of $R_1$ and $R_2$ is each independently selected from H, D, halogen, —CN, $C_{1-6}$ alkyl, $C_{1-6}$ haloalkyl, $C_{3-7}$ cycloalkyl, $C_{1-6}$ alkoxyl, $C_{1-6}$ haloalkoxyl, and —$OC_{3-7}$ cycloalkyl; wherein the above groups are optionally substituted with one or more D, until fully deuterated;
$A_3$ and $A_4$ are each independently selected from C atom and N atom;
$A_5$ and $A_6$ are each independently selected from N atom and C atom, which are optionally substituted with R;
$A_7$ and $A_8$ are each independently selected from N atom and C atom, which are optionally substituted with R';
wherein R and R' are each independently selected from H, D, halogen, —CN, $C_{1-6}$ alkyl, $C_{1-6}$ haloalkyl, $C_{3-7}$ cycloalkyl, $C_{1-6}$ alkoxyl, $C_{1-6}$ haloalkoxyl, —$OC_{3-7}$ cycloalkyl, and -$L_1$-$R_a$; wherein the above groups are optionally substituted with one or more D, until fully deuterated;
wherein $L_1$ is selected from bond, O, and NH; $R_a$ is selected from phenyl, and 5- to 6-membered heteroaryl containing 1-3 heteroatoms selected from N, O and S, wherein the groups are optionally substituted with one or more $R_b$;
$B_1$, $B_2$, $B_3$ and $B_4$ are each independently selected from CR* and N;
wherein each instance of R* is each independently selected from H, D, halogen, —CN, —$R_c$, —$C(O)R_c$, —C(O)OR$_c$, —C(O)NR$_c$R$_d$, —NR$_c$R$_d$, —NR$_c$C(O)R$_c$, —NR$_c$C(O)OR$_c$, —NR$_c$C(O)NR$_c$R$_d$, —OR$_c$, —OC(O)R$_c$, —OC(O)OR$_c$, and —OC(O)NR$_c$R$_d$;

L$_2$ and L$_3$ are each independently selected from bond, NH, CH$_2$, CHD and CD$_2$;

ring C is selected from phenyl, and 5- to 6-membered heteroaryl containing 1-3 heteroatoms selected from N, O and S, wherein the groups are optionally substituted with one or more R$_b$;

wherein each instance of R$_b$ and R$_{b'}$ is each independently selected from H, D, —OH, —NH$_2$, halogen, —CN, —R$_c$, —C(O)R$_c$, —C(O)OR$_c$, —C(O)NR$_c$R$_d$, —NR$_c$R$_d$, —NR$_c$C(O)R$_c$, —NR$_c$C(O)OR$_c$, —NR$_c$C(O)NR$_c$R$_d$, —OR$_c$, —OC(O)R$_c$, —OC(O)OR$_c$, and —OC(O)NR$_c$R$_d$, or two R$_b$ groups or two R$_{b'}$ groups attached to the same atom or adjacent atoms can together form C$_{3-7}$ cycloalkyl, 3- to 7-membered heterocyclyl, C$_{6-10}$ aryl, or 5- to 10-membered heteroaryl, wherein C$_{3-7}$ cycloalkyl, 3- to 7-membered heterocyclyl, C$_{6-10}$ aryl, and 5- to 10-membered heteroaryl is optionally substituted with one or more R$_e$;

each instance of R$_c$ and R$_d$ is each independently selected from C$_{1-6}$ alkyl, C$_{1-6}$ haloalkyl, C$_{2-6}$ alkenyl, C$_{2-6}$ alkynyl, C$_{3-7}$ cycloalkyl, 3- to 7-membered heterocyclyl, C$_{6-10}$ aryl, and 5- to 10-membered heteroaryl, or R$_c$ and R$_d$ together with the N atom to which they are attached form a 3- to 7-membered heterocyclyl, or 5- to 10-membered heteroaryl; wherein the groups are optionally substituted with one or more R$_e$;

each instance of R$_e$ is independently selected from H, D, —OH, —NH$_2$, halogen, —CN, —R$_f$, —C(O)R$_f$, —C(O)OR$_f$, —C(O)NR$_f$R$_g$, —NR$_f$R$_g$, —NR$_f$C(O)R$_f$, —NR$_f$C(O)OR$_f$, —NR$_f$C(O)NR$_f$R$_g$, —OR$_f$, —OC(O)R$_f$, —OC(O)OR$_f$, and —OC(O)NR$_f$R$_g$, or two R$_e$ groups attached to the same atom or adjacent atoms can together form C$_{3-7}$ cycloalkyl, 3- to 7-membered heterocyclyl, C$_{6-10}$ aryl, or 5- to 10-membered heteroaryl; wherein each group in the definition of R$^e$ is optionally substituted with one or more D, until fully deuterated;

each instance of R$_f$ and R$_g$ is each independently selected from C$_{1-6}$ alkyl, C$_{1-6}$ haloalkyl, C$_{2-6}$ alkenyl, C$_{2-6}$ alkynyl, C$_{3-7}$ cycloalkyl, 3- to 7-membered heterocyclyl, C$_{6-10}$ aryl, and 5- to 10-membered heteroaryl, or R$_f$ and R$_g$ together with the N atom to which they are attached form a 3- to 7-membered heterocyclyl, or 5- to 10-membered heteroaryl; wherein each group in the definition of R$_f$ and R$_g$ is optionally substituted with one or more D, until fully deuterated;

or a tautomer, stereoisomer, prodrug, crystal form, pharmaceutically acceptable salt, hydrate or solvate thereof.

A$_1$, A$_2$, A$_3$, A$_4$, A$_5$, A$_6$, A$_7$, and A$_8$

In a specific embodiment, A$_1$ is selected from NR$_1$; in another specific embodiment, A$_1$ is selected from CR$_1$. In another specific embodiment, A$_1$ is selected from CH.

In a specific embodiment,

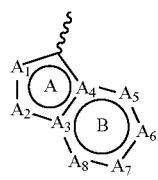

is selected from

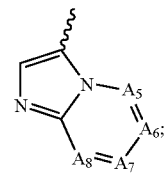

In another specific embodiment,

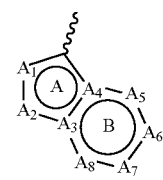

is selected from

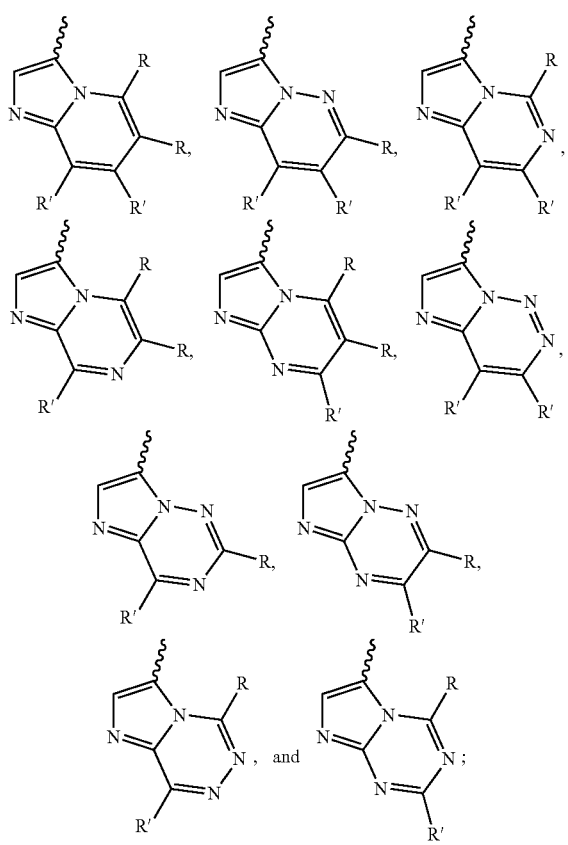

In another specific embodiment, is selected from
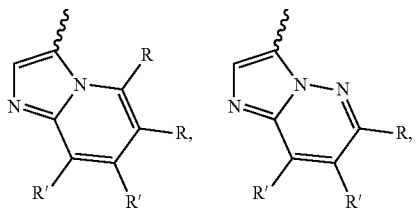
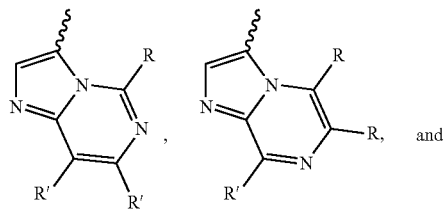
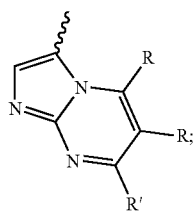
In another specific embodiment,
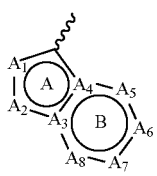
is selected from
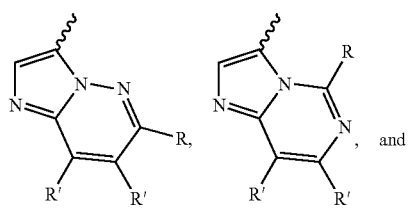
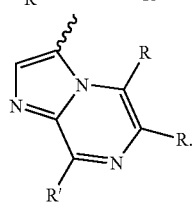
In another specific embodiment,
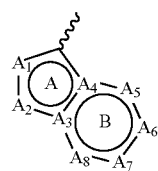
is selected from
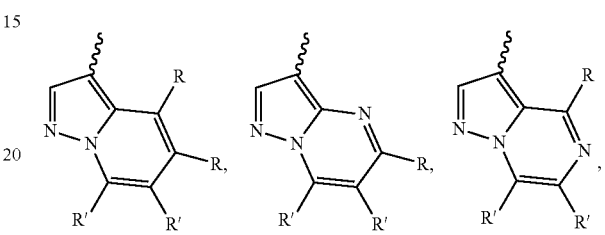
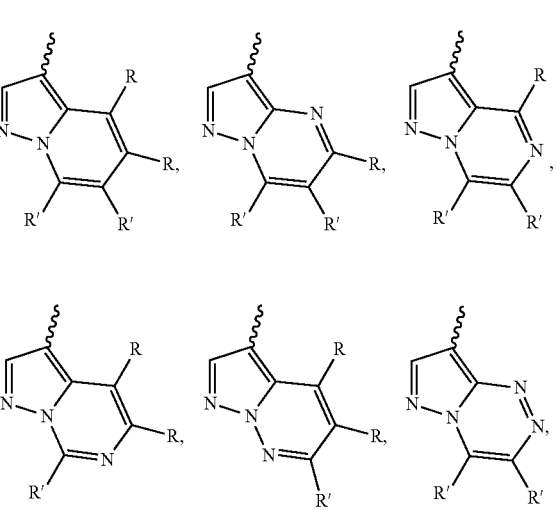
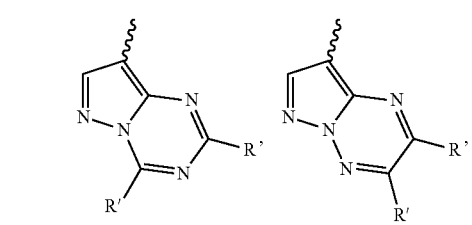
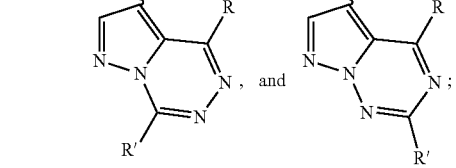
In another specific embodiment,
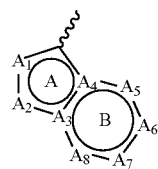

is selected from
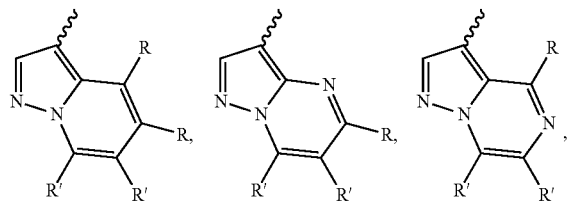 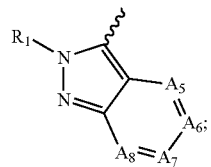
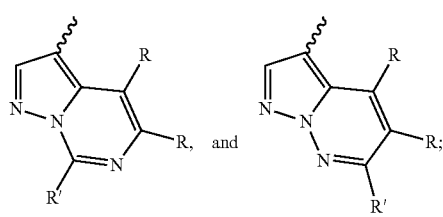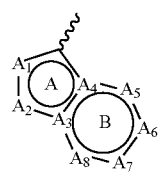
In another specific embodiment,
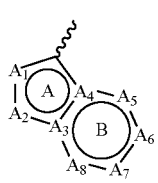
is selected from
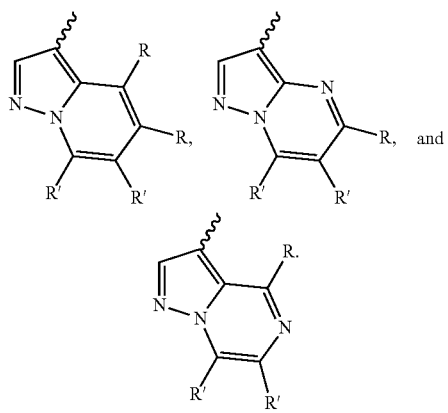
In a specific embodiment,
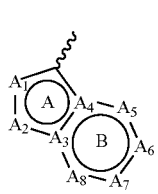
is selected from
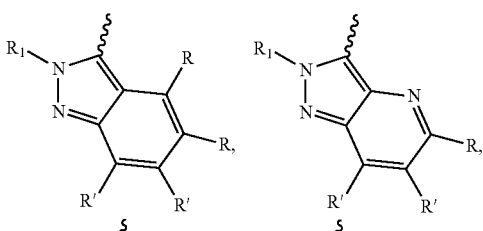
In another specific embodiment,
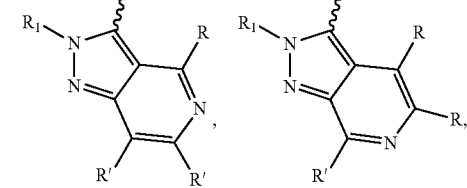
is selected from
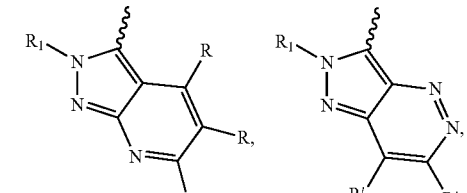
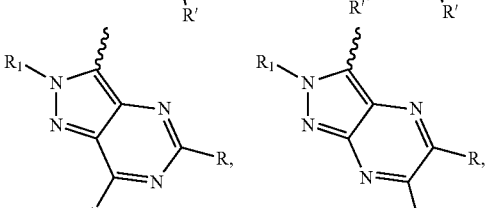
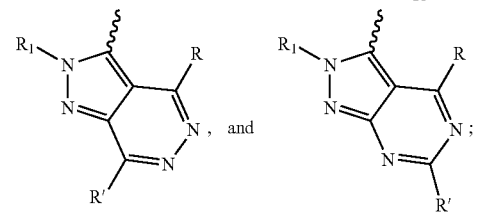

In another specific embodiment,

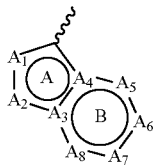

is selected from

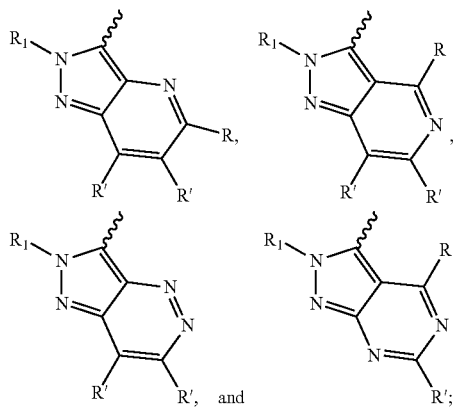

$B_1$, $B_2$, $B_3$ and $B_4$

In a specific embodiment, $B_1$, $B_2$, $B_3$, and $B_4$ are each independently selected from CR* and N; in another specific embodiment, $B_1$, $B_2$, $B_3$, and $B_4$ are each independently selected from CR*; in another specific embodiment, $B_1$, $B_2$, and $B_3$ are each independently selected from CR*, and $B_4$ is selected from N; in another specific embodiment, $B_2$ and $B_3$ are each independently selected from CR*, and $B_1$ and $B_4$ are each independently selected from N.

In a specific embodiment,

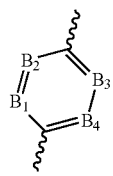

is selected from

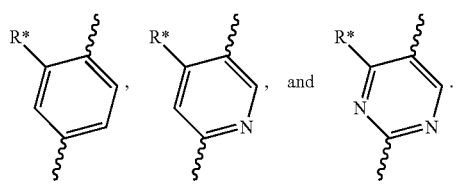

R*

In a specific embodiment, each instance of R* is independently selected from H, D, halogen, —CN, —$R_c$, —C(O)$R_c$, —C(O)O$R_c$, —C(O)N$R_cR_d$, —N$R_cR_d$, —$NR_c$C(O)$R_c$, —O$R_c$, —OC(O)$R_c$, —OC(O)O$R_c$, and —OC(O)N$R_cR_d$; in another specific embodiment, each instance of R* is independently selected from H, D, halogen, CN, and $C_{1-6}$ alkyl; in another specific embodiment, each instance of R* is independently selected from H, F, Cl, Br, CN, methyl, and —$CD_3$; in another specific embodiment, each instance of R* is independently selected from H and F; in another specific embodiment, each group defined as R* is optionally substituted with one or more D, until fully deuterated.

R, R', $L_1$, and $R_a$

In a specific embodiment, each instance of R and R' is each independently selected from H, halogen, —CN, $C_{1-6}$ alkyl, and -$L_1$-$R_a$; in another specific embodiment, each instance of R is each independently selected from H, halogen, CN, and $C_{1-6}$ alkyl; in another specific embodiment, each instance of R' is each independently selected from H, halogen, CN, $C_{1-6}$ alkyl, and -$L_1$-$R_a$; in another specific embodiment, each instance of R' is each independently selected from H and -$L_1$-$R_a$.

In a specific embodiment of R and R', $L_1$ is selected from bond; in another specific embodiment of R and R', $L_1$ is selected from NH.

In a specific embodiment of R and R', $R_a$ is selected from phenyl, and 5- to 6-membered heteroaryl containing 1-3 heteroatoms selected from N, O and S, wherein the groups are optionally substituted with one or more $R_b$; in another specific embodiment, $R_a$ is selected from phenyl, pyridyl, pyrimidinyl, pyrazinyl, pyridazinyl, pyrrolyl, pyrazolyl, imidazolyl, furanyl, oxazolyl, isoxazolyl, thienyl, thiazolyl, and isothiazolyl, wherein the groups are optionally substituted with one or more $R_b$; in another specific embodiment, $R_a$ is selected from phenyl, pyrazolyl, imidazolyl, oxazolyl, and isoxazolyl, wherein the groups are optionally substituted with one or more $R_b$; in another specific embodiment, $R_a$ is selected from pyrazolyl, wherein the groups are optionally substituted with one or more $R_b$.

In a specific embodiment, $R_a$ is selected from

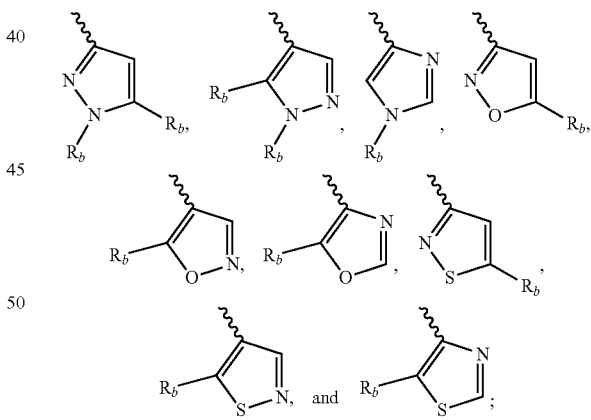

In another specific embodiment, $R_a$ is selected from

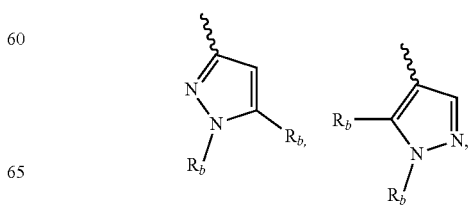

-continued

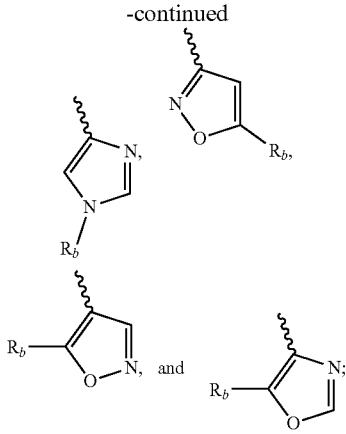

In another specific embodiment, $R_a$ is selected from

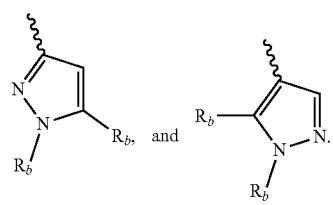

$R_b$

In a specific embodiment, each instance of $R_b$ is each independently selected from H and $C_{1-6}$ alkyl, wherein the $C_{1-6}$ alkyl is optionally substituted with halogen, —OH, —NH$_2$, —N($C_{1-6}$ alkyl)$_2$, $C_{1-6}$ alkoxyl, $C_{3-7}$ cycloalkyl, or 3- to 7-membered heterocyclyl; in another specific embodiment, each instance of $R_b$ is each independently selected from H or $C_{1-6}$ alkyl, wherein the $C_{1-6}$ alkyl is optionally substituted with one or more groups selected from halogen, —OH, —NH$_2$, —N($C_{1-6}$ alkyl)$_2$, and $C_{1-6}$ alkoxyl; in another specific embodiment, each instance of $R_b$ is each independently selected from H, methyl, isopropyl, —CH$_2$CH$_2$OH, —CH$_2$CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, and —CH$_2$CH$_2$CH$_2$N(CH$_3$)$_2$; in another specific embodiment, each group defined as $R_b$ is optionally substituted with one or more D, until fully deuterated.

Ring C

In a specific embodiment, ring C is selected from phenyl and 5- to 6-membered heteroaryl containing 1-3 heteroatoms selected from N, O and S, wherein the phenyl and 5- to 6-membered heteroaryl are optionally substituted with one or more $R_b{'}$; in another specific embodiment, ring C is selected from phenyl, pyridyl, pyrimidinyl, pyrazinyl, pyridazinyl, pyrrolyl, pyrazolyl, imidazolyl, furanyl, oxazolyl, isoxazolyl, thienyl, thiazolyl, and isothiazolyl, wherein the groups are optionally substituted with one or more $R_b{'}$; in another specific embodiment, ring C is selected from phenyl, pyrazolyl, imidazolyl, oxazolyl, and isoxazolyl, wherein the groups are optionally substituted with one or more $R_b{'}$; in another specific embodiment, ring C is selected from phenyl, pyridyl, oxazolyl, and isoxazolyl, wherein the groups are optionally substituted with one or more $R_b{'}$;

In another specific embodiment, ring C is selected from

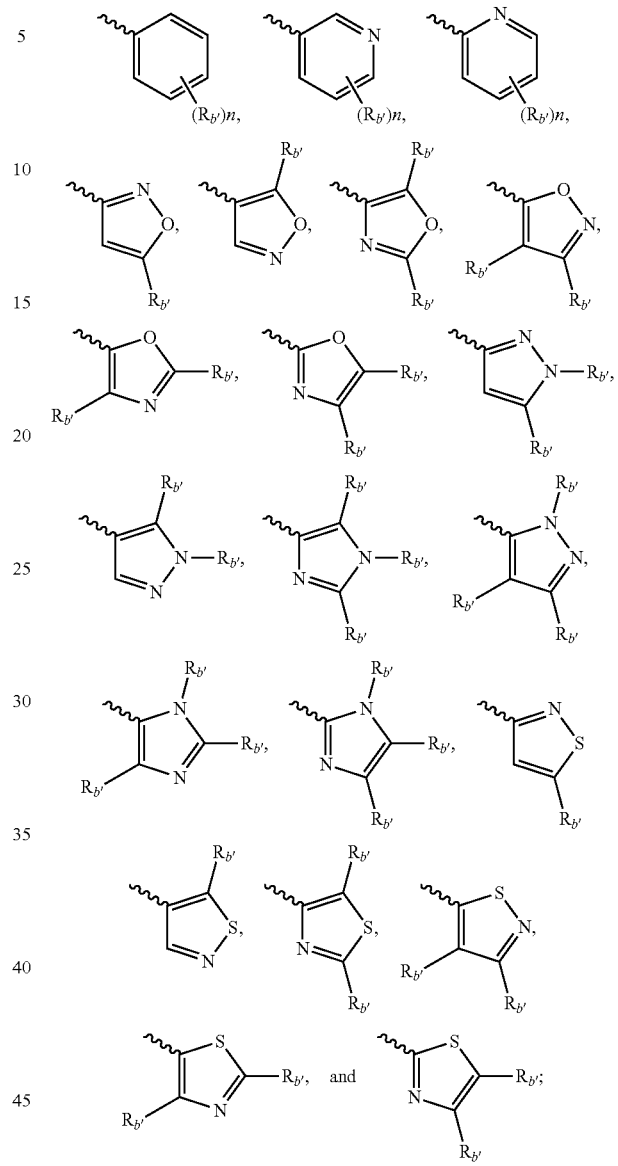

In another specific embodiment, ring C is selected from

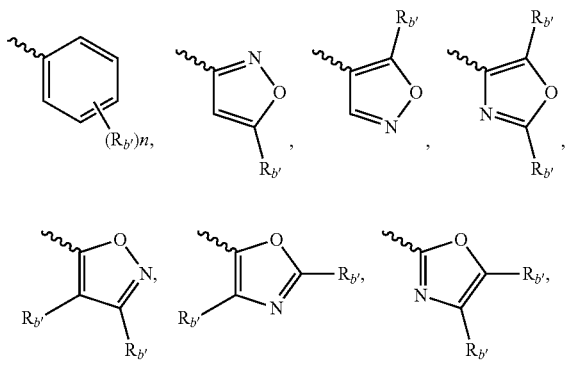

-continued

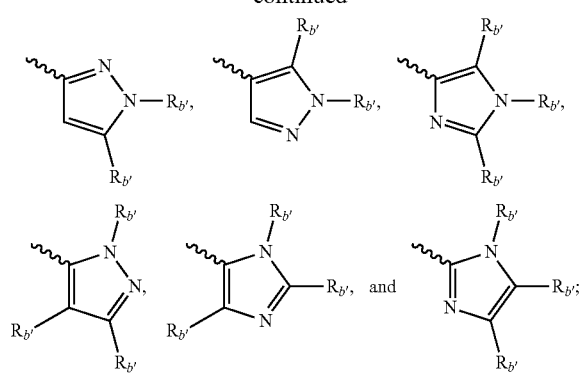

In another specific embodiment, ring C is selected from

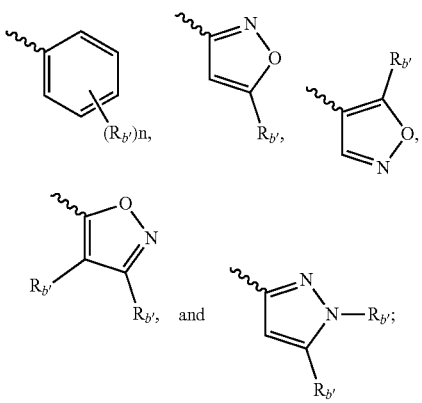

wherein n is selected from 0, 1, 2, and 3.

$R_{b'}$

In a specific embodiment, each instance of $R_{b'}$ is each independently selected from H, halogen, $C_{1-6}$ alkyl, $C_{3-7}$ cycloalkyl, 3- to 7-membered heterocyclyl, $C_{6-10}$ aryl, and 5- to 10-membered heteroaryl, wherein the $C_{1-6}$ alkyl, $C_{3-7}$ cycloalkyl, 3- to 7-membered heterocyclyl, $C_{6-10}$ aryl, and 5- to 10-membered heteroaryl are optionally substituted with one or more groups selected from halogen, $C_{1-6}$ alkyl, $C_{1-6}$ alkoxyl, $C_{1-6}$ haloalkyl, $C_{1-6}$haloalkoxyl, $C(O)C_{1-6}$ alkyl, —C(O)O$C_{1-6}$ alkyl, —C(O)N($C_{1-6}$ alkyl)$_2$, —OC(O)$C_{1-6}$ alkyl, —N($C_{1-6}$ alkyl)C(O)$C_{1-6}$ alkyl, and —N($C_{1-6}$ alkyl)C(O)O$C_{1-6}$ alkyl; in another specific embodiment, each instance of $R_{b'}$ is each independently selected from H and $C_{1-6}$ alkyl, wherein the $C_{1-6}$ alkyl is optionally substituted with one or more groups selected from halogen and $C_{1-6}$ haloalkyl; in another specific embodiment, each instance of $R_{b'}$ is each independently selected from F, —CH(CH$_3$)$_2$, —C(CH$_3$)$_2$CH$_2$OH, —CF$_3$, —C(CH$_3$)$_3$, —CF$_2$(CH$_3$), —C(CH$_3$)(CH$_2$F)$_2$, —C(CH$_3$)$_2$CF$_3$, —C(CF$_3$)$_2$CH$_3$, —C(CH$_3$)$_2$CH$_2$F, —CF(CH$_3$)$_2$, cyclopropyl, cyclobutyl, cyclopentyl, cyclohexyl,

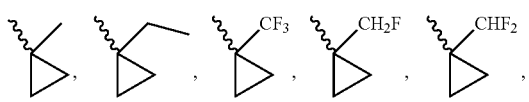

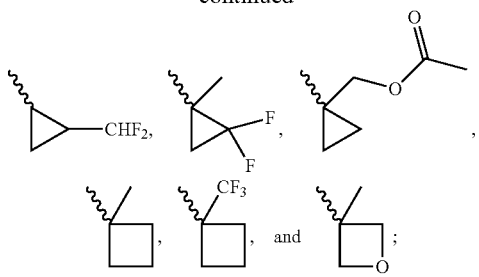

in another specific embodiment, each instance of $R_{b'}$ is each independently selected from F, —CF$_3$, —C(CH$_3$)$_3$, —C(CH$_3$)$_2$CF$_3$, and —C(CF$_3$)$_2$CH$_3$; in another specific embodiment, each group defined as $R_{b'}$ is optionally substituted with one or more D, until fully deuterated.

$L_2$ and $L_3$

In a specific embodiment, $L_2$ and $L_3$ are each independently selected from bond, NH, CH$_2$, CHD, and CD$_2$; in another specific embodiment, $L_2$ is selected from bond; in another specific embodiment, $L_2$ is selected from NH; in another specific embodiment, $L_2$ is selected from CH$_2$; in another specific embodiment, $L_2$ is selected from CHD; in another specific embodiment, $L_2$ is selected from CD$_2$; in another specific embodiment, $L_3$ is selected from bond; in another specific embodiment, $L_3$ is selected from NH; in another specific embodiment, $L_3$ is selected from CH$_2$; in another specific embodiment, $L_3$ is selected from CHD; in another specific embodiment, $L_3$ is selected from CD$_2$.

In another embodiment, the present disclosure relates to the following compounds of the formulae:

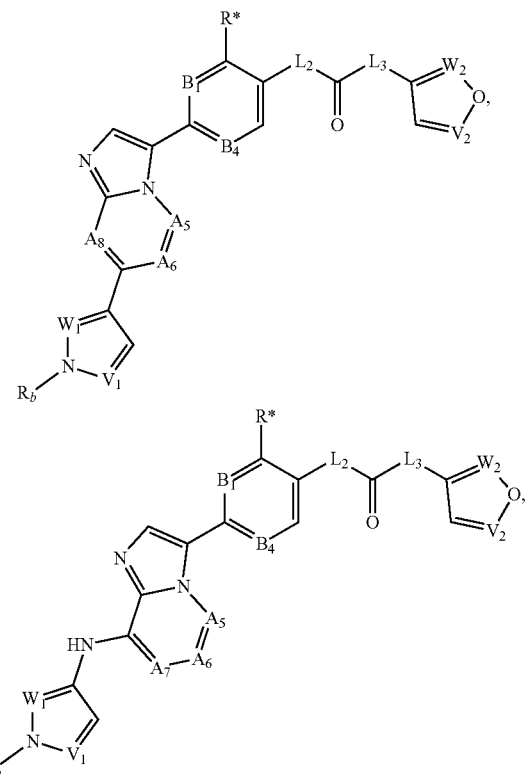

-continued
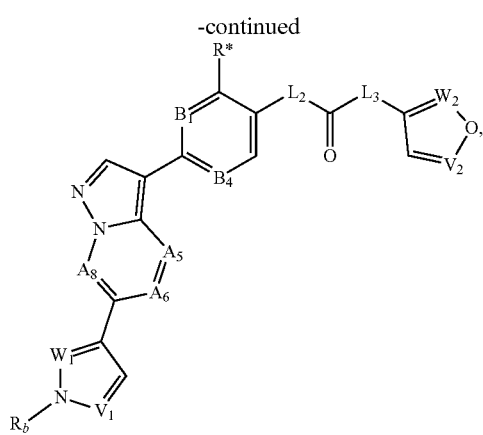
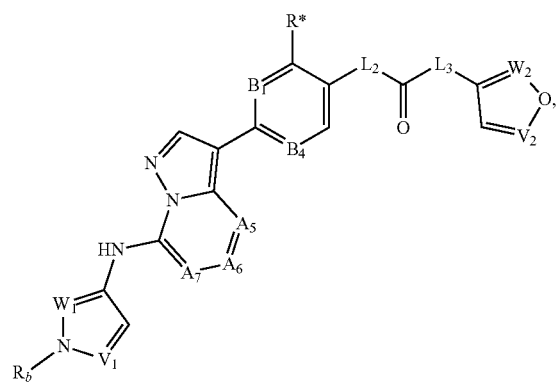
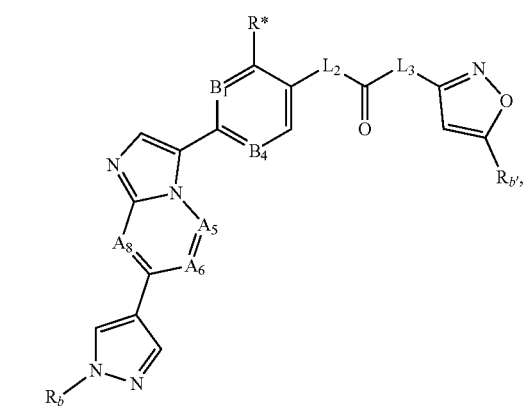
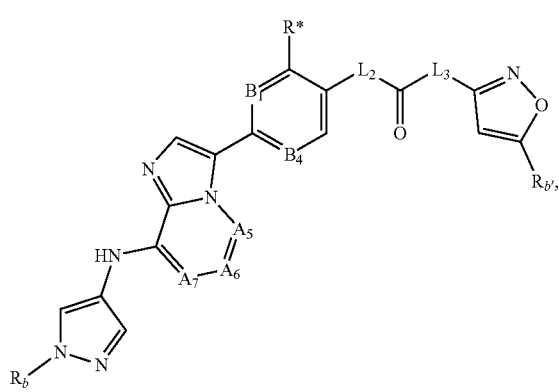
-continued
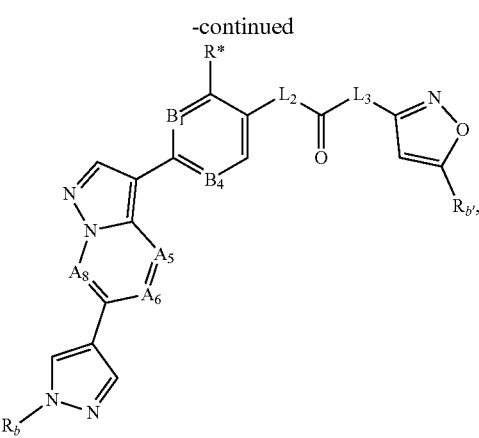
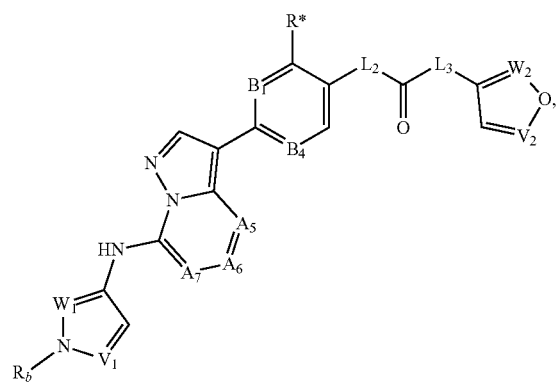
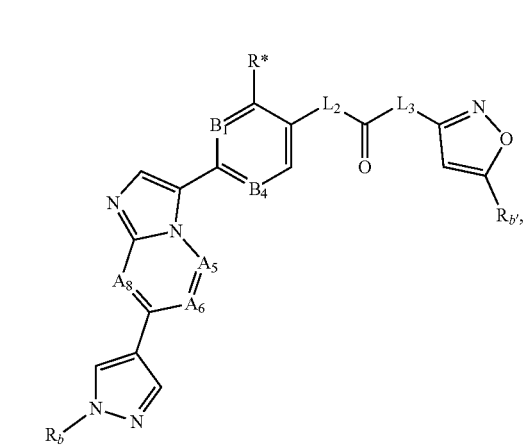
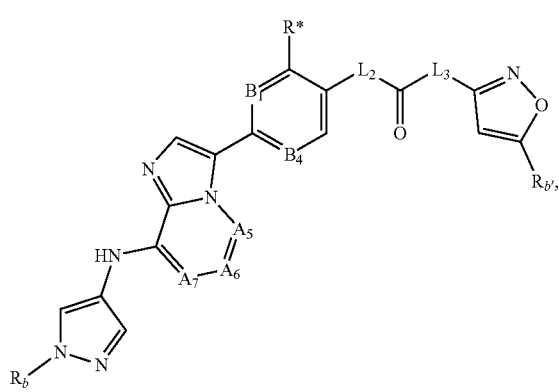

27
-continued
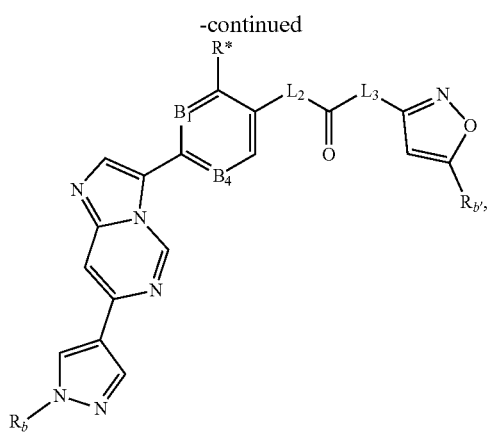
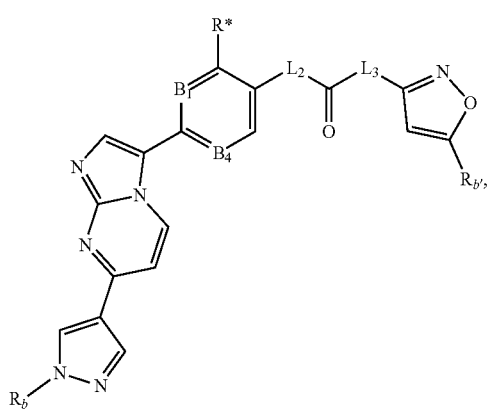
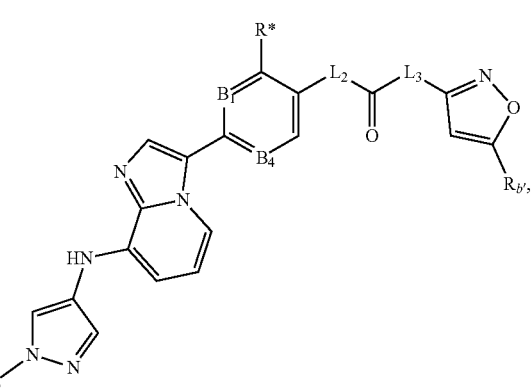
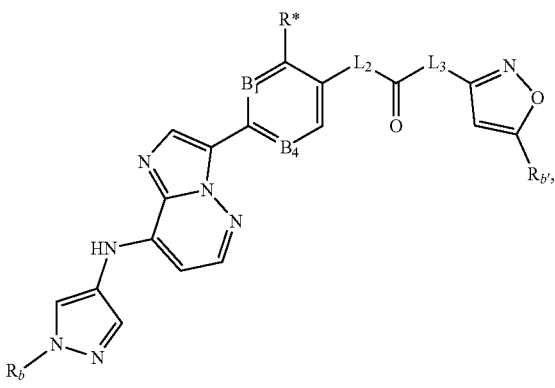
28
-continued
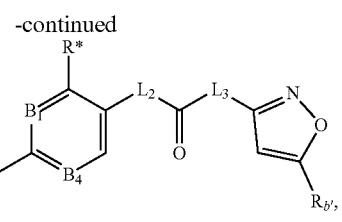
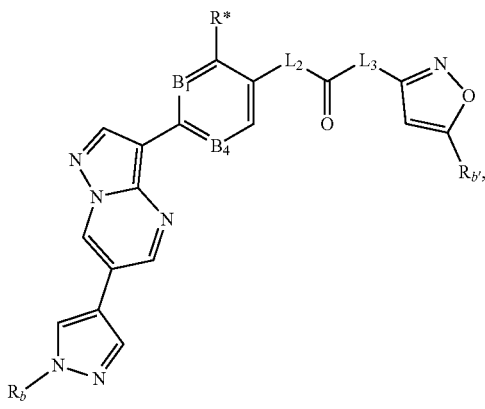

-continued

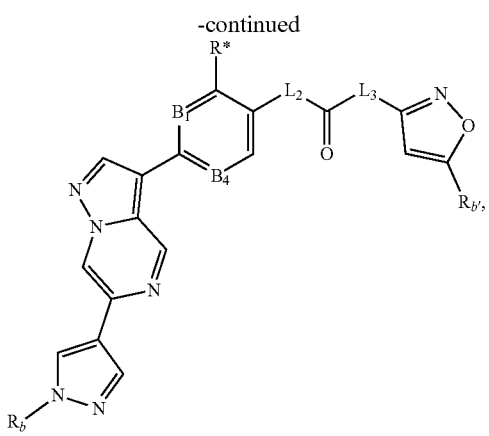

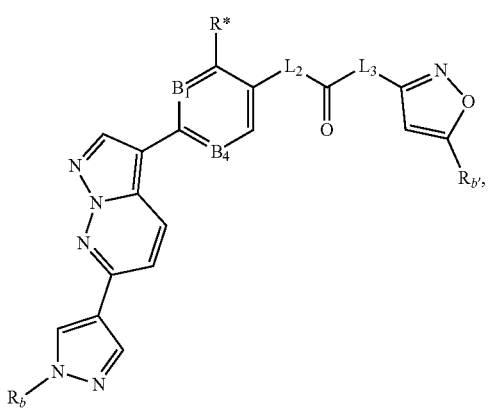

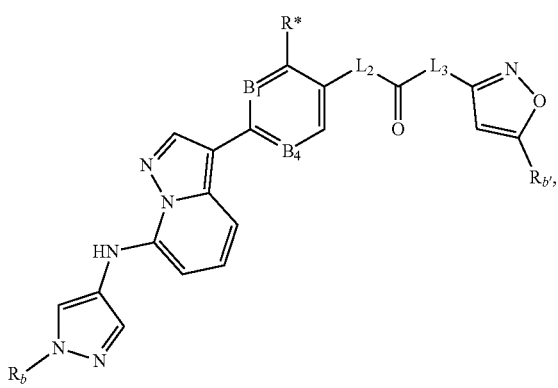

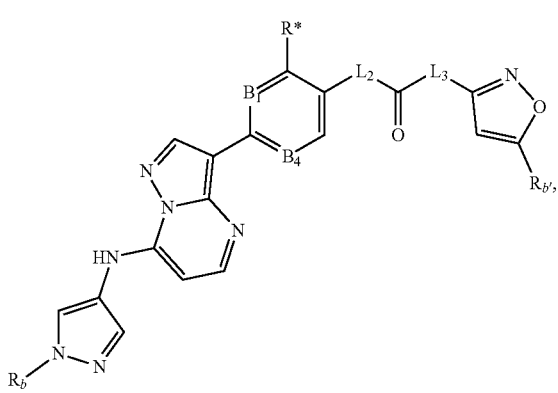

-continued

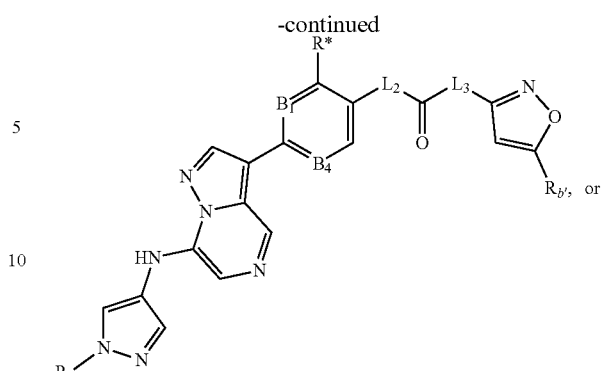

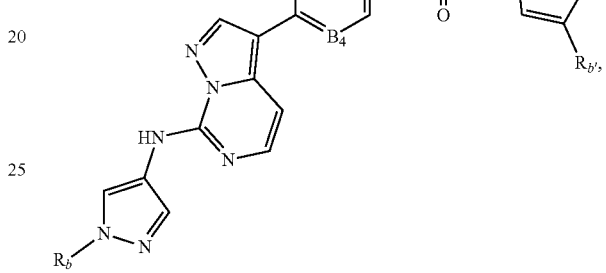

wherein $W_1$ and $V_1$ are each independently selected from $CR_b$ and N;

$W_2$ and $V_2$ are each independently selected from $CR_{b'}$ and N; and other parameters are defined as above.

In another embodiment, the present disclosure relates to the following compounds of the formula: d

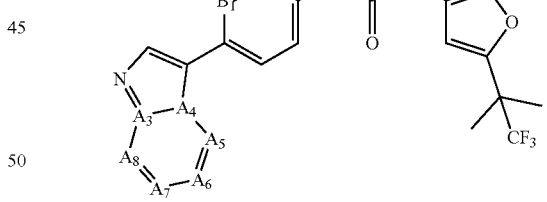

$A_3$ and $A_4$ are each independently selected from C atom and N atom, wherein one C atom and one N atom are contained;

$A_5$ and $A_6$ are each independently selected from N atom and C atom, which are optionally substituted with R;

$A_7$ and $A_8$ are each independently selected from N atom and C atom, which are optionally substituted with R';

wherein each instance of R is each independently selected from H, D, halogen, and —CN;

each instance of R' is each independently selected from H, D, halogen, —CN, and $-L_1-R_a$;

wherein one of $A_7$ and $A_8$ is substituted with $-L_1-R_a$;

wherein $L_1$ is selected from bond, O, and NH; $R_a$ is

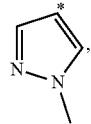

wherein * indicates the location of attachment to $L_1$;

$B_1$ and $B_2$ are each independently selected from CR* and N;

wherein each instance of R* is each independently selected from H, D, halogen, and —CN;

or a tautomer, stereoisomer, prodrug, crystal form, pharmaceutically acceptable salt, hydrate or solvate thereof.

In another embodiment, the present disclosure relates to the following compounds of the formula:

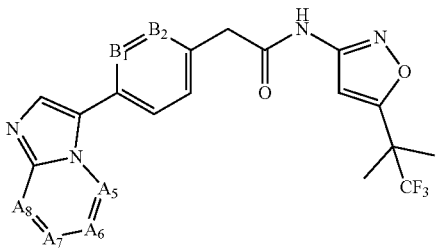

wherein $A_5$ and $A_6$ are each independently selected from N atom and C atom, which are optionally substituted with R;

$A_7$ and $A_8$ are each independently selected from N atom and C atom, which are optionally substituted with R';

wherein each instance of R is each independently selected from H, D, halogen, and —CN;

each instance of R' is each independently selected from H, D, halogen, —CN, and -$L_1$-$R_a$;

and at least one of $A_5$, $A_6$ and $A_7$ is N, and one of $A_7$ and $A_8$ is substituted with -$L_1$-$R_a$;

wherein $L_1$ is selected from bond, O, and NH; $R_a$ is

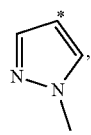

wherein * indicates the location of attachment to $L_1$;

$B_1$ and $B_2$ are each independently selected from CR* and N;

wherein each instance of R* is each independently selected from H, D, halogen, and —CN;

or a tautomer, stereoisomer, prodrug, crystal form, pharmaceutically acceptable salt, hydrate or solvate thereof.

In another embodiment, the present disclosure relates to the following compounds of the formula:

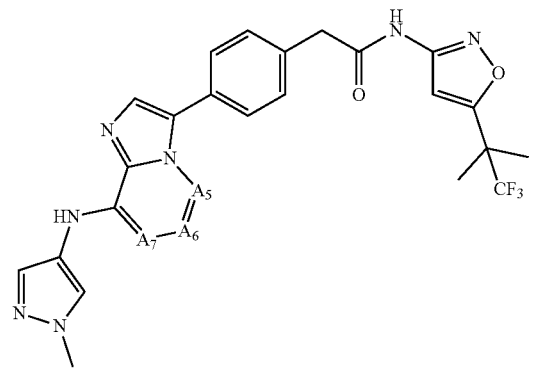

wherein $A_5$ and $A_6$ are each independently selected from N atom and C atom, which are optionally substituted with R;

$A_7$ is selected from N atom and C atom, which are optionally substituted with R'; and at least one of $A_5$, $A_6$ and $A_7$ is N;

wherein each instance of R is each independently selected from H, D, halogen, and —CN;

each instance of R' is each independently selected from H, D, halogen, and —CN;

or a tautomer, stereoisomer, prodrug, crystal form, pharmaceutically acceptable salt, hydrate or solvate thereof.

In another embodiment, the present disclosure relates to the following compounds of the formula:

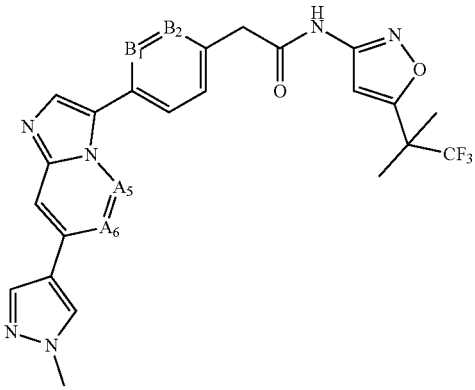

wherein $A_5$ and $A_6$ are each independently selected from N atom and C atom, which are optionally substituted with R, and at least one of $A_5$ and $A_6$ is N atom;

$B_1$ and $B_2$ are each independently selected from CR* and N;

wherein each instance of R is each independently selected from H, D, halogen, and —CN;

each instance of R* is each independently selected from H, D, halogen, and —CN;

alternatively, both of $B_1$ and $B_2$ are CR*;

or a tautomer, stereoisomer, prodrug, crystal form, pharmaceutically acceptable salt, hydrate or solvate thereof.

In another embodiment, the present disclosure relates to the following compounds of the formula:

wherein

- $A_5$ and $A_6$ are each independently selected from N atom and C atom, which are optionally substituted with R;
- $A_8$ is selected from N atom and C atom, which are optionally substituted with R';
- $B_1$ and $B_2$ are each independently selected from CR* and N;

wherein each instance of R is each independently selected from H, D, halogen, and —CN;

each instance of each instance of R* is each independently selected from H, D, halogen, and —CN;

alternatively, at least one of $A_5$, $A_6$, and $A_8$ is N atom; yet alternatively $A_5$ is N atom;

or a tautomer, stereoisomer, prodrug, crystal form, pharmaceutically acceptable salt, hydrate or solvate thereof.

In a more specific embodiment, the present disclosure relates to the following compounds:

35
-continued
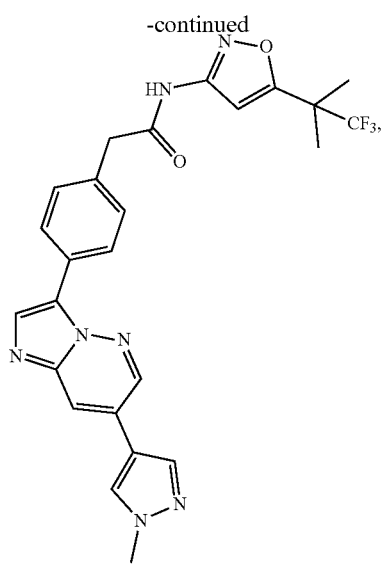
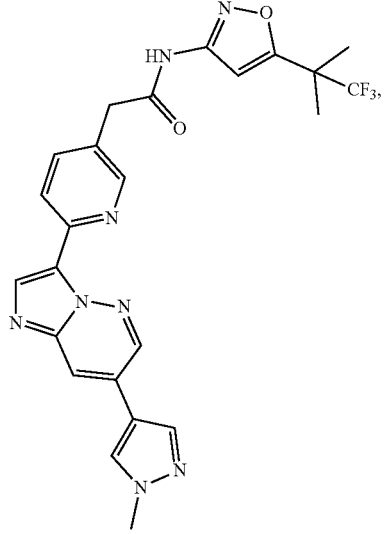
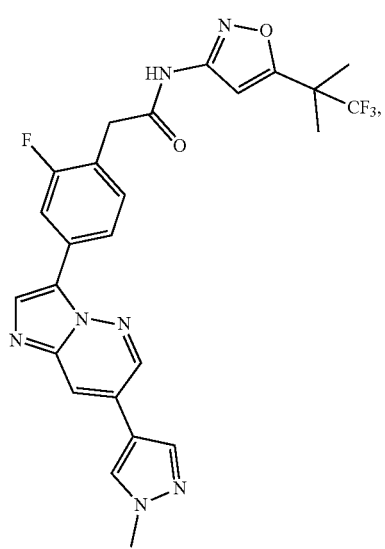
36
-continued
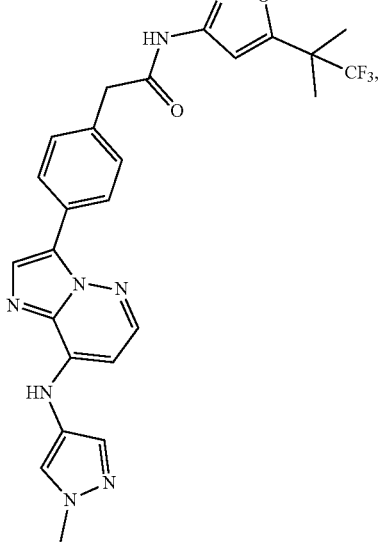
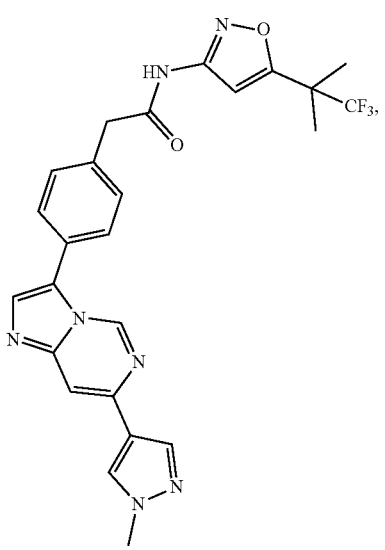
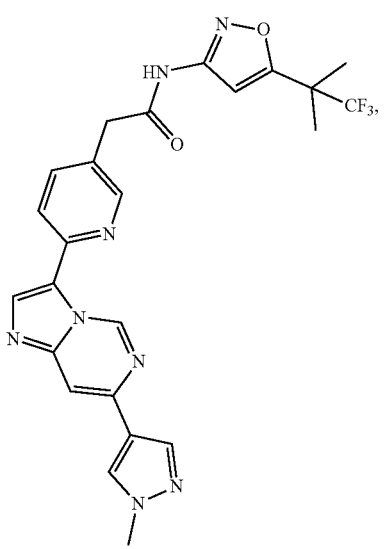

-continued

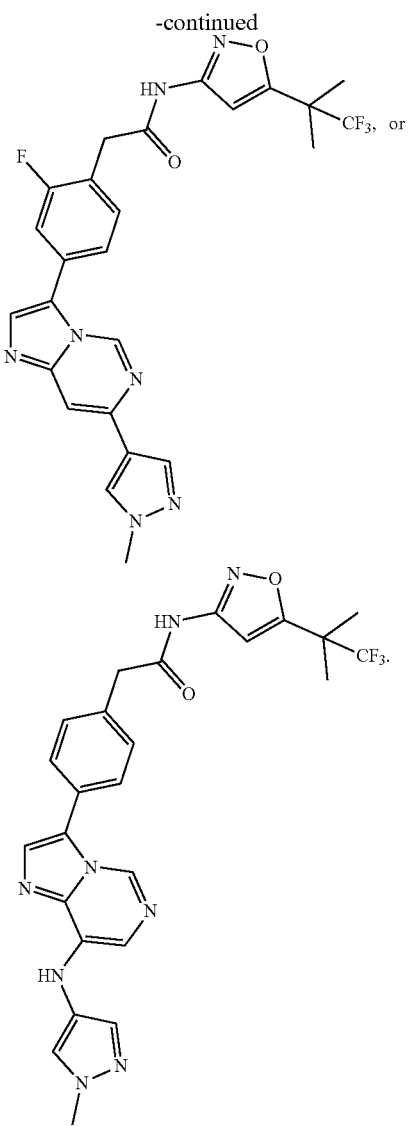

The compounds disclosed herein may include one or more asymmetric centers, and thus may exist in a variety of stereoisomeric forms, for example, enantiomers and/or diastereomers. For example, the compounds disclosed herein may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or alternative isomers can be prepared by asymmetric synthesis.

"Tautomer" refers to an isomer in which one functional group in a compound changes its structure into another functional group, wherein the compound and the isomer can quickly convert between each other, thus being in dynamic equilibrium; this two isomers are called tautomers.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds disclosed herein.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula R·x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R·0.5 $H_2O$)) and polyhydrates (x is a number greater than 1, for example, dihydrates (R·2 $H_2O$) and hexahydrates (R·6 $H_2O$)).

Compounds disclosed herein may be in an amorphous or crystalline form (crystal form or polymorph). Furthermore, the compounds disclosed herein may exist in one or more crystalline forms. Therefore, the present disclosure includes all amorphous or crystalline forms of the compounds disclosed herein within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes, which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds disclosed herein that comprise the above isotopes and/or other isotopes of other atoms, prodrugs thereof and pharmaceutically acceptable salts of said compounds or prodrugs all are within the scope of the present disclosure. Certain isotope-labeled compounds disclosed herein, such as those incorporating radioactive isotopes (e.g., $^3H$ and $^{14}C$), can be used for the measurement of the distribution of drug and/or substrate in tissue. Tritium, which is $^3H$ and carbon-14, which is $^{14}C$ isotope, are alternative, because they are easy to prepare and detect. Furthermore, replaced by heavier isotopes, such as deuterium, which is $^2H$, may provide therapeutic benefits due to the higher metabolic stability, such as prolonging the half-life in vivo or decreasing the dosage requirements, and thus may be alternative in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted in vivo into an active form that has medical effects by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

The prodrugs are any covalently bonded compounds disclosed herein, which release the parent compound in vivo when the prodrug is administered to a patient. Prodrugs are typically prepared by modifying functional groups in such a way that the modifications can be cleaved either by routine manipulation or decompose in vivo to yield the parent compound. Prodrugs include, for example, compounds disclosed herein wherein the hydroxy, amino or sulfhydryl groups are bonded to any group that, when administered to a patient, cleaves to form the hydroxy, amino or sulfhydryl groups. Thus, representative examples of prodrugs include (but are not limited to) the acetate/acetamide, formate/formamide and benzoate/benzamide derivatives of the hydroxy, amino or sulfhydryl functional groups of the compounds of formula (I). Furthermore, in the case of carboxylic acid (—COOH), esters such as methyl esters and ethyl esters, etc. can be employed. The ester itself may be active in their own and/or hydrolyzable under in vivo conditions in the human body. Suitable pharmaceutically acceptable in vivo hydrolysable ester groups include those groups that can readily break down in the human body to release the parent acids or salts thereof.

Pharmaceutical Composition, Formulation, and Kit

In another aspect, the disclosure provides a pharmaceutical composition comprising a compound disclosed herein (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (e.g., vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The pharmaceutical composition provided by the present disclosure may be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level rapidly. The placement of the bolus dose depends on the desired systemic levels of the active ingredient, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or alternatively from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with alternative doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and yet alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration may be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds disclosed herein can also be administered in sustained release forms or from sustained release drug delivery systems. A description of representative sustained release materials may be found in Remington's Pharmaceutical Sciences.

The present disclosure also relates to the pharmaceutically acceptable formulations of a compound disclosed herein. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376, 645. In certain embodiments, the formulation comprises hexapropyl-β-cyclodextrin (e.g., 10-50% in water).

Indication

Provided herein is a method of treating, preventing or ameliorating diseases or disorders modulated or otherwise affected by one or more of RET, Trk, FLT3, c-Kit, PDGFR, and VEGFR kinases (including one or more of wild-type and/or mutant RET, Trk, FLT3, c-Kit, PDGFR, and VEGFR kinases), or one or more symptoms or causes thereof.

The present disclosure provides a method of treating diseases mediated by protein kinases in a subject, comprising administering to the subject a compound disclosed herein, or a pharmaceutically acceptable salt, hydrate or solvate thereof, or a pharmaceutical composition disclosed herein.

As used herein, the term "wild-type" refers to the most common genes or alleles found in organisms. In some specific embodiments, "wild-type" refers to a gene or allele that does not have a mutation.

As used herein, the term "cancer" refers to the abnormal growth of cells that proliferate in uncontrolled way and metastasize in some circumstances. Types of cancer include, but are not limited to, solid tumors, such as bladder tumor, intestine tumor, brain tumor, breast tumor, endometrial tumor, heart tumor, kidney tumor, lung tumor, lymphoid tissue tumor (lymphoma), ovary tumor, pancreas tumor, or other endocrine organ (thyroid) tumor, prostate tumor, skin tumor (melanoma), or hematological tumor (e.g., leukemia) and so on.

RET

In a specific embodiment, compounds disclosed herein are inhibitors of a RET kinase, and can be used for treating, preventing or ameliorating diseases or disorders that are modulated or otherwise affected by one or more of wild-type RET and RET kinase domain mutants, or one or more symptoms or causes thereof. Such diseases or disorders include, but are not limited to, proliferative conditions (e.g., cancers, including hematological cancers and solid tumors) and gastrointestinal diseases (IBS) that can be treated, prevented or controlled by modulating various activities of kinases (including dimerization, ligand binding, and phosphotransferase activities) or by modulating the expression of kinases.

As used herein, the term "RET kinase domain mutants" refers to one or more mutants of RET kinase domain, or alternatively, refers to RET (protein itself becomes the "RET kinase domain mutant") comprising one or more of the mutations. Mutations in the RET kinase domain can be insertions, deletions, or point mutations. In a specific embodiment, mutations of RET kinase domain comprise at least one point mutation in the RET kinase domain. In another specific embodiment, mutations of RET kinase domain comprise at least one point mutation in the RET kinase domain. In another specific embodiment, the point mutation in the RET kinase domain is selected from S32L, D34S, L40P, P64L, $R_{67}H$, $R_114H$, V145G, V292M, G321R, R330Q, T338I, R360W, F393L, $A_5$10V, E511K, C515S, C531R, G533C, G533S, G550E, V591I, G593E, I602V, R600Q, K603Q, K603E, Y606C, C609Y, C609S, C609G, C609R, C609F, C609W, C611R, C611S, C611G, C611Y, C611F, C611W, C618S, C618Y, C618R, C618Y, C618G, C618F, C618W, F619F, C620S, C620W, C620R, C620G, C620L, C620Y, C620F, E623K, D624N, C630A, C630R, C630S, C630Y, C630F, D631N, D631Y, D631A, D631G, D631V, D631E, E632K, E632G, C634W, C634Y, C634S, C634R, C634F, C634G, C634L, C634A, C634T, R635G, T636P, T636M, $A_6$40G, $A_6$41S, $A_6$41T, V648I, S649L, $A_6$64D, H665Q, K666E, K666M, K666N, S686N, G691S, R694Q, M700L, V706M, V706A, E713K, G736R, G748C, $A_7$50P, S765P, P766S, P766M, E768Q, E768D, L769L, R770Q, D771N, N777S, V778I, Q781R, L790F, Y791F, V804L, V804M, V804E, E805K, Y806E, Y806F, Y806S, Y806G, Y806C, E818K, S819I, G823E, Y826M, R833C, P841L, P841P, E843D, R844W, R844Q, R844L, M848T, I852M, A866W, R873W, A876V, L881V, A883F, A883S, A883T, E884K, R886W, S891A, R897Q, D898V, E901K, S904F, S904C, K907E, K907M, R908K, G911D, R912P, R912Q, M918T, M918V, M918L, A919V, E921K, S922P, S922Y, T930M, F961L, R972G, R982C, M1009V, D1017N, V1041G, and M1064T. In another specific embodiment, the point mutation in RET kinase domain is selected from V804L, V804M, V804E, M918T, E805K, Y806C, Y806E, C634Y, and C634W. In another specific embodiment, RET kinase domain mutations further include RET gene fusion. In another specific embodiment, RET gene fusion is selected from BCR-RET, CLIP1-RET, KIF5B-RET, CCDC6-RET, $NCOA_4$-RET, TRIM33-RET, ERC1-RET, ELKS-RET, RET-ELKS, $FGFR_1$OP-RET, RET-MBD1, RET-RAB61P2, RET-PCM1, RET-$PPKAR_1$A, RET-TRIM24, RET-RFG9, RFP-RET, RET-$GOLGA_5$, HOOK3-RET, KTN1-RET, TRIM27-RET, AKAP13-RET, FKBP15-RET, SPECC1L-RET, $TBL1XR_1$/RET, CEP55-RET, CUX1-RET, $KIAA_1$468-RET, $PPKAR_1$A-RET, RFG8/RET, RET/RFG8, H4-RET, ACBD5-RET, PTCex9-RET, MYH13-RET, PIBF1-RET, $KIAA_1$217-RET, and MPRIP-RET; in another specific embodiment, RET gene fusion is selected from KIF5B-RET and CCDC6-RET; in another specific embodiment, point mutation in KIF5B-RET and CCDC6-RET kinase domains is selected from V804L, V804M, V804E, M918T, E805K, Y806C, Y806E, C634Y, and C634W.

TRK

In a specific embodiment, compounds disclosed herein are inhibitors of a Trk kinase, and can be used for treating, preventing or ameliorating diseases or disorders that are modulated or otherwise affected by one or more of wild-type Trk and Trk kinase domain mutants, or one or more symptoms or causes thereof. Such diseases or disorders include, but are not limited to, proliferative conditions (e.g., cancers, including hematological cancers and solid tumors), pain, inflammation, and certain infectious diseases that can be treated, prevented or controlled by modulating various activities of kinases (including dimerization, ligand binding, and phosphotransferase activities) or by modulating the expression of kinases. In a specific embodiment, the cancer may be selected from non-small cell lung cancer, papillary thyroid cancer, glioblastoma multiforme, acute myeloid leukemia, colorectal cancer, large cell neuroendocrine cancer, prostate cancer, colon cancer, acute myeloid leukemia, sarcoma, pediatric glioma, intrahepatic cholangiocarcinoma, hairy cell astrocytoma, low grade glioma, lung adenocarcinoma, salivary gland cancer, secretory breast cancer, fibrosarcoma, nephroma and breast cancer.

In a specific embodiment, the Trk kinase is selected from TrkA, TrkB, and TrkC.

As used herein, the term "Trk kinase domain mutants" refers to one or more mutants of Trk kinase domain, or alternatively, refers to Trk (protein itself becomes the "Trk kinase domain mutant") comprising one or more of the mutations. Mutations in Trk kinase domain can be insertions, deletions, or point mutations. In a specific embodiment, mutations of Trk kinase domain comprise at least one point mutation in the Trk kinase domain. In another specific embodiment, mutations of Trk kinase domain comprise at least one point mutation in the Trk kinase domain. In another specific embodiment, the point mutation in the Trk kinase domain is selected from G595R.

FLT3

In a specific embodiment, compounds disclosed herein are inhibitors of a FLT3 kinase, and can be used for treating, preventing or ameliorating diseases or disorders that are modulated or otherwise affected by one or more of wild-type FLT3, FLT3-ITD, and FLT3 kinase domain mutants, or one or more symptoms or causes thereof. Such diseases or disorders include, but are not limited to, hematological cancers, including acute myeloid leukemia (AML), acute lymphoblastic leukemia (ALL), and myelodysplastic syndrome (MDS), that can be treated, prevented or controlled by modulating various activities of kinases (including dimerization, ligand binding, and phosphotransferase activities) or by modulating the expression of kinases, wherein the method comprises administering a therapeutically or prophylactically effective amount of a compound provided herein to a subject, for example human, in need of such treatment, prevention or control.

As used herein, the term "FLT3 kinase domain mutants" refers to one or more mutants of FLT3 kinase domain, or alternatively, refers to FLT3 (protein itself becomes the "FLT3 kinase domain mutant") comprising one or more of the mutations. Mutations in FLT3 kinase domain can be insertions, deletions, or point mutations. In a specific embodiment, mutations of FLT3 kinase domain comprise at least one point mutation in the FLT3 kinase domain. In another specific embodiment, mutations of FLT3 kinase domain comprise at least one point mutation in the FLT3 kinase domain. In another specific embodiment, the point mutation in FLT3 kinase domain is at position E608, N676, F691, C828, D835, D839, N841, Y842, or M855. In another specific embodiment, the point mutation in the FLT3 kinase domain is selected from E608K, N676D, N676I, N676S, F691I, F691L, C828S, D835Y, D835V, D835H, D835F, D835E, D839G, D839H, N841C, Y842C, Y842H, Y842N, Y842S, and M855T. In another specific embodiment, "FLT3 kinase domain mutants" refers to point mutations at position F691, D835, or Y842, or refers to FLT3 comprising at least one point mutation at those positions. In another specific embodiment, "FLT3 kinase domain mutants" refers to one or more point mutation selected from F691L, D835Y, D835V, D835H, D835F, D835E, Y842C, Y842H, Y842N, and Y842S, or refers to FLT3 comprising at least one of the point mutations. In another specific embodiment, FLT3 kinase domain mutants further comprise one or more additional FLT3-ITD mutants. In another specific embodiment, FLT3 kinase domain mutants further comprise one or more additional FLT3-ITD mutants. However, when FLT3 kinase domain mutants comprise more than one point mutations, additional point mutations or mutations can appears on the same FLT3 receptor, or additional point mutations or mutations can appears on the separate alleles or on different pure lineages of leukemia; in this case, the mutation is polyclonal.

The term "juxtamembrane region" or "juxtamembrane domain" of FLT3 refers to a region of FLT3 that connects transmembrane helices to tyrosine kinase domains.

In another specific embodiment, "wild-type FLT3" refers to FTL3 gene or allele, comprising allelic variants and mutations other than FLT3 kinase domain mutations and FLT3-ITD mutations.

c-KIT

In a specific embodiment, compounds disclosed herein are inhibitors of a c-Kit kinase, and can be used for treating symptoms associated with abnormal c-KIT activities. Activating mutations in c-KIT exist in a variety of indications, including systemic mastocytosis, gastrointestinal stromal tumor, acute myeloid leukemia, melanoma, seminoma, intracranial germ cell tumor, and mediastinal B-cell lymphoma.

In another specific embodiment, compounds disclosed herein can be used for treating one or more c-Kit mutations in exon 17 (e.g., D816V, D816Y, D816F, D816K, D816A, D816G, D820A, D820E, D820G, N822K, N822H, Y823D, and A829P) and have activity on the mutations while having much lower activity on wild-type c-Kit.

In the treatment method of the present disclosure, "effective amount" is intended to refer to an amount or dose sufficient to produce the required therapeutic benefits in individuals in need thereof. The effective amount or dose of the compound of the present disclosure can be determined by conventional methods (e.g., modeling, dose escalation or clinical trials) and conventional factors (e.g., mode or way for drug delivery, pharmacokinetics of a formulation, severity and process of infection, health status and weight of an individual, and judgment of a physician). An exemplary dose is in the range of from about 0.1 mg to 1 g per day, or about 1 mg to 50 mg per day, or about 50 mg to 250 mg per day, or about 250 mg to 1 g per day. The total dose can be a single dose unit or separate dose units (e.g., BID, TID, or QID).

After the patient's disease is improved, the dose can be adjusted for prophylactic or maintenance therapy. For example, the dose or frequency of administration or both can be reduced to an amount that maintains the desired therapeutic or preventive effect depending on symptoms. Of course, if symptoms have been reduced to an appropriate extent, the treatment can be stopped. However, patients may require long-term intermittent treatment if any recurrence of symptoms. Patients may also need long-term slow treatment.

Drug Combination

The compound of the present disclosure can be used in combination with one or more other active ingredients in pharmaceutical compositions or methods to treat the diseases and conditions described herein. Other additional active ingredients include other therapeutic agents or medicines that mitigate adverse effects of the therapeutic agent on the intended disease target. The combination can be used to increase efficacy, improve other disease symptoms, reduce one or more negative effects, or reduce the required dosage of the compound of the present disclosure. The additional active ingredient may be formulated into a pharmaceutical composition separate from the compound of the present invention or may be included in a single pharmaceutical composition with the compound of the present invention. The additional active ingredient may be administered simultaneously with, before, or after the administration of the compound of the present disclosure.

Combination agents include those additional active ingredients that known or observed to be effective in the treatment of the diseases and conditions described herein, including those effectively against another target related to the disease. For example, the compositions and formulations of the present disclosure, and treatment methods may further include other drugs or medicines, such as other active agents that can be used to treat or alleviate the target disease or related symptoms or conditions. For cancer indications, other such agents include, but are not limited to, kinase inhibitors, for example, EGFR inhibitors (such as erlotinib, gefitinib); Raf inhibitors (such as vemurafenib), VEGFR inhibitors (such as sunitinib); standard chemotherapeutic agents such as alkylating agents, antimetabolites, antitumor antibiotics, topoisomerase inhibitors, platinum drugs, mitotic inhibitors, antibodies, hormone therapy or corticosteroids. For pain indications, suitable combination agents include anti-inflammatory agents, such as NSAID. The pharmaceutical composition of the present disclosure may additionally include one or more of the active agents, and the method of treatment may additionally include administering an effective amount of one or more of the active agents.

Example

The present disclosure will be further described below in combination with specific examples. It should be understood that these examples are only used to illustrate the present disclosure and not to limit the scope of the present disclosure. The experimental methods without specific conditions in the following examples generally follow the conventional conditions or the conditions recommended by the manufacturer. Unless otherwise stated, parts and percentages are parts by weight and weight percent.

Generally, in the preparation process, each reaction is carried out in an inert solvent at a temperature from room temperature to reflux temperature (e.g., 0° C. to 100° C., or alternatively 0° C. to 80° C.). The reaction time is usually 0.1-60 hours, or alternatively 0.5-24 hours.

The abbreviations as used herein have the following meanings:

Pd(dppf)Cl$_2$: [1,1'-bis(diphenylphosphino)ferrocene]dichloropalladium
cataCXium A: n-butyldi(1-adamantyl)phosphine
B$_2$pin$_2$: bis(pinacolato)diboron
NBS: N-bromosuccinimide
DMAP: 4-dimethylaminopyridine
HATU: O(7-azabenzotriazol-1-yl)-N,N,N',N'-tetramethyluronium hexafluorophosphate
TEA: triethyl amine
DIEA: N,N-diisopropylethylamine
Na$_2$CO$_3$: Sodium carbonate
CsF: Cesium fluoride
LiOH: lithium hydroxide
HAc: acetic acid
pTSA: p-toluenesulfonic acid
IPA: isopropanol
MeOH: methanol
EtOH: ethanol
H$_2$O: water
DCM: Dichloromethane
DCE: 1,2-dichloroethane
THF: tetrahydrofuran
ACN: acetonitrile
DME: dimethyl ether
DMA: N,N-dimethylacetamide Example 1 Preparation of 1-(2-fluoro-5-(trifluoromethyl)phenyl)-3-(4-(7-(1-methyl-1H-pyrazol-4-yl)imidazo[1,2-b]pyridazin-3-yl)phenyl)urea (Compound T-1)

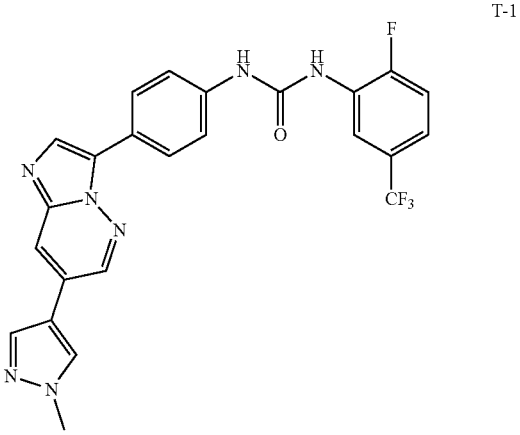 [SMILES: Cn1cc(-c2cnn3c(-c4ccc(NC(=O)Nc5cc(C(F)(F)F)ccc5F)cc4)cnc3c2)cn1]

The following synthetic route was used:

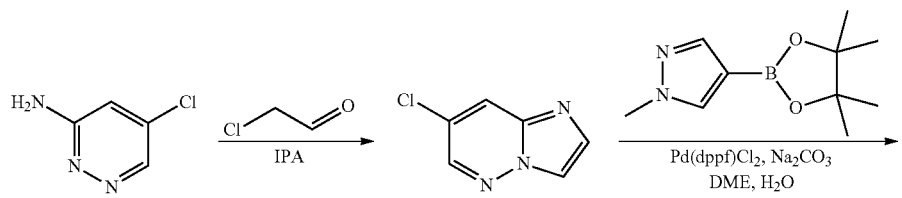

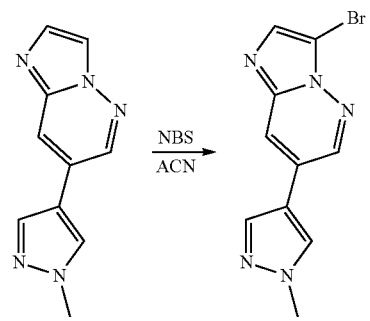

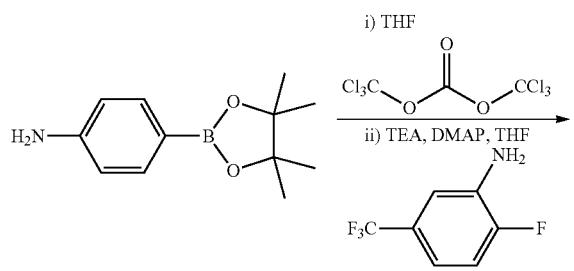

-continued

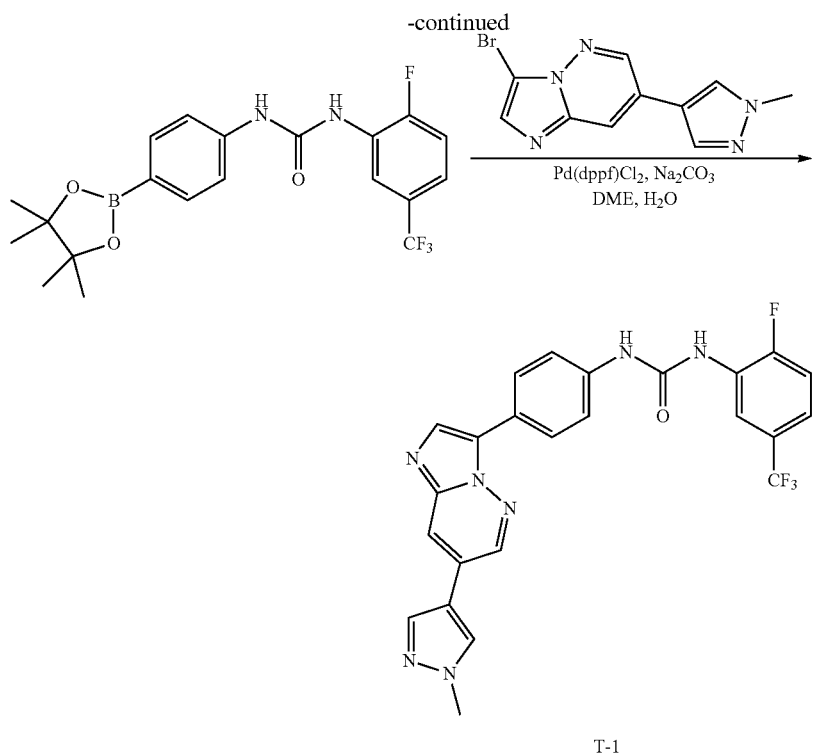

T-1

Step 1: Synthesis of Compound 7-chloroimidazo[1,2-b]pyridazine 5-chloropyridazin-3-amine (0.84 g, 6.5 mmol) and 40% aqueous solution of chloroacetaldehyde (2.55 g, 19.5 mmol) were added in 15 mL isopropanol. The mixture was heated to reflux for 3 hrs. The reaction solution was rotary evaporated to remove the solvent, diluted with 30 mL water, and extracted with EtOAc (20 mL*3). The organic phases were combined, washed with 20 mL saturated brine, dried over anhydrous sodium sulfate, and filtered. The filtrate was concentrated, and separated by silica gel column chromatography to afford a pale yellow solid, 0.79 g, yield: 80%. ESI-MS: 154[M$^+$+1].

Step 2: Synthesis of Compound 7-(1-methyl-1H-pyrazol-4-yl)imidazo[1,2-b]pyridazine 7-chloroimidazo[1,2-b]pyridazine (0.79 g, 5.2 mmol), 1-methyl-4-(4,4,5,5-tetramethyl-1,3,2-dioxaborolan-2-yl)-1H-pyrazole (1.35 g, 6.5 mmol), Pd(dppf)Cl$_2$ (190 mg, 0.26 mmol), and Na$_2$CO$_3$ (1.65 g, 15.6 mmol) were added in 20 mL DME and 5 mL water, and the system was flushed three times with nitrogen. The mixture was heated to 90° C. and reacted overnight. The reaction solution was cooled to room temperature, quenched with 40 ml water, and extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 0.67 g, yield: 65%. ESI-MS: 200[M$^+$+1].

Step 3: Synthesis of Compound 3-bromo-7-(1-methyl-1H-pyrazol-4-yl)imidazo[1,2-b]pyridazine 7-(1-methyl-1H-pyrazol-4-yl)imidazo[1,2-b]pyridazine (0.67 g, 3.4 mmol) was dissolved in 10 mL acetonitrile, and NBS (0.66 g, 3.7 mmol) was added slowly. The mixture was stirred at room temperature for 2 hrs. The reaction solution was rotary evaporated to remove the solvent, diluted with 10 mL water, and extracted with EtOAc (10 mL*3). The organic phase was washed with 10 mL saturated brine, dried over anhydrous sodium sulfate, and filtered. The filtrate was concentrated, and separated by silica gel column chromatography to afford a pale yellow solid, 0.8 g, yield: 85%. ESI-MS: 280[M$^+$+2].

Step 4: Synthesis of Compound 1-(2-fluoro-5-(trifluoromethyl)phenyl)-3-(4-(4,4,5,5-tetramethyl-1,3,2-dioxaborolan-2-yl)phenyl)urea 4-aminophenylboronic acid pinacol ester (0.88 g, 4 mmol) was dissolved in 15 mL tetrahydrofuran, and bis(trichloromethyl) carbonate (0.41 g, 1.4 mmol) was added slowly. The mixture was heated to reflux and reacted for 1 hr. The reaction solution was rotary evaporated to remove the solvent, and dissolved in 20 mL tetrahydrofuran. DMAP (49 mg, 0.4 mmol), triethyl amine (0.81 g, 8 mmol), and 2-fluoro-5-trifluoromethylaniline (0.71 g, 4 mmol) were subsequently added, and the mixture was reacted under reflux overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 0.93 g, yield: 55%. ESI-MS: 425[M$^+$+1].

Step 5: Synthesis of Compound 1-(2-fluoro-5-(trifluoromethyl)phenyl)-3-(4-(7-(1-methyl-1H-pyrazol-4-yl)imidazo[1,2-b]pyridazin-3-yl)phenyl)urea (Compound T-1)

3-bromo-7-(1-methyl-1H-pyrazol-4-yl)imidazo[1,2-b]pyridazine (86 mg, 0.31 mmol), 1-(2-fluoro-5-(trifluoromethyl)phenyl)-3-(4-(4,4,5,5-tetramethyl-1,3,2-dioxaborolan-2-yl)phenyl)urea (156 mg, 0.37 mmol), Pd(dppf)Cl$_2$ (15 mg, 0.02 mmol), and Na$_2$CO$_3$ (131 mg, 1.24 mmol) were added in 12 mL DME and 4 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 100 mg, yield: 66%. ESI-MS: 496[M$^+$+1]. $^1$H NMR (300 MHz, DMSO-d$_6$) δ 9.37 (s, 1H), 8.97 (s, 2H), 8.64 (d, J=7.3 Hz, 1H), 8.40 (d, J=27.0 Hz, 2H), 8.14 (dd, J=21.5, 8.4 Hz, 4H), 7.62 (d, J=8.2 Hz, 2H), 7.49 (d, J=10.2 Hz, 1H), 7.40 (s, 1H), 3.91 (s, 3H).

Example 2 Preparation of 2-(4-(7-(1-methyl-1H-pyrazol-4-yl)imidazo[1,2-b]pyridazin-3-yl)phenyl)-N-(5-(1,1,1-trifluoro-2-methylpropan-2-yl)isoxazol-3-yl)acetamide (Compound T-2)

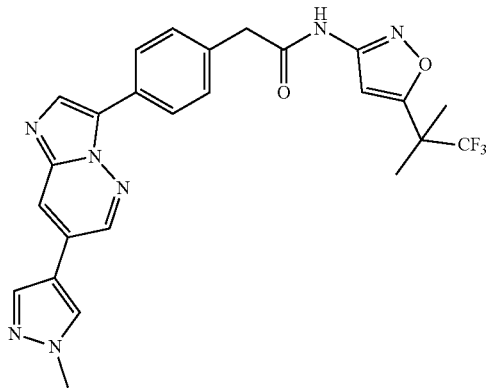

The following synthetic route was used:

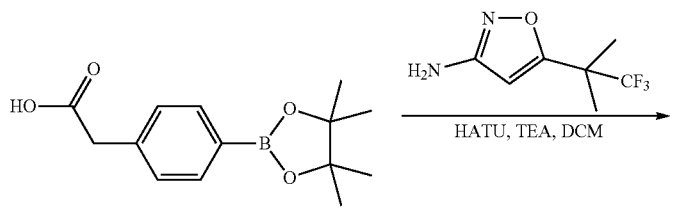

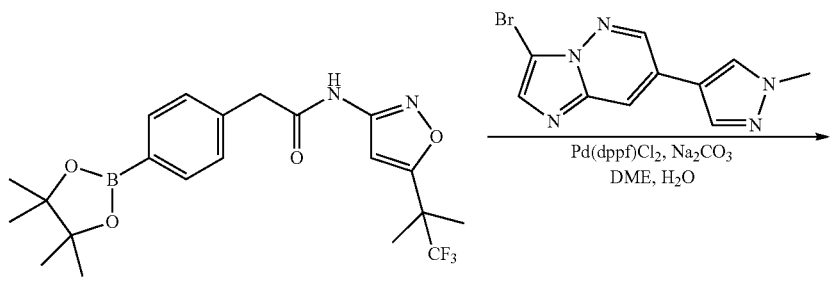

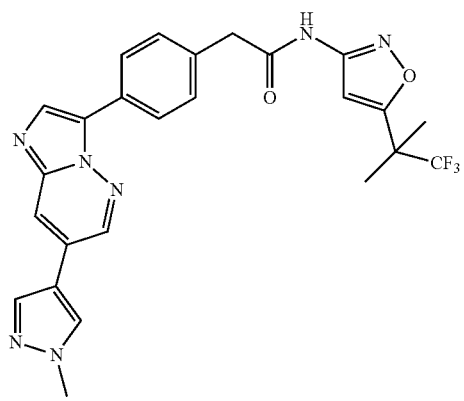

T-2

Step 1: Synthesis of Compound 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide 4-(carboxymethyl)phenylboronic acid pinacol ester (0.94 g, 3.6 mmol), 5-(1,1,1-trifluoro-2-methylpropan-2-yl)isoxazol-3-amine (0.7 g, 3.6 mmol), and triethyl amine (0.73 g, 7.2 mmol) were dissolved in 20 mL dichloromethane, and HATU (2.05 g, 5.4 mmol) was added under an ice bath. The mixture was reacted at room temperature overnight. The reaction solution was diluted with 20 mL dichloromethane, and washed with water. The organic phase was washed with 10 mL saturated brine, dried over anhydrous sodium sulfate, and filtered. The filtrate was concentrated, and separated by silica gel column chromatography to afford a pale yellow solid, 1.1 g, yield: 70%. ESI-MS: 439[M$^+$+1].

Step 2: Synthesis of Compound 2-(4-(7-(1-methyl-1H-pyrazol-4-yl)imidazo[1,2-b]pyridazin-3-yl)phenyl)-N-(5-(1,1,1-trifluoro-2-methylpropan-2-yl)isoxazol-3-yl)acetamide 3-bromo-7-(1-methyl-1H-pyrazol-4-yl)imidazo[1,2-b]pyridazine (83 mg, 0.3 mmol), 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (158 mg, 0.36 mmol), Pd(dppf)Cl$_2$ (15 mg, 0.02 mmol), and Na$_2$CO$_3$ (127 mg, 1.2 mmol) were added in 10 mL DME and 2 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 100 mg, yield: 66%. ESI-MS: 510[M$^+$+1]. $^1$H NMR (400 MHz, DMSO-d$_6$) δ 11.45 (s, 1H), 9.58 (s, 1H), 8.35 (s, 1H), 8.11 (s, 1H), 7.91 (s, 1H), 7.80-7.64 (m, 3H), 7.52 (d, J=7.8 Hz, 2H), 6.93 (s, 1H), 3.90 (s, 3H), 3.78 (s, 2H), 1.54 (s, 6H).

Example 3 Preparation of 2-(6-(7-(1-methyl-1H-pyrazol-4-yl)imidazo[1,2-c]pyrimidin-3-yl)pyridin-3-yl)-N-(5-(1,1,1-trifluoro-2-methylpropan-2-yl)isoxazol-3-yl)acetamide (Compound T-3)

The following synthetic route was used:

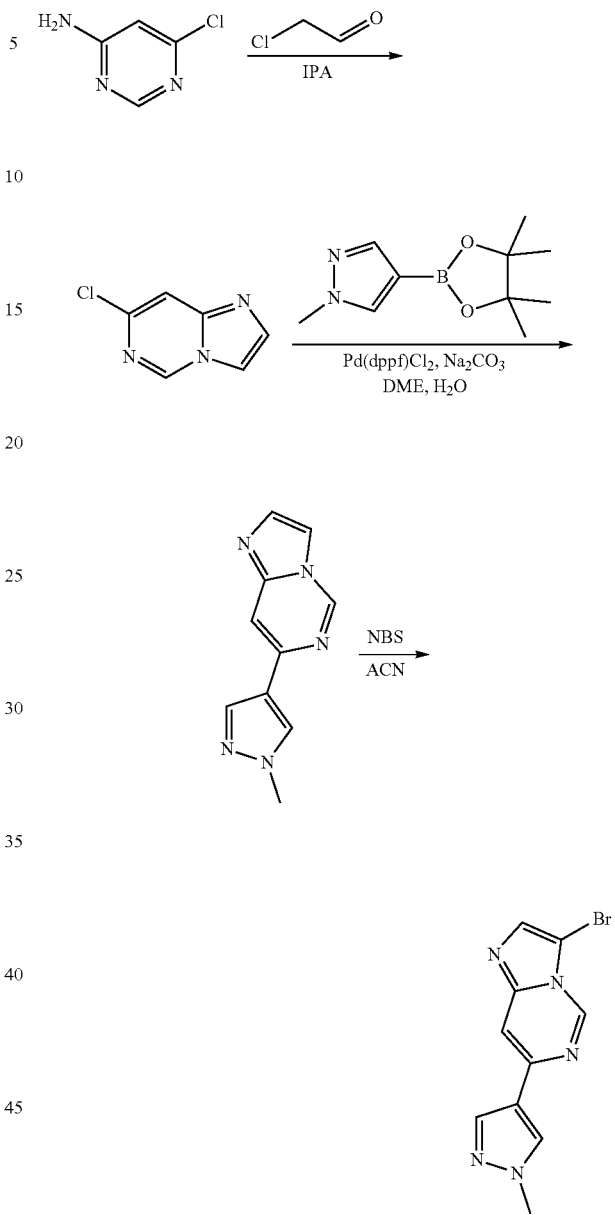

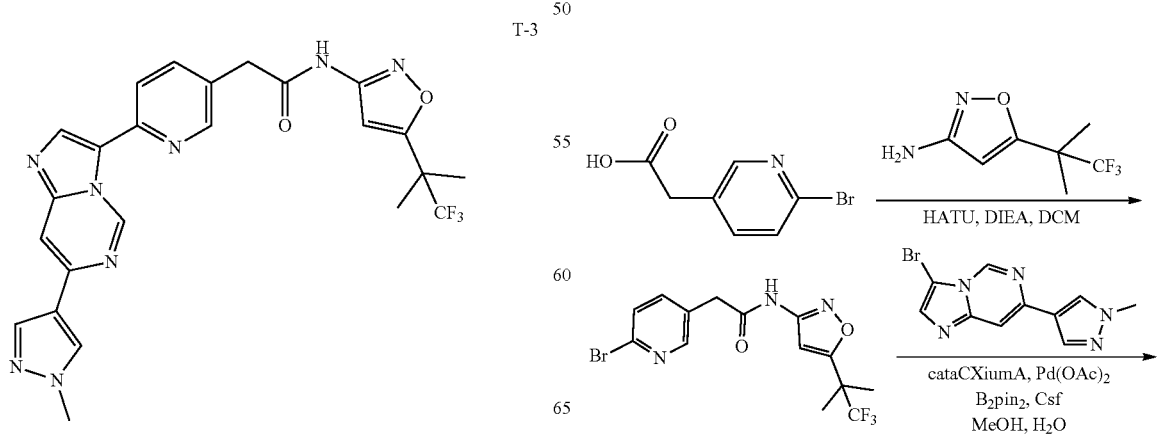

-continued

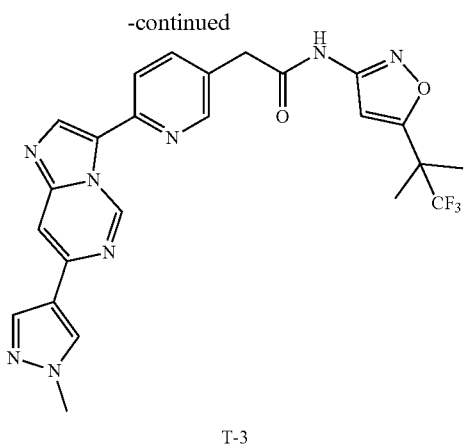

T-3

Step 1: Synthesis of Compound 7-chloroimidazo[1,2-c]pyrimidine 4-amino-6-chloropyrimidine (0.84 g, 6.5 mmol) and 40% aqueous solution of chloroacetaldehyde (2.55 g, 19.5 mmol) were added in 15 mL isopropanol. The mixture was heated to reflux for 3 hrs. The reaction solution was rotary evaporated to remove the solvent, diluted with 30 mL water, and extracted with EtOAc (20 mL*3). The organic phases were combined, washed with 20 mL saturated brine, dried over anhydrous sodium sulfate, and filtered. The filtrate was concentrated, and separated by silica gel column chromatography to afford a pale yellow solid, 0.79 g, yield: 80%. ESI-MS: 154[M$^+$+1].

Step 2: Synthesis of Compound 7-(1-methyl-1H-pyrazol-4-yl)imidazo[1,2-c]pyrimidine 7-chloroimidazo[1,2-c]pyrimidine (0.79 g, 5.2 mmol), 1-methyl-4-(4,4,5,5-tetramethyl-1,3,2-dioxaborolan-2-yl)-1H-pyrazole (1.35 g, 6.5 mmol), Pd(dppf)Cl$_2$ (190 mg, 0.26 mmol), and Na$_2$CO$_3$ (1.65 g, 15.6 mmol) were added in 20 mL DME and 5 mL water, and the system was flushed three times with nitrogen. The mixture was heated to 90° C. and reacted overnight. The reaction solution was cooled to room temperature. 40 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 0.67 g, yield: 65%. ESI-MS: 200[M$^+$+1].

Step 3: Synthesis of Compound 3-bromo-7-(1-methyl-1H-pyrazol-4-yl)imidazo[1,2-c]pyrimidine 7-(1-methyl-1H-pyrazol-4-yl)imidazo[1,2-c]pyrimidine (0.67 g, 3.4 mmol) was dissolved in 10 mL acetonitrile, and NBS (0.66 g, 3.7 mmol) was added slowly. The mixture was stirred at room temperature for 2 hrs. The reaction solution was rotary evaporated to remove the solvent. 10 mL water was added, and the mixture was extracted with EtOAc (10 mL*3). The organic phase was washed with 10 mL saturated brine, dried over anhydrous sodium sulfate, and filtered. The filtrate was concentrated, and separated by silica gel column chromatography to afford a pale yellow solid, 0.8 g, yield: 85%. ESI-MS: 280[M$^+$+2].

Step 4: Synthesis of Compound 2-(6-bromopyridin-3-yl)-N-(5-(1,1,1-trifluoro-2-methylpropan-2-yl)isoxazol-3-yl)acetamide 2-(6-bromopyridin-3-yl)acetic acid (1.02 g, 4.7 mmol), 5-(1,1,1-trifluoro-2-methylpropan-2-yl)isoxazol-3-amine (0.92 g, 4.7 mmol), and DIEA (1.21 g, 9.4 mmol) were dissolved in 20 mL dichloromethane, and HATU (2.66 g, 7 mmol) was added under an ice bath. The mixture was reacted at room temperature overnight. The reaction solution was diluted with 20 mL dichloromethane, and washed with water. The organic phase was washed with 10 mL saturated brine, dried over anhydrous sodium sulfate, and filtered. The filtrate was concentrated, and separated by silica gel column chromatography to afford a pale yellow solid, 1.3 g, yield: 70%. ESI-MS: 393[M$^+$+1].

Step 5: Synthesis of Compound 2-(6-(7-(1-methyl-1H-pyrazol-4-yl)imidazo[1,2-c]pyrimidin-3-yl)pyridin-3-yl)-N-(5-(1,1,1-trifluoro-2-methylpropan-2-yl)isoxazol-3-yl)acetamide (Compound T-3)

3-bromo-7-(1-methyl-1H-pyrazol-4-yl)imidazo[1,2-c]pyrimidine (109 mg, 0.39 mmol), 2-(6-bromopyridin-3-yl)-N-(5-(1,1,1-trifluoro-2-methylpropan-2-yl)isoxazol-3-yl)acetamide (153 mg, 0.39 mmol), B$_2$pin$_2$ (147 mg, 0.58 mmol), Pd(OAc)$_2$ (9 mg, 0.04 mmol), n-butyldi(1-adamantyl)phosphine (29 mg, 0.08 mmol), and cesium fluoride (118 mg, 0.78 mmol) were added in 15 mL methanol and 4 mL water, and the system was flushed three times with nitrogen. The mixture was heated to 60° C. and reacted for 4 hrs. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 60 mg, yield: 30%. ESI-MS: 511[M$^+$+1]. $^1$H NMR (400 MHz, DMSO-d$_6$) δ 11.45 (s, 1H), 9.38 (s, 1H), 8.52 (s, 1H), 8.30 (s, 1H), 7.90 (s, 1H), 7.75 (s, 1H), 7.56 (s, 1H), 7.49 (d, J=7.8 Hz, 2H), 6.96 (s, 1H), 3.90 (s, 3H), 3.78 (s, 2H), 1.54 (s, 6H).

Example 4 Preparation of 2-(4-(7-(1-methyl-1H-pyrazol-4-yl)imidazo[1,2-c]pyrimidin-3-yl)phenyl)-N-(5-(1,1,1-trifluoro-2-methylpropan-2-yl)isoxazol-3-yl)acetamide (Compound T-4)

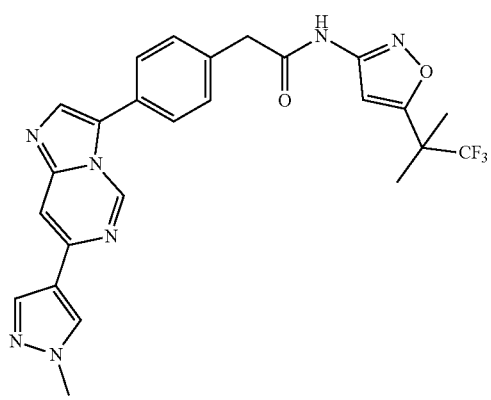

T-4

57

The following synthetic route was used:

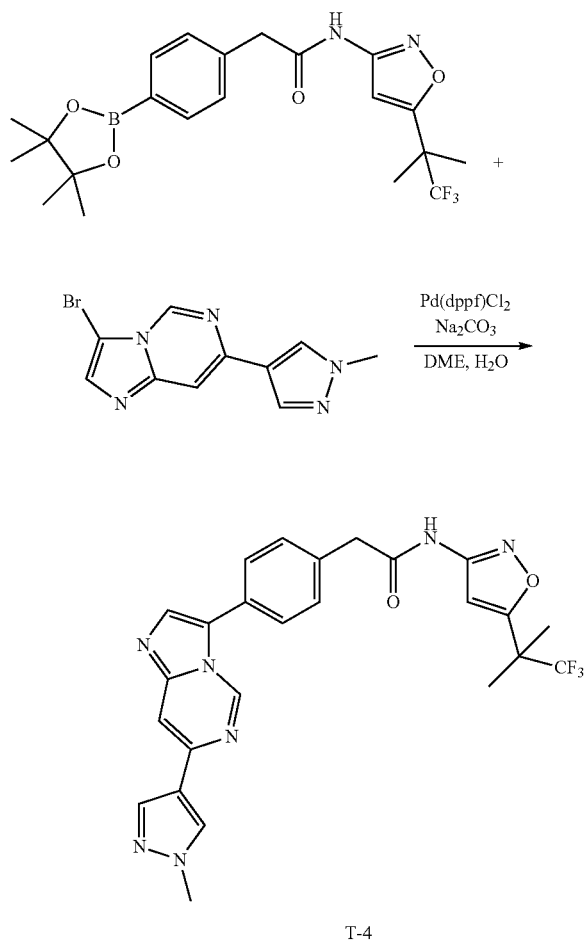

T-4

3-bromo-7-(1-methyl-1H-pyrazol-4-yl)imidazo[1,2-c]pyrimidine (83 mg, 0.3 mmol), 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (158 mg, 0.36 mmol), Pd(dppf)Cl$_2$ (15 mg, 0.02 mmol), and Na$_2$CO$_3$ (127 mg, 1.2 mmol) were added in 10 mL DME and 2 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 100 mg, yield: 65%. ESI-MS: 510[M$^+$+1]. $^1$H NMR (400 MHz, DMSO-d$_6$) δ 11.45 (s, 1H), 9.38 (s, 1H), 8.32 (s, 1H), 8.10 (s, 1H), 7.90 (s, 1H), 7.81-7.68 (m, 3H), 7.49 (d, J=7.8 Hz, 2H), 6.96 (s, 1H), 3.90 (s, 3H), 3.78 (s, 2H), 1.54 (s, 6H).

58

Example 5 Preparation of 2-(4-(8-((1-methyl-1H-pyrazol-4-yl)amino)imidazo[1,2-a]pyrazin-3-yl)phenyl)-N-(5-(1,1,1-trifluoro-2-methylpropan-2-yl)isoxazol-3-yl)acetamide (Compound T-5)

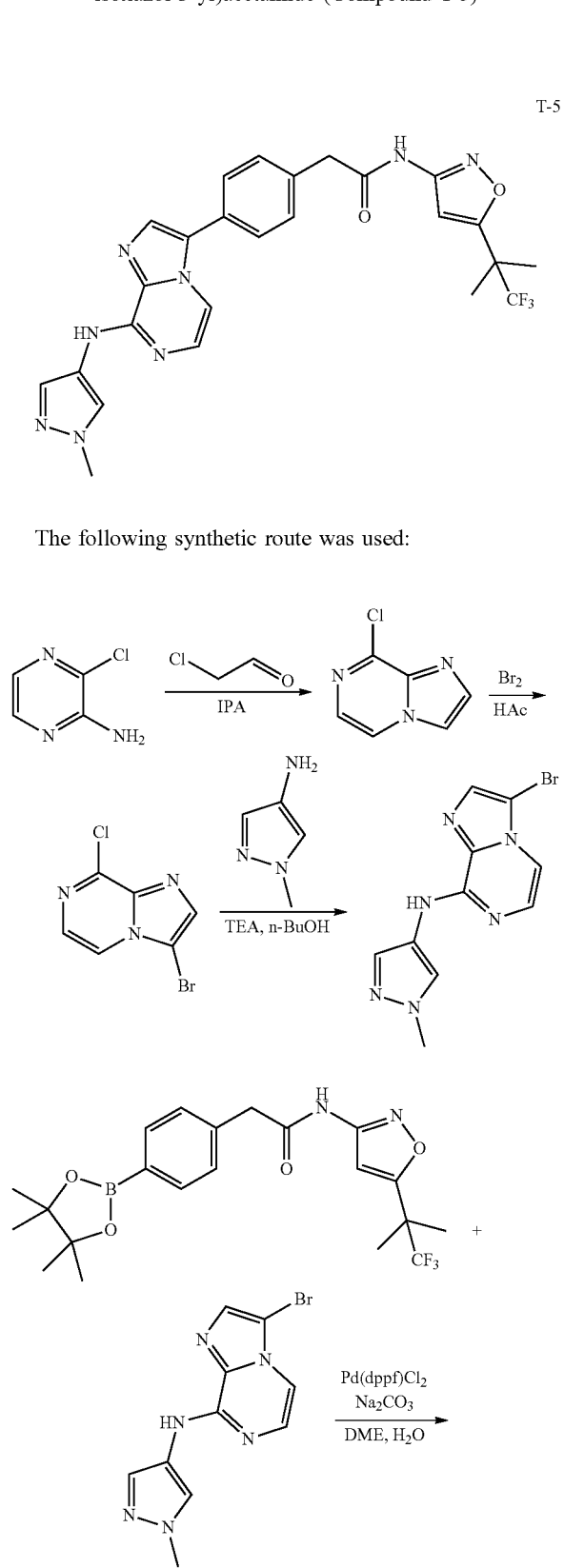

The following synthetic route was used:

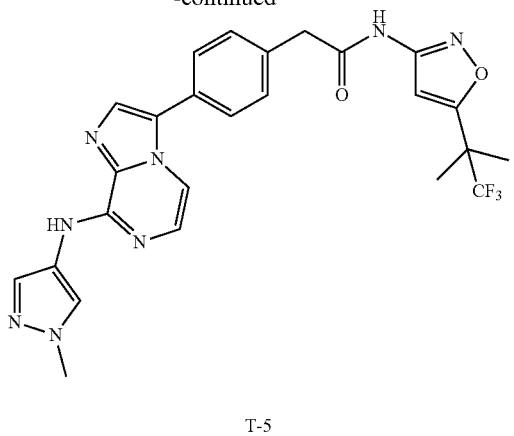

T-5

Step 1: Synthesis of Compound 8-chloroimidazo[1,2-a]pyrazine 3-chloropyrazin-2-amine (1.29 g, 10 mmol) and chloroacetaldehyde (40% aqueous solution, 9.8 g, 50 mmol) were added in 30 mL isopropanol. The mixture was heated to reflux overnight. The reaction solution was rotary evaporated to remove the solvent, and dissolved in 30 mL water. The mixture was adjusted to a pH of 7 with saturated solution of sodium bicarbonate, and extracted with EtOAc (20 mL*3). The organic phases were combined, washed with 20 mL saturated brine, dried over anhydrous sodium sulfate, and filtered. The filtrate was concentrated, and separated by silica gel column chromatography to afford a pale yellow solid, 1.07 g, yield: 70%. ESI-MS: 154[M$^+$+1].

Step 2: Synthesis of Compound 3-bromo-8-chloroimidazo[1,2-a]pyrazine 8-chloroimidazo[1,2-a]pyrazine (1.07 g, 7 mmol) was dissolved in 15 mL glacial acetic acid, and liquid bromine (1.12 g, 7 mmol) was slowly added dropwise under an ice bath. After the addition was completed, the ice bath was removed. The mixture was stirred at RT overnight. TLC detection showed that the reaction was completed. 30 mL saturated solution of sodium sulfite was added, and the mixture was extracted with EtOAc (30 mL*3). The organic phases were combined, washed with 20 mL saturated brine, dried over anhydrous sodium sulfate, and filtered. The filtrate was concentrated, and separated by silica gel column chromatography to afford a pale yellow solid, 1.33 g, yield: 82%. ESI-MS: 234[M$^+$+2].

Step 3: Synthesis of Compound 3-bromo-N-(1-methyl-1H-pyrazol-4-yl)imidazo[1,2-a]pyrazin-8-amine 3-bromo-8-chloroimidazo[1,2-a]pyrazine (1.33 g, 5.7 mmol), 1-methyl-TH-pyrazol-4-amine (0.66 g, 6.8 mmol), and triethyl amine (1.15 g, 11.4 mmol) were added in 15 mL n-butanol. The mixture was heated to 120° C. and reacted overnight. The reaction solution was rotary evaporated to remove the solvent, diluted with 30 mL water, and extracted with EtOAc (20 mL*3). The organic phases were combined, washed with 20 mL saturated brine, dried over anhydrous sodium sulfate, and filtered. The filtrate was concentrated, and separated by silica gel column chromatography to afford a pale yellow solid, 1.25 g, yield: 75%. ESI-MS: 295[M$^+$+2].

Step 4: Synthesis of Compound 2-(4-(8-((1-methyl-1H-pyrazol-4-yl)amino)imidazo[1,2-a]pyrazin-3-yl)phenyl)-N-(5-(1,1,1-trifluoro-2-methylpropan-2-yl)isoxazol-3-yl)acetamide (Compound T-5)

3-bromo-N-(1-methyl-TH-pyrazol-4-yl)imidazo[1,2-a]pyrazin-8-amine (88 mg, 0.3 mmol), 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (158 mg, 0.36 mmol), Pd(dppf)Cl$_2$ (15 mg, 0.02 mmol), and Na$_2$CO$_3$ (127 mg, 1.2 mmol) were added in 10 mL DME and 2 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 94 mg, yield: 60%. ESI-MS: 525[M$^+$+1]. $^1$HNMR (400 MHz, DMSO-d$_6$) δ 11.46 (s, 1H), 9.91 (s, 1H), 8.19 (s, 1H), 8.11 (d, J=8.3 Hz, 2H), 8.02 (s, 1H), 7.94 (s, 1H), 7.65 (s, 1H), 7.57 (s, 1H), 7.43 (d, J=8.2 Hz, 2H), 6.96 (s, 1H), 3.83 (s, 3H), 3.79 (s, 2H), 1.53 (s, 1H).

Example 6 Preparation of 2-(4-(8-((1-methyl-1H-pyrazol-4-yl)amino)imidazo[1,2-b]pyridazin-3-yl)phenyl)-N-(5-(1,1,1-trifluoro-2-methylpropan-2-yl)isoxazol-3-yl)acetamide (Compound T-6)

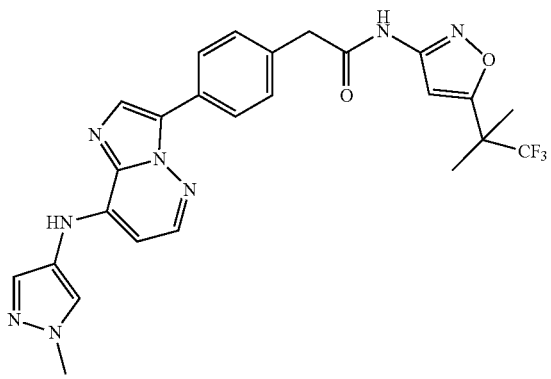

T-6

The following synthetic route was used:

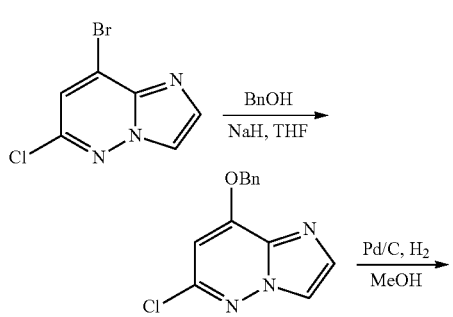

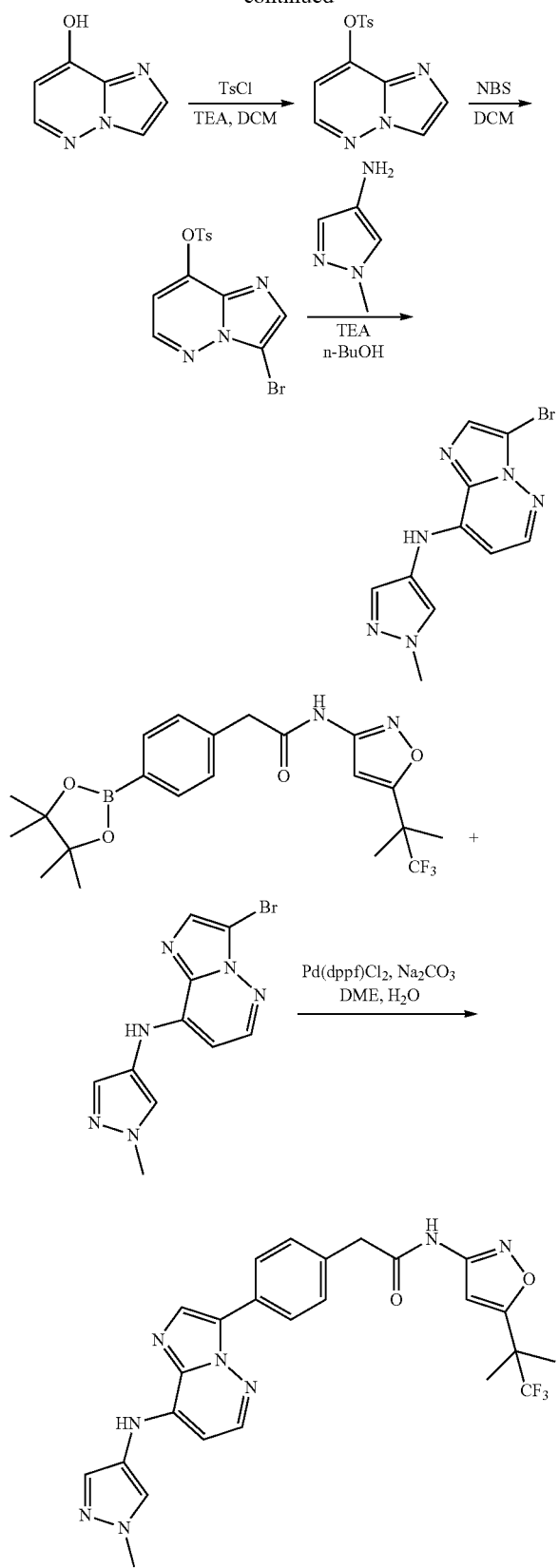

T-6

Step 1: Synthesis of Compound 8-(benzyloxy)-6-chloroimidazo[1,2-b]pyridazine

Benzyl alcohol (1.2 g, 11 mmol) was dissolved in 20 mL tetrahydrofuran, and sodium hydride (60%, dispersed in liquid paraffin, 0.44 g, 11 mmol) was added under an ice bath. The mixture was stirred at RT for half an hour. 8-bromo-6-chloroimidazo[1,2-b]pyridazine (2.32 g, 10 mmol) was slowly added under an ice bath. The ice bath was removed. The mixture was reacted at room temperature overnight. TLC detection showed that the reaction was completed. The reaction solution was diluted with 30 mL water. The mixture was extracted with EtOAc (20 mL*3). The organic phases were combined, washed with 20 mL saturated brine, dried over anhydrous sodium sulfate, and filtered. The filtrate was concentrated, and separated by silica gel column chromatography to afford a pale yellow solid, 2.24 g, yield: 86.5%. ESI-MS: 260[M$^+$+1].

Step 2: Synthesis of Compound Imidazo[1,2-B]Pyridazin-8-Ol 8-(benzyloxy)-6-chloroimidazo[1,2-b]pyridazine (2.24 g, 8.6 mmol) was dissolved in 20 mL methanol, and 200 mg of 10% Pd/C was added. The system was flushed three times with hydrogen. The mixture was stirred at RT under 1 atm hydrogen atmosphere overnight. After the reaction was completed, the Pd/C was filtered off. The filtrate was concentrated, and dried to afford a white solid, 1.05 g, yield: 90%. ESI-MS: 136[M$^+$+1].

Step 3: Synthesis of Compound Imidazo[1,2-b]Pyridazin-8-Yl 4-Methylbenzenesulfonate Imidazo[1,2-b]pyridazin-8-ol (1.05 g, 7.8 mmol) and triethyl amine (1.58 g, 15.6 mmol) were added in 20 mL dichloromethane, and 4-methylbenzenesulfonyl chloride (1.8 g, 9.4 mmol) was added under an ice bath. The reaction was reacted at RT for 2 hrs. TLC detection showed that the reaction was completed. The reaction solution was washed respectively with 20 mL water and 10 mL saturated brine, dried over anhydrous sodium sulfate, and filtered. The filtrate was concentrated, and separated by silica gel column chromatography to afford a white solid, 2.06 g, yield: 92%. ESI-MS: 290[M$^+$+1].

Step 4: Synthesis of Compound 3-Bromoimidazo[1,2-b]Pyridazin-8-Yl 4-Methylbenzenesulfonate Imidazo[1,2-b]pyridazin-8-yl 4-methylbenzenesulfonate (2.06 g, 7.1 mmol) was dissolved in 20 mL dichloromethane, and NBS (1.34 g, 7.5 mmol) was added under an ice bath. The mixture was reacted at RT for 2 hrs. TLC detection showed that the reaction was completed. The reaction solution was washed with 20 mL water, dried over anhydrous sodium sulfate, and filtered. The filtrate was concentrated, and separated by silica gel column chromatography to afford a pale yellow solid, 2.1 g, yield: 80%. ESI-MS: 370[M$^+$+2].

Step 5: Synthesis of Compound 3-bromo-N-(1-methyl-1H-pyrazol-4-yl)imidazo[1,2-b]pyridazin-8-amine 3-Bromoimidazo[1,2-b]pyridazin-8-yl 4-methylbenzenesulfonate (2.1 g, 5.7 mmol), 1-methyl-1H-pyrazol-4-amine (0.66 g, 6.8 mmol), and triethyl amine (1.15 g, 11.4 mmol) were added in 15 mL n-butanol. The mixture was heated to 120° C. and reacted overnight. The reaction solution was rotary evaporated to remove the solvent, diluted with 30 mL water, and extracted with EtOAc (20 mL*3). The organic phases were combined, washed with 20 mL saturated brine, dried over anhydrous sodium sulfate, and filtered. The filtrate was concentrated, and separated by silica gel column chromatography to afford a pale yellow solid, 1.25 g, yield: 75%. ESI-MS: 295[M$^+$+2].

Step 6: Synthesis of Compound 2-(4-(8-((1-methyl-1H-pyrazol-4-yl)amino)imidazo[1,2-b]pyridazin-3-yl)phenyl)-N-(5-(1,1,1-trifluoro-2-methylpropan-2-yl)isoxazol-3-yl)acetamide (Compound T-6)

3-Bromo-N-(1-methyl-1H-pyrazol-4-yl)imidazo[1,2-b]pyridazin-8-amine (88 mg, 0.3 mmol), 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (158 mg, 0.36 mmol), Pd(dppf)Cl$_2$ (15 mg, 0.02 mmol), and Na$_2$CO$_3$ (127 mg, 1.2 mmol) were added in 10 mL DME and 2 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 86 mg, yield: 55%. ESI-MS: 525[M$^+$+1]. $^1$HNMR (400 MHz, DMSO-d$_6$) δ 11.42 (s, 1H), 9.32 (s, 1H), 8.19 (d, J=5.6 Hz, 1H), 8.10 (d, J=8.3 Hz, 2H), 8.01 (s, 1H), 7.92 (s, 1H), 7.58 (s, 1H), 7.43 (d, J=8.2 Hz, 2H), 6.95 (s, 1H), 6.37 (d, J=5.6 Hz, 1H), 3.85 (s, 3H), 3.74 (s, 2H), 1.53 (s, 6H).

Example 7 Preparation of 2-(2-fluoro-4-(7-(1-methyl-1H-pyrazol-4-yl)imidazo[1,2-b]pyridazin-3-yl)phenyl)-N-(5-(1,1,1-trifluoro-2-methylpropan-2-yl)isoxazol-3-yl)acetamide (Compound T-7)

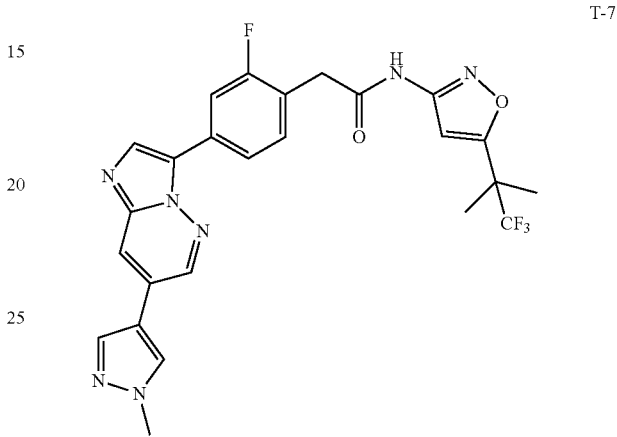

T-7

The following synthetic route was used:

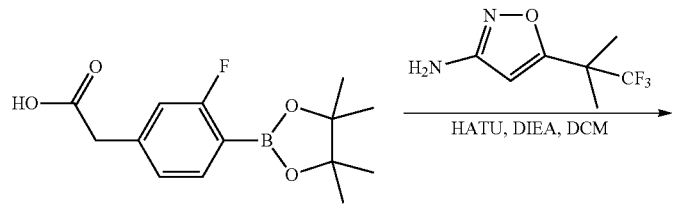

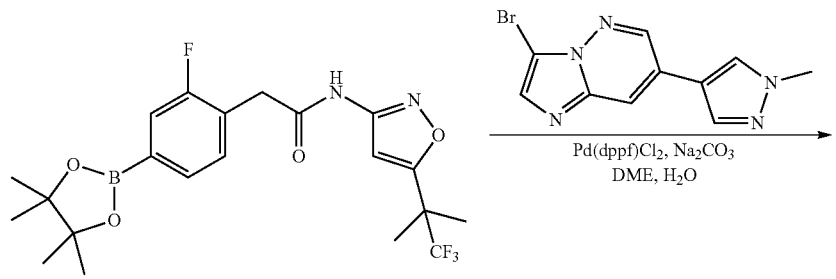

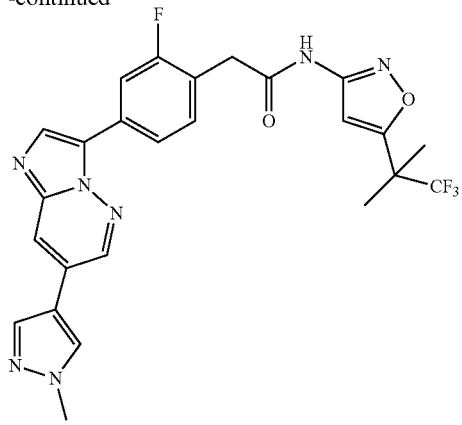

T-7

Step 1: Synthesis of Compound 2-(2-Fluoro-4-(4,4,5,5-Tetramethyl-1,3,2-Dioxaborolan-2-Yl)Phenyl)-N-(5-(1,1,1-Trifluoro-2-M ethylpropan-2-Yl)Isoxazol-3-Yl)Acetamide 2-(3-fluoro-4-(4,4,5,5-tetramethyl-1,3,2-dioxaborolan-2-yl)phenyl)acetic acid (0.94 g, 3.6 mmol), 5-(1,1,1-trifluoro-2-methylpropan-2-yl)isoxazol-3-amine (0.7 g, 3.6 mmol), and triethyl amine (0.73 g, 7.2 mmol) were dissolved in 20 mL dichloromethane, and HATU (2.05 g, 5.4 mmol) was added under an ice bath. The mixture was reacted at room temperature overnight. The reaction solution was diluted with 20 mL dichloromethane, and washed with water. The organic phase was washed with 10 mL saturated brine, dried over anhydrous sodium sulfate, and filtered. The filtrate was concentrated, and separated by silica gel column chromatography to afford a pale yellow solid, 1.1 g, yield: 70%. ESI-MS: 457[M⁺+1].

Step 2: Synthesis of Compound 2-(2-fluoro-4-(7-(1-methyl-1H-pyrazol-4-yl)imidazo[1,2-b]pyridazin-3-yl)phenyl)-N-(5-(1,1,1-trifluoro-2-methylpropan-2-yl)isoxazol-3-yl)acetamide (Compound T-7)

3-bromo-7-(1-methyl-1H-pyrazol-4-yl)imidazo[1,2-b]pyridazine (83 mg, 0.3 mmol), 2-(2-fluoro-4-(4,4,5,5-tetramethyl-1,3,2-dioxaborolan-2-yl)phenyl)-N-(5-(1,1,1-trifluoro-2-m ethylpropan-2-yl)isoxazol-3-yl)acetamide (164 mg, 0.36 mmol), Pd(dppf)Cl₂ (15 mg, 0.02 mmol), and Na₂CO₃ (127 mg, 1.2 mmol) were added in 10 mL DME and 2 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 95 mg, yield: 60%. ESI-MS: 528[M⁺+1]. ¹H NMR (400 MHz, DMSO-d₆) δ 11.46 (s, 1H), 9.04 (s, 1H), 8.46 (s, 1H), 8.39 (s, 1H), 8.31 (s, 1H), 8.20 (s, 1H), 8.06 (d, J=11.6 Hz, 1H), 7.96 (d, J=7.9 Hz, 1H), 7.51 (s, 1H), 6.96 (s, 1H), 3.91 (s, 3H), 3.85 (s, 2H), 1.54 (s, 6H).

Example 8 Preparation of 2-(2-fluoro-4-(7-(1-methyl-1H-pyrazol-4-yl)imidazo[1,2-c]pyrimidin-3-yl)phenyl)-N-(5-(1,1,1-trifluoro-2-methylpropan-2-yl)isoxazol-3-yl)acetamide (Compound T-8)

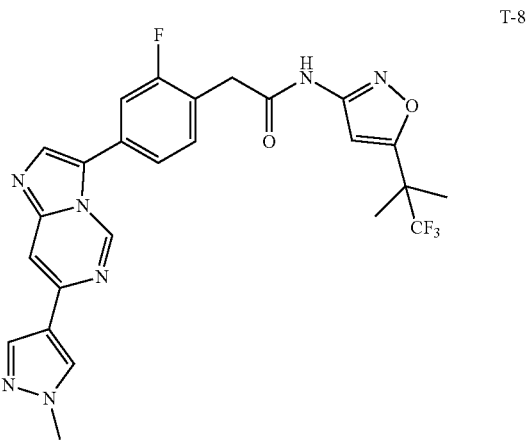 [SMILES: Cn1cc(-c2cnn3c(-c4ccc(CC(=O)Nc5cc(C(C)(C)C(F)(F)F)on5)c(F)c4)cnc3c2)cn1]

T-8

The following synthetic route was used:

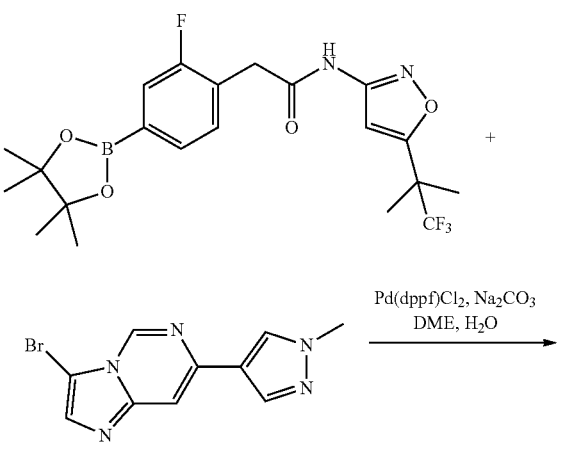

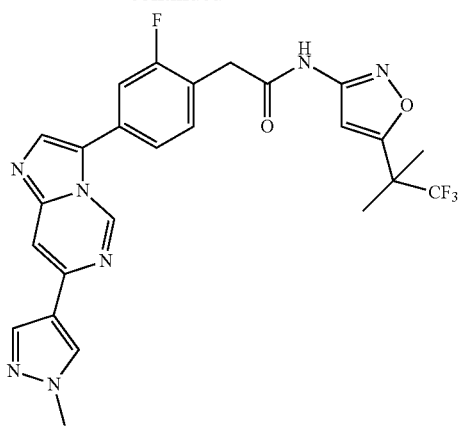

T-8

3-bromo-7-(1-methyl-1H-pyrazol-4-yl)imidazo[1,2-c]pyrimidine (83 mg, 0.3 mmol), 2-(2-fluoro-4-(4,4,5,5-tetramethyl-1,3,2-dioxaborolan-2-yl)phenyl)-N-(5-(1,1,1-trifluoro-2-m ethylpropan-2-yl)isoxazol-3-yl)acetamide (164 mg, 0.36 mmol), Pd(dppf)Cl$_2$ (15 mg, 0.02 mmol), and Na$_2$CO$_3$ (127 mg, 1.2 mmol) were added in 10 mL DME and 2 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 90 mg, yield: 57%. ESI-MS: 528[M$^+$+1]. $^1$H NMR (400 MHz, DMSO-d$_6$) δ 11.46 (s, 1H), 9.24 (s, 1H), 8.52 (s, 1H), 8.38 (s, 1H), 8.30 (s, 1H), 8.21 (s, 1H), 8.05 (d, J=11.6 Hz, 1H), 7.91 (d, J=7.9 Hz, 1H), 7.54 (s, 1H), 6.96 (s, 1H), 3.90 (s, 3H), 3.84 (s, 2H), 1.54 (s, 6H).

Example 9 Preparation of 2-(6-(7-(1-methyl-1H-pyrazol-4-yl)imidazo[1,2-b]pyridazin-3-yl)pyridin-3-yl)-N-(5-(1,1,1-trifluoro-2-methylpropan-2-yl)isoxazol-3-yl)acetamide (Compound T-9)

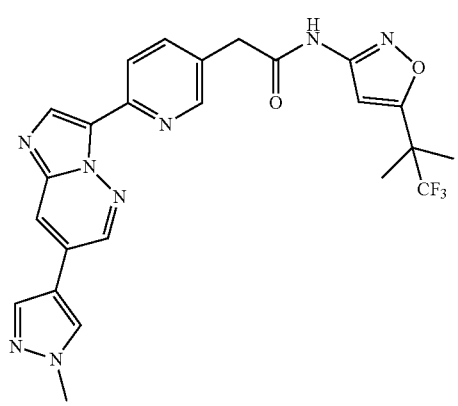

T-9

The following synthetic route was used:

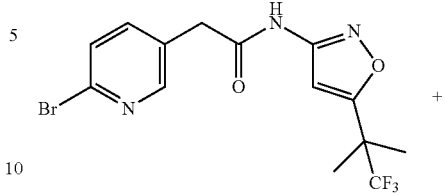

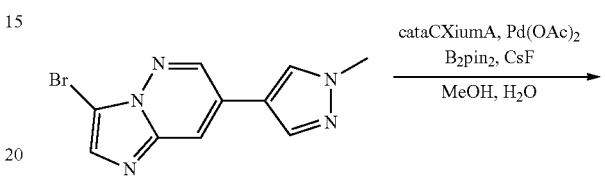

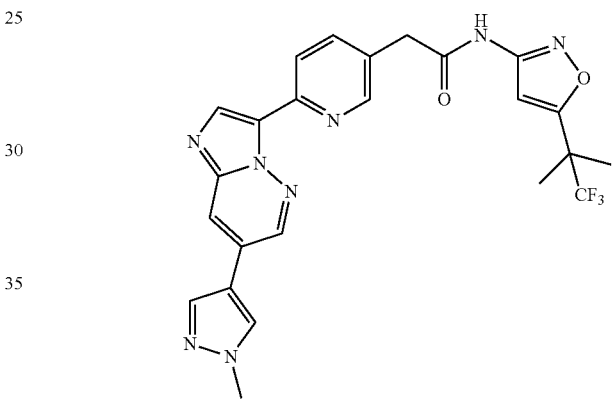

T-9

3-bromo-7-(1-methyl-1H-pyrazol-4-yl)imidazo[1,2-b]pyridazine (109 mg, 0.39 mmol), 2-(6-bromopyridin-3-yl)-N-(5-(1,1,1-trifluoro-2-methylpropan-2-yl)isoxazol-3-yl)acetamide (153 mg, 0.39 mmol), B$_2$pin$_2$ (147 mg, 0.58 mmol), Pd(OAc)$_2$ (9 mg, 0.04 mmol), n-butyldi(1-adamantyl)phosphine (29 mg, 0.08 mmol), and cesium fluoride (118 mg, 0.78 mmol) were added in 15 mL methanol and 4 mL water, and the system was flushed three times with nitrogen. The mixture was heated to 60° C. and reacted for 4 hrs. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 55 mg, yield: 27%. ESI-MS: 511[M$^+$+1]. $^1$H NMR (400 MHz, DMSO-d$_6$) δ 11.45 (s, 1H), 9.42 (s, 1H), 8.50 (s, 1H), 8.31 (s, 1H), 7.92 (s, 1H), 7.76 (s, 1H), 7.53 (s, 1H), 7.44 (d, J=7.8 Hz, 2H), 6.95 (s, 1H), 3.91 (s, 3H), 3.79 (s, 2H), 1.54 (s, 6H).

Example 10 Preparation of 2-(4-(6-(1-methyl-1H-pyrazol-4-yl)pyrazolo[1,5-a]pyrimidin-3-yl)phenyl)-N-(5-(1,1,1-trifluoro-2-methylpropan-2-yl)isoxazol-3-yl)acetamide (Compound T-10)

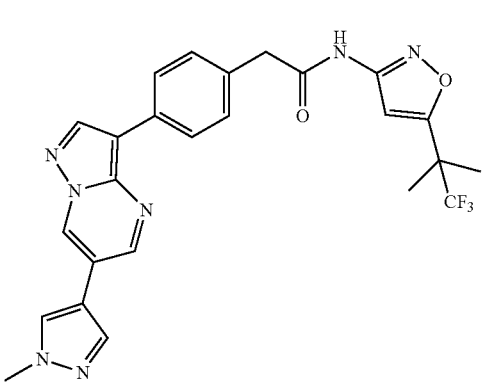

T-10

The following synthetic route was used:

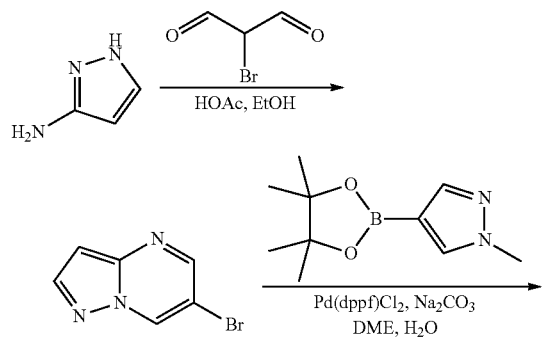

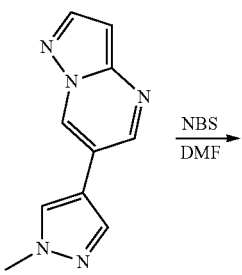

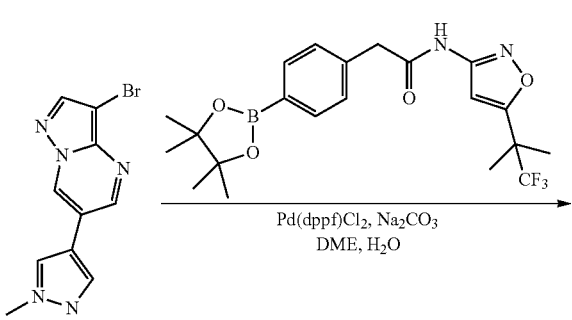

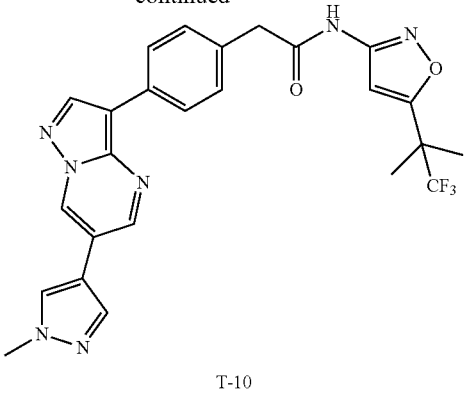

T-10

Step 1: Synthesis of Compound 6-bromopyrazolo[1,5-a]pyrimidine 1H-pyrazol-3-amine (0.63 g, 7.6 mmol) and 2-bromopropanedial (1.15 g, 7.6 mmol) were added in 15 mL absolute ethanol and 5 mL glacial acetic acid. The reaction was reacted at 80° C. for 2 hrs. The reaction solution was rotary evaporated to remove the solvent, diluted with 40 mL water, and extracted with EtOAc (30 mL*3). The organic phase was washed respectively with saturated solution of sodium bicarbonate (30 mL), and saturated brine (30 mL), dried over anhydrous sodium sulfate, and filtered. The filtrate was concentrated, and separated by silica gel column chromatography to afford a pale yellow solid, 1.05 g, yield: 70%. ESI-MS: 200[M$^+$+2].

Step 2: Synthesis of Compound 6-(1-methyl-1H-pyrazol-4-yl)pyrazolo[1,5-a]pyrimidine 6-bromopyrazolo[1,5-a]pyrimidine (1.03 g, 5.2 mmol), 1-methyl-4-(4,4,5,5-tetramethyl-1,3,2-dioxaborolan-2-yl)-1H-pyrazole (1.35 g, 6.5 mmol), Pd(dppf)Cl$_2$ (190 mg, 0.26 mmol), and Na$_2$CO$_3$ (1.65 g, 15.6 mmol) were added in 20 mL DME and 5 mL water, and the system was flushed three times with nitrogen. The mixture was heated to 90° C. and reacted overnight. The reaction solution was cooled to room temperature, quenched with 40 ml water, and extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 0.67 g, yield: 65%. ESI-MS: 200[M$^+$+1].

Step 3: Synthesis of Compound 3-bromo-6-(1-methyl-1H-pyrazol-4-yl)pyrazolo[1,5-a]pyrimidine 6-(1-methyl-1H-pyrazol-4-yl)pyrazolo[1,5-a]pyrimidine (0.67 g, 3.4 mmol) was dissolved in 10 mL acetonitrile, and NBS (0.66 g, 3.7 mmol) was added slowly. The mixture was stirred at room temperature for 2 hrs. The reaction solution was rotary evaporated to remove the solvent, diluted with 10 mL water, and extracted with EtOAc (10 mL*3). The organic phase was washed with 10 mL saturated brine, dried over anhydrous sodium sulfate, and filtered. The filtrate was concentrated, and separated by silica gel column chromatography to afford a pale yellow solid, 0.8 g, yield: 85%. ESI-MS: 280[M$^+$+2].

Step 4: Synthesis of Compound 2-(4-(6-(1-methyl-1H-pyrazol-4-yl)pyrazolo[1,5-a]pyrimidin-3-yl)phenyl)-N-(5-(1,1,1-trifluoro-2-methylpropan-2-yl)isoxazol-3-yl)acetamide (Compound T-10)

3-bromo-6-(1-methyl-1H-pyrazol-4-yl)pyrazolo[1,5-a]pyrimidine (86 mg, 0.31 mmol), 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (158 mg, 0.36 mmol), Pd(dppf)Cl$_2$ (15 mg, 0.02 mmol), and Na$_2$CO$_3$ (131 mg, 1.24 mmol) were added in 12 mL DME and 4 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 100 mg, yield: 63%. ESI-MS: 510[M$^+$+1]. $^1$H NMR (400 MHz, DMSO-d$_6$) δ 11.45 (s, 1H), 9.58 (s, 1H), 9.12 (s, 1H), 8.45 (s, 1H), 7.90 (s, 1H), 7.80-7.64 (m, 3H), 7.50 (d, J=7.8 Hz, 2H), 6.94 (s, 1H), 3.90 (s, 3H), 3.78 (s, 2H), 1.54 (s, 6H).

Example 11 Preparation of 2-(4-(6-(1-methyl-1H-pyrazol-4-yl)pyrazolo[1,5-a]pyridin-3-yl)phenyl)-N-(5-(1,1,1-trifluoro-2-methylpropan-2-yl)isoxazol-3-yl)acetamide (Compound T-11)

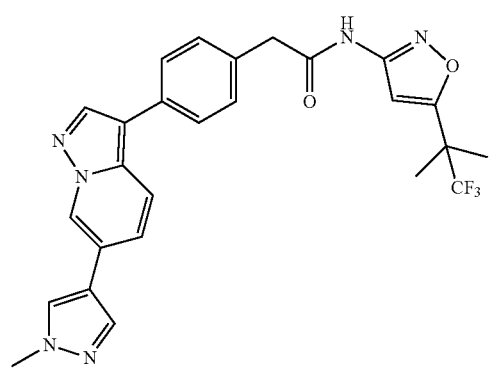

T-11

The following synthetic route was used:

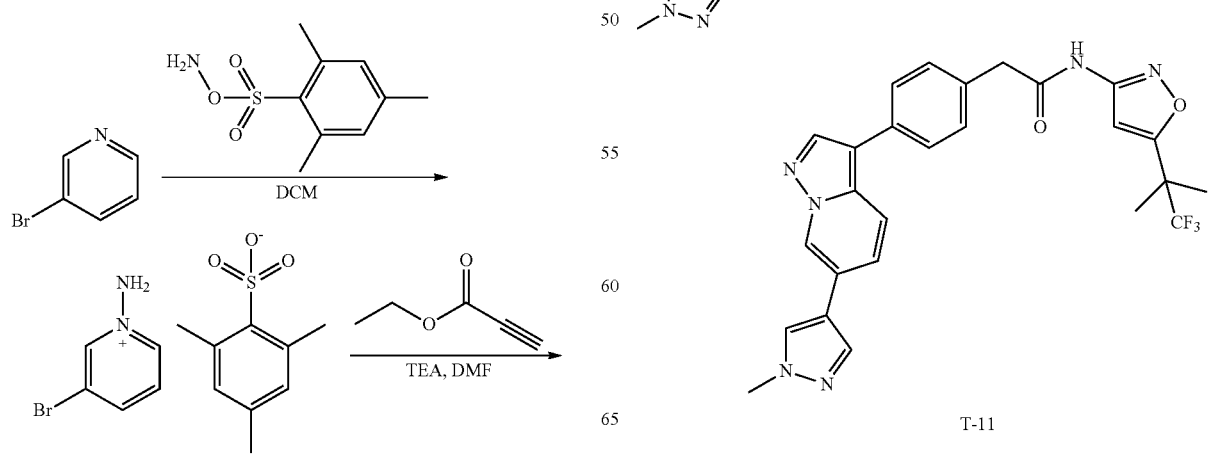

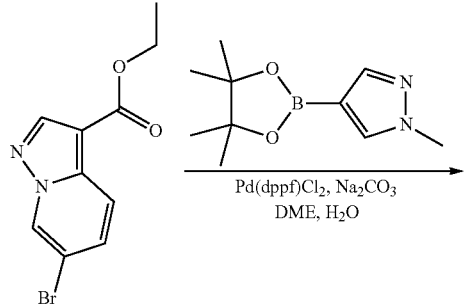

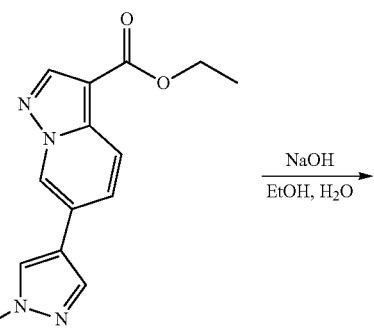

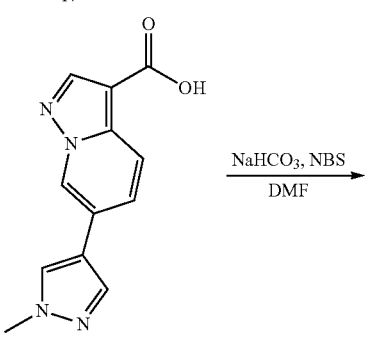

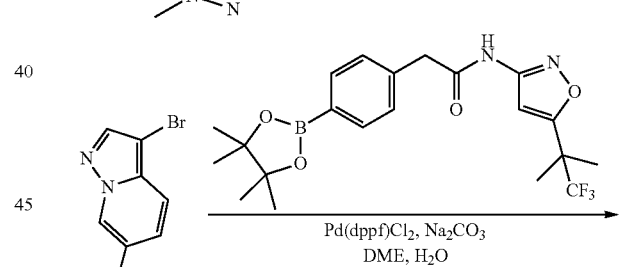

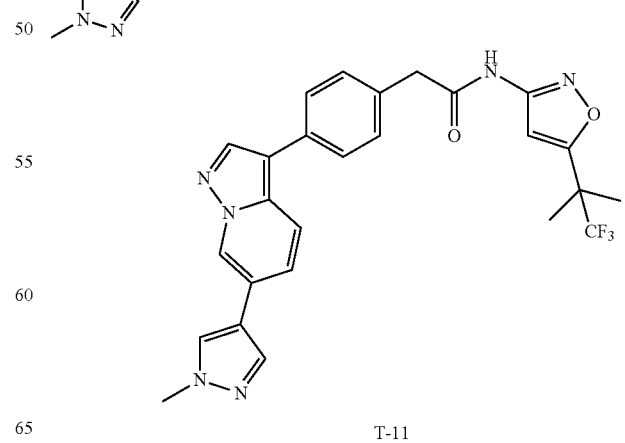

T-11

Step 1: Synthesis of Compound 1-amino-3-bromopyridin-1-ium 2,4,6-trimethylbenzenesulfonate O-(2,4,6-trimethylbenzenesulfonyl)-hydroxylamine (10.8 g, 50 mmol) was dissolved in 100 mL dichloromethane, and 3-bromopyridine (8.69 g, 55 mmol) was slowly added dropwise under an ice bath. After the addition was completed, the mixture was reacted at RT for 2 hrs, during which a white solid gradually precipitated out. 200 mL methyl tert-butyl ether was added. The mixture was further stirred for 20 min, and then filtered. The filter cake was washed with 100 mL methyl tert-butyl ether. The solid was placed into vacuum oven and dried at 55° C. for 4 hrs to afford a white solid, 15 g, yield: 80%.

Step 2: Synthesis of Compound ethyl 6-bromopyrazolo[1,5-a]pyridin-3-formate 1-amino-3-bromopyridin-1-ium 2,4,6-trimethylbenzenesulfonate (15 g, 40 mmol) was dissolved in 60 mL anhydrous DMF and triethyl amine (8.08 g, 80 mmol), and ethyl propiolate (7.8 g, 80 mmol) was slowly added dropwise under an ice bath. After the addition was completed, the ice bath was removed. The mixture was stirred at RT for 48 hrs. The reaction solution was diluted with 200 mL water, and extracted with EtOAc (60 mL*3). The organic phase was washed with 10 mL saturated brine, dried over anhydrous sodium sulfate, and filtered. The filtrate was concentrated, and separated by silica gel column chromatography to afford a pale yellow solid, 2.4 g, yield: 22%. ESI-MS: 271[M$^+$+2].

Step 3: Synthesis of Compound ethyl 6-(1-methyl-1H-pyrazol-4-yl)pyrazolo[1,5-a]pyridin-3-formate Ethyl 6-bromopyrazolo[1,5-a]pyridin-3-formate (1.4 g, 5.2 mmol), 1-methyl-4-(4,4,5,5-tetramethyl-1,3,2-dioxaborolan-2-yl)-1H-pyrazole (1.35 g, 6.5 mmol), Pd(dppf)Cl$_2$ (190 mg, 0.26 mmol), and Na$_2$CO$_3$ (1.65 g, 15.6 mmol) were added in 20 mL DME and 5 mL water, and the system was flushed three times with nitrogen. The mixture was heated to 90° C. and reacted overnight. The reaction solution was cooled to room temperature, quenched with 40 ml water, and extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 1.02 g, yield: 73%. ESI-MS: 271[M$^+$+1].

Step 4: Synthesis of Compound 6-(1-methyl-1H-pyrazol-4-yl)pyrazolo[1,5-a]pyridin-3-formic acid Ethyl 6-(1-methyl-1H-pyrazol-4-yl)pyrazolo[1,5-a]pyridin-3-formate (1.02 g, 3.8 mmol) was dissolved in 20 mL ethanol and 10 mL water, and sodium hydroxide (0.38 g, 9.5 mmol) was added. The mixture was reacted at 80° C. for 2 hrs. The reaction solution was diluted with 30 mL water, adjusted to a pH of 3-4 with TN hydrochloric acid, and extracted with EtOAc (30 mL*3). The organic phase was washed with 20 mL saturated brine, dried over anhydrous sodium sulfate, and filtered. The filtrate was concentrated, and separated by silica gel column chromatography to afford a pale yellow solid, 0.82 g, yield: 90%. ESI-MS: 243[M$^+$+1].

Step 5: Synthesis of Compound 3-bromo-6-(1-methyl-TH-pyrazol-4-yl)pyrazolo[1,5-a]pyridine 6-(1-methyl-TH-pyrazol-4-yl)pyrazolo[1,5-a]pyridin-3-formic acid (0.82 g, 3.4 mmol) and sodium bicarbonate (0.86 g, 10.2 mmol) were dissolved in 15 mL DMF, and NBS (0.66 g, 3.7 mmol) was added in three portions. The mixture was stirred at RT for 5 hrs. The reaction solution was diluted with 50 mL water, and extracted with EtOAc (30 mL*3). The organic phase was washed with 20 mL saturated brine, dried over anhydrous sodium sulfate, and filtered. The filtrate was concentrated, and separated by silica gel column chromatography to afford a pale yellow solid, 0.85 g, yield: 80%. ESI-MS: 279[M$^+$+2].

Step 6: Synthesis of Compound 2-(4-(6-(1-methyl-TH-pyrazol-4-yl)pyrazolo[1,5-a]pyridin-3-yl)phenyl)-N-(5-(1,1,1-trifluoro-2-methylpropan-2-yl)isoxazol-3-yl)acetamide (Compound T-11)

3-bromo-6-(1-methyl-1H-pyrazol-4-yl)pyrazolo[1,5-a]pyridine (86 mg, 0.31 mmol), 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (158 mg, 0.36 mmol), Pd(dppf)Cl$_2$ (15 mg, 0.02 mmol), and Na$_2$CO$_3$ (131 mg, 1.24 mmol) were added in 12 mL DME and 4 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 71 mg, yield: 45%. ESI-MS: 509[M$^+$+1]. $^1$H NMR (400 MHz, DMSO-d$_6$) δ 11.45 (s, 1H), 9.16 (s, 1H), 8.58 (s, 1H), 8.32 (s, 1H), 8.11 (d, J=8.3 Hz, 1H), 7.90 (s, 1H), 7.80-7.64 (m, 4H), 7.43 (d, J=8.2 Hz, 1H), 6.94 (s, 1H), 3.91 (s, 3H), 3.79 (s, 2H), 1.54 (s, 6H).

Example 12 Preparation of 2-(4-(6-(1-methyl-1H-pyrazol-4-yl)pyrazolo[1,5-a]pyrazin-3-yl)phenyl)-N-(5-(1,1,1-trifluoro-2-methylpropan-2-yl)isoxazol-3-yl)acetamide (Compound T-12)

T-12

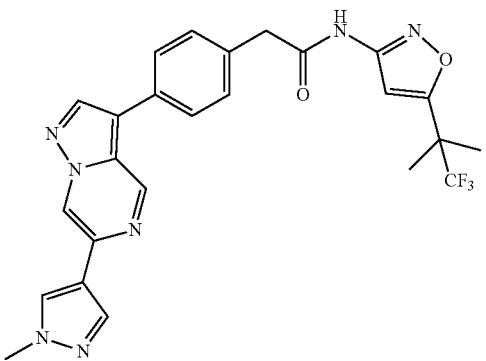

The following synthetic route was used:

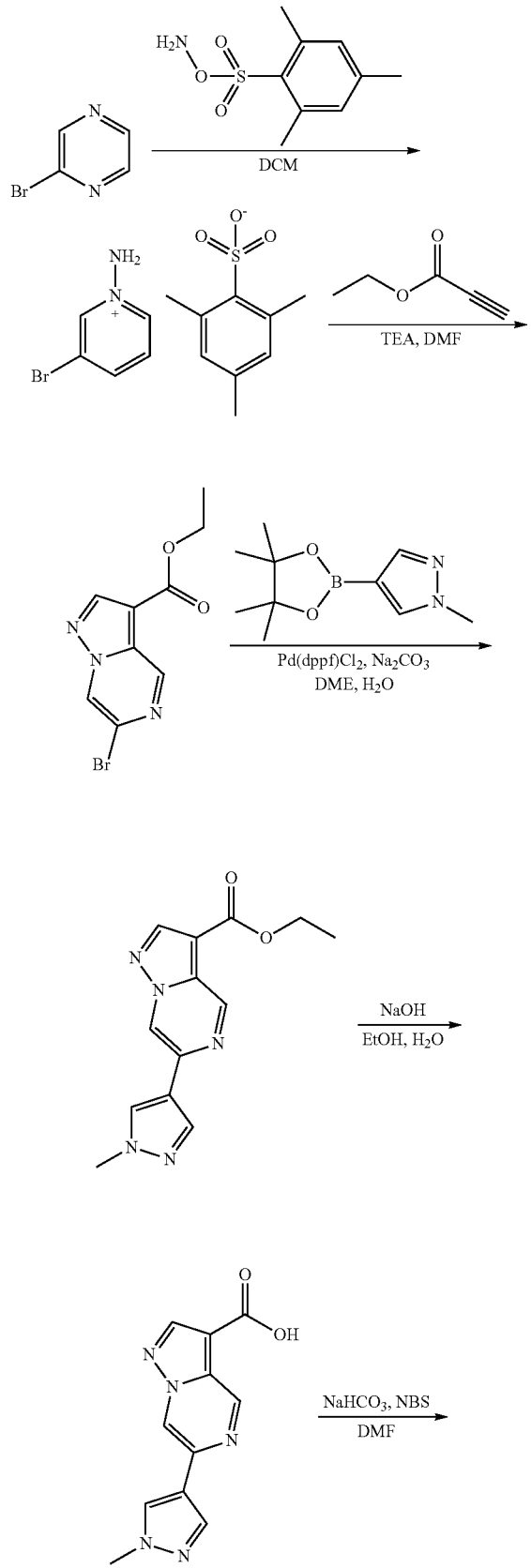

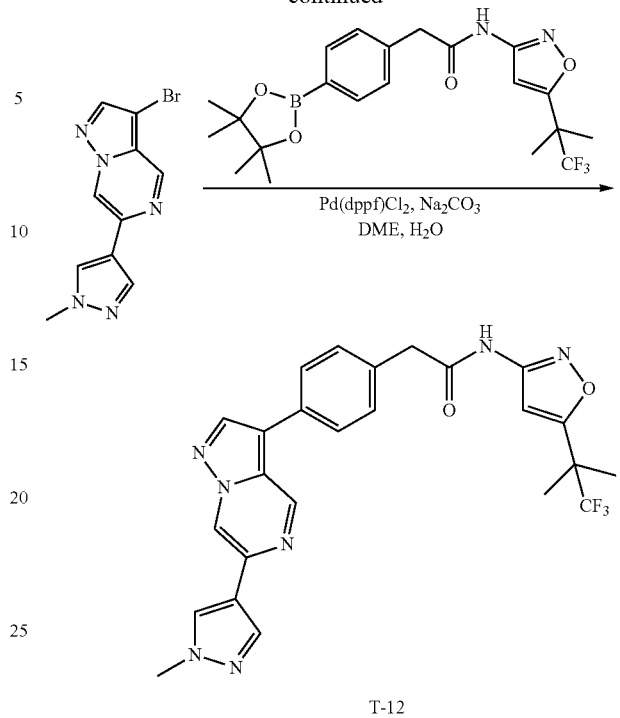

Step 1: Synthesis of Compound 1-amino-3-bromopyrazin-1-ium 2,4,6-trimethylbenzenesulfonate O-(2,4,6-trimethylbenzenesulfonyl)-hydroxylamine (10.8 g, 50 mmol) was dissolved in 100 mL dichloromethane, and 3-bromopyrazine (8.69 g, 55 mmol) was slowly added dropwise under an ice bath. After the addition was completed, the mixture was reacted at RT for 2 hrs, during which a white solid gradually precipitated out. 200 mL methyl tert-butyl ether was added. The mixture was further stirred for 20 min, and then filtered. The filter cake was washed with 100mL methyl tert-butyl ether. The solid was placed into vacuum oven and dried at 55° C. for 4 hrs to obtain a white solid, 15 g, yield: 80%.

Step 2: Synthesis of Compound ethyl 6-bromopyrazolo[1,5-a]pyrazin-3-formate 1-amino-3-bromopyrazin-1-ium 2,4,6-trimethylbenzenesulfonate (15 g, 40 mmol) was dissolved in 60 mL anhydrous DMF and triethyl amine (8.08 g, 80 mmol), and ethyl propiolate (7.8 g, 80 mmol) was slowly added dropwise under an ice bath. After the addition was completed, the ice bath was removed. The mixture was stirred at RT for 48 hrs. The reaction solution was diluted with 200 mL water, and extracted with EtOAc (60 mL*3). The organic phase was washed with 10 mL saturated brine, dried over anhydrous sodium sulfate, and filtered. The filtrate was concentrated, and separated by silica gel column chromatography to afford a pale yellow solid, 1.6 g, yield: 15%. ESI-MS: 272[M$^+$+2].

Step 3: Synthesis of Compound ethyl 6-(1-methyl-1H-pyrazol-4-yl)pyrazolo[1,5-a]pyrazin-3-formate Ethyl 6-bromopyrazolo[1,5-a]pyrazin-3-formate (1.4 g, 5.2 mmol), 1-methyl-4-(4,4,5,5-tetramethyl-1,3,2-dioxaborolan-2-yl)-1H-pyrazole (1.35 g, 6.5 mmol), Pd(dppf)Cl$_2$ (190 mg, 0.26 mmol), and Na$_2$CO$_3$ (1.65 g, 15.6 mmol) were added in 20 mL DME and 5 mL water, and the system was flushed three times with nitrogen. The mixture was heated to 90° C. and reacted overnight. The reaction solution was cooled to room temperature, quenched with 40 ml water, and extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 0.98 g, yield: 70%. ESI-MS: 272[M$^+$+1].

Step 4: Synthesis of Compound 6-(1-methyl-1H-pyrazol-4-yl)pyrazolo[1,5-a]pyrazin-3-formic acid Ethyl 6-(1-methyl-1H-pyrazol-4-yl)pyrazolo[1,5-a]pyrazin-3-formate (0.98 g, 3.6 mmol) was dissolved in 20 mL ethanol and 10 mL water, and sodium hydroxide (0.38 g, 9.5 mmol) was added. The mixture was reacted at 80° C. for 2 hrs. The reaction solution was diluted with 30 mL water, adjusted to a pH of 3-4 with 1N hydrochloric acid, and extracted with EtOAc (30 mL*3). The organic phase was washed with 20 mL saturated brine, dried over anhydrous sodium sulfate, and filtered. The filtrate was concentrated, and separated by silica gel column chromatography to afford a pale yellow solid, 0.82 g, yield: 94%. ESI-MS: 244[M$^+$+1].

Step 5: Synthesis of Compound 3-bromo-6-(1-methyl-1H-pyrazol-4-yl)pyrazolo[1,5-a]pyrazine 6-(1-methyl-1H-pyrazol-4-yl)pyrazolo[1,5-a]pyrazin-3-formic acid (0.82 g, 3.4 mmol) and sodium bicarbonate (0.86 g, 10.2 mmol) were dissolved in 15 mL DMF, and NBS (0.66 g, 3.7 mmol) was added in three portions. The mixture was stirred at RT for 5 hrs. The reaction solution was diluted with 50 mL water, and extracted with EtOAc (30 mL*3). The organic phase was washed with 20 mL saturated brine, dried over anhydrous sodium sulfate, and filtered. The filtrate was concentrated, and separated by silica gel column chromatography to afford a pale yellow solid, 0.68 g, yield: 72%. ESI-MS: 280[M$^+$+2].

Step 6: Synthesis of Compound 2-(4-(6-(1-methyl-1H-pyrazol-4-yl)pyrazolo[1,5-a]pyrazin-3-yl)phenyl)-N-(5-(1,1,1-trifluoro-2-methylpropan-2-yl)isoxazol-3-yl)acetamide (Compound T-12)

3-bromo-6-(1-methyl-1H-pyrazol-4-yl)pyrazolo[1,5-a]pyrazine (86 mg, 0.31 mmol), 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (158 mg, 0.36 mmol), Pd(dppf)Cl$_2$ (15 mg, 0.02 mmol), and Na$_2$CO$_3$ (131 mg, 1.24 mmol) were added in 12 mL DME and 4 mL water, and the system was flushed three times with nitrogen. The mixture was heated to 90° C. and reacted overnight. The reaction solution was cooled to room temperature. 30 mL water was added, and the mixture was extracted with EtOAc (20 mL*3). The organic phase was washed with 10 mL saturated brine, dried over anhydrous sodium sulfate, and filtered. The filtrate was concentrated, and separated by silica gel column chromatography to afford a pale yellow solid, 80 mg, yield: 51%. ESI-MS: 510[M$^+$+1]. $^1$H NMR (400 MHz, DMSO-d$_6$) δ 11.45 (s, 1H), 9.16 (s, 1H), 8.65 (s, 1H), 8.46 (s, 1H), 8.15 (s, 1H), 7.91 (s, 1H), 7.85-7.62 (m, 4H), 6.86 (s, 1H), 3.91 (s, 3H), 3.78 (s, 2H), 1.54 (s, 6H).

Bioactivity Assay

Biological Example 1: Inhibition of Kinase (1) Inhibition of Kinase

Reagents and Materials

Ret wt (Carna, Cat. No. 08-159-10 ug), RET (V804M), Active (Signalchem, Cat. No. R02-12GG), HTRF KinEASE-TK kit (Cisbio, Cat. No. 62TK0PEC), CEP-32496 (MCE, Cat. No. HY-15200), ATP (Sigma, Cat. No. A7699), DMSO (Sigma, Cat. No. D8418-1L), DTT (Sigma, Cat. No. D0632), MgCl$_2$ (Sigma, Cat. No. M1028), 384-well plate (Labcyte, Cat. No. P-05525-BC).

Specific Assay Procedure:

Formulation of compound: The test compounds were dissolved in DMSO to obtain 10 mM stock solutions, which were then serially diluted 3-fold in DMSO to obtain 10 concentrations. At the time of addition, the compound was further diluted 10-fold with buffer.

Ret Wt and RET V804M Kinase Detection:

In 5× kinase buffer A, Ret wt or RET V804M kinase was mixed with different concentrations of compounds prepared by pre-dilution for 10 minutes. Each concentration was tested in duplicate. The corresponding substrate and ATP were added, and reaction was performed at room temperature for 20 minutes (negative and positive controls were provided: the negative control was a blank control, and the positive control was CEP-32496). After completion of the reaction, detection reagents (reagents in the HTRF KinEASE-TK kit) were added. After incubating for 30 minutes at room temperature, enzyme activity in the presence of various concentrations of the compounds of the present disclosure was determined by Envision microplate reader, and inhibitory activity of different concentrations of the compounds on enzyme activity was calculated. The inhibitory activity of different concentrations of the compounds on enzyme activity was fitted by Graphpad 5.0 software, and the IC$_{50}$ value was calculated, wherein A indicates IC$_{50}$ 10 nM, B indicates 10 nM<IC$_{50}$≤50 nM, C indicates 50 nM<IC$_{50}$≤100 nM, and D indicates IC$_{50}$>100 nM.

The compounds disclosed herein were tested in the above assay of inhibition of kinase, and were found to have potent activity against Ret wt (for example, compounds T-2 to T-4, and T-8 have IC$_{50}$ of <0.2 nM) and RET V804M. Results of representative example compounds were summarized in Table 1 below.

TABLE 1

| Example compound | Ret wt IC$_{50}$ (nM) | RET V804M IC$_{50}$ (nM) |
|---|---|---|
| T-1 | >100 | 75.80 |
| T-2 | 0.18 | 0.40 |
| T-3 | 0.13 | 0.21 |
| T-4 | 0.16 | 0.28 |
| T-5 | 0.25 | 0.80 |
| T-6 | 0.45 | 1.04 |
| T-7 | 0.15 | 0.20 |
| T-8 | 0.10 | 0.35 |
| T-9 | 0.24 | 0.48 |
| T-10 | 0.10 | 0.23 |
| T-11 | 0.68 | 0.87 |
| T-12 | 0.31 | 1.12 |

Biological Example 2: Cytotoxicity Assay (2) Cytotoxicity Assay

Inhibitory effect of example compounds on the activity of Ba/F$_3$ KIF5B-RET and Ba/F$_3$ FLT3-ITD cells was detected.

Materials and reagents: fetal bovine serum (FBS) (GIBCO, Cat. No. 10099141), CellTiter-Glo® Luminescent Cell Viability Assay (Promega, Cat #G7572), 96-well clear flat-bottom black-wall plate (Corning®, Cat #3603).

Assay Procedure:
Culture and Seeding of Cells:
1. Cells in the logarithmic growth phase were harvested and counted with a platelet counter. Cell viability was detected by a trypan blue exclusion method, ensuring that cell viability was 90% or more;
2. The cell concentration was adjusted to 3000 cells/well; 90 μl of cell suspension was added to each well of the 96-well plate;
3. The cells in the 96-well plate were incubated overnight under the condition of 37° C., 5% CO$_2$, and 95% humidity.

Dilution and Addition of Compound:
1. 10-fold compound solutions were formulated by 3.16-fold serial dilution starting from a concentration of 10 μM, resulting in 9 concentrations. 10 μL of the compound solutions were added in each well of the 96-well plate seeded with cells in triplicate for each compound concentration;
2. The cells in the 96-well plate added with compounds were further incubated under the condition of 37° C., 5% CO$_2$, and 95% humidity for 72 hrs, and then CTG analysis was carried out.

Plate Reading at the End:
1. CTG reagent was thawed, and the cell plate was equilibrated at room temperature for 30 minutes;
2. An equal volume (10 μL) of CTG solution was added to each well;
3. The cell plate was shaken on an orbital shaker for 5 minutes to lyse the cells;
4. The cell plate was placed at RT for 20 minutes to stabilize the luminescence signal;
5. Luminescence value was read.

Data Processing

Data were analyzed by GraphPad Prism 5.0 software, and fitted by nonlinear S-curve regression to obtain a dose-response curve, from which IC$_{50}$ values were calculated, wherein A indicates IC$_{50}$≤10 nM, B indicates 10 nM<IC$_{50}$≤50 nM, C indicates 50 nM<IC$_{50}$≤100 nM, and D indicates IC$_{50}$>100 nM.

$$\text{cell survival (\%)} = (\text{Lum}_{test\ compound} - \text{Lum}_{culture\ medium\ control})/(\text{Lum}_{cell\ control} - \text{Lum}_{culture\ medium\ control}) \times 100\%.$$

The compounds disclosed herein were tested in the above cytotoxicity assay, and were found to have potent activity against Ba/F$_3$ KIF5B-RET and Ba/F$_3$ FLT3-ITD cell lines. Results of representative example compounds were summarized in Table 2 below.

TABLE 2

| Example Compound | Ba/F3 parental IC$_{50}$ (nM) | Ba/F3 KIF5B-RET IC$_{50}$ (nM) | Ba/F3 KIF5B-RET$^{I304M}$ IC$_{50}$ (nM) | Ba/F3 FLT3-ITD IC$_{50}$ (nM) | Ba/F3 FLT3-ITD$^{D835Y}$ IC$_{50}$ (nM) | Ba/F3 FLT3-ITD$^{F691L}$ IC$_{50}$ (nM) |
|---|---|---|---|---|---|---|
| T-1 | 1088.32 | 534.19 |  | 2.32 |  |  |
| T-2 | 3268.94 | 4.91 | 17.92 | 0.79 | 1.22 | 1.43 |
| T-3 | 8072.9 | 51.16 | 124.99 | 0.20 | 9.08 | 13.47 |
| T-4 |  | 7.17 |  | 0.49 |  |  |
| T-5 | 2270.22 | 2.48 | 5.43 | 0.10 | 1.43 | 1.43 |
| T-6 | 2184.44 | 6.20 | 20.87 | 1.05 | 2.38 | 1.24 |
| T-7 | 1822.09 | 2.30 | 10.83 | 0.19 | 1.15 | 1.15 |
| T-8 |  | 15.42 |  |  |  |  |
| T-9 | >10000 | 60.81 | 559.35 | 0.51 | 10.61 | 15.71 |
| T-10 | 929.76 | 9.98 | 8.15 | <0.1 | 1.83 | 1.02 |
| T-11 | 1399.53 | 15.42 | 3.66 | 0.2 | 1.73 | 1.12 |
| T-12 |  | 9.98 |  |  |  |  |

Biological Example 3: Pharmacokinetic Assay in Rats

Six male Sprague-Dawley rats (7-8 weeks old, and weighing about 210 g) were divided into 2 groups, 3 rats in each group. A single dose of compounds (10 mg/kg orally) was administered intravenously or orally to compare their pharmacokinetics.

The rats were fed with standard feed and water. Fasting was started 16 hours before the assay. The drug was dissolved in PEG400 and dimethyl sulfoxide. Blood was collected from the orbit. The time points for blood collection were 0.083 hours, 0.25 hours, 0.5 hours, 1 hour, 2 hours, 4 hours, 6 hours, 8 hours, 12 hours and 24 hours after administration.

The rats were briefly anesthetized after inhaling diethyl ether, and 300 μL of blood sample was collected from the orbit into a test tube containing 30 μL of 1% heparin salt solution. Before use, the test tube was oven dried overnight at 60° C. After the blood sample was collected at the last time point, the rats were anesthetized with diethyl ether and then sacrificed.

Immediately after the blood sample was collected, the test tube was gently inverted at least 5 times to ensure sufficient mixing, and then placed on ice. The blood sample was centrifuged at 5000 rpm at 4° C. for 5 minutes to separate the plasma from the red blood cells. 100 μL of plasma was aspirated into a clean plastic centrifuge tube with a pipette, and the name of the compound and time point were marked. The plasma was stored at −80° C. before analysis. The concentration of the compound of the present disclosure in plasma was determined by LC-MS/MS. The pharmacokinetic parameters were calculated based on the blood drug concentration of each animal at different time points.

The assay shows that the compounds of the present disclosure have better pharmacokinetic properties in animals, and therefore have better pharmacodynamics and therapeutic effects.

The above is a further detailed description of the present disclosure in conjunction with specific alternative embodiments, and it cannot be assumed that the specific embodiments of the present disclosure are limited to these descriptions. For ordinary artisan in the art to which the present disclosure belongs, without deviating from the concept of the present disclosure, various simple deductions or replacements may be made, which should be regarded as falling within the scope of the present disclosure.

What is claimed is:

1. A compound, or a tautomer, stereoisomer, prodrug, crystal form, pharmaceutically acceptable salt, hydrate or solvate thereof, wherein the compound is of the following formula:

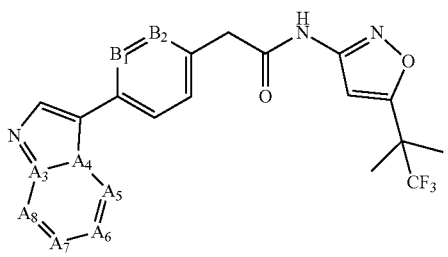

A₃ and A₄ are each independently selected from C atom and N atom, and wherein one C atom and one N atom are included;
A₅ and A₆ are each independently selected from N atom and C atom, which are optionally substituted with R;
A₇ and A₈ are each independently selected from N atom and C atom, which are optionally substituted with R';
wherein each instance of R is each independently selected from H, D, halogen, and —CN;
each instance of R' is each independently selected from H, D, halogen, —CN, and -L₁-R_a;
wherein one of A₇ and A₈ is substituted with -L₁-R_a;
wherein L₁ is selected from bond, O, and NH; R_a is

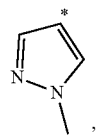

wherein * indicates the location of attachment to L₁;
B₁ and B₂ are each independently selected from CR* and N; and
wherein each instance of R* is each independently selected from H, D, halogen, and —CN.

2. The compound according to claim 1, or a tautomer, stereoisomer, prodrug, crystal form, pharmaceutically acceptable salt, hydrate or solvate thereof, wherein the compound is of the following formula:

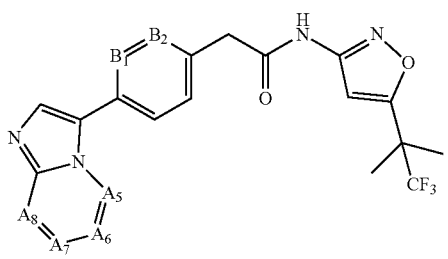

wherein
A₅ and A₆ are each independently selected from N atom and C atom, which are optionally substituted with R;
A₇ and A₈ are each independently selected from N atom and C atom, which are optionally substituted with R';
wherein each instance of R is each independently selected from H, D, halogen, and —CN;
each instance of R' is each independently selected from H, D, halogen, —CN, and -L₁-R_a;
and at least one of A₅, A₆ and A₇ is N, and one of A₇ and A₈ is substituted with -L₁-R_a;
wherein L₁ is selected from bond, O, and NH; R_a is

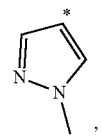

wherein * indicates the location of attachment to L₁;
B₁ and B₂ are each independently selected from CR* and N; and
wherein each instance of R* is each independently selected from H, D, halogen, and —CN.

3. The compound according to claim 1, or a tautomer, stereoisomer, prodrug, crystal form, pharmaceutically acceptable salt, hydrate or solvate thereof, wherein the compound is of the following formula:

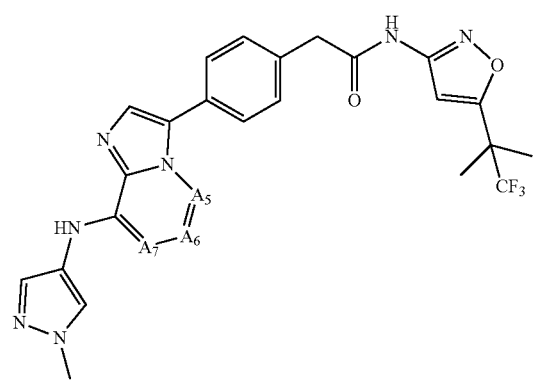

wherein
A₅ and A₆ are each independently selected from N atom and C atom, which are optionally substituted with R;
A₇ is selected from N atom and C atom, which are optionally substituted with R';
and at least one of A₅, A₆ and A₇ is N;
wherein each instance of R is each independently selected from H, D, halogen, and —CN; and
each instance of R' is each independently selected from H, D, halogen, and —CN.

4. The compound according to claim 1, or a tautomer, stereoisomer, prodrug, crystal form, pharmaceutically acceptable salt, hydrate or solvate thereof, wherein the compound is of the following formula:

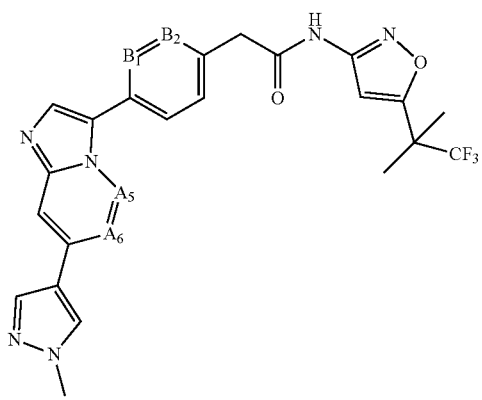

wherein

A₅ and A₆ are each independently selected from N atom and C atom, which are optionally substituted with R, wherein at least one of A₅ and A₆ is N atom;

B₁ and B₂ are each independently selected from CR* and N;

wherein each instance of R is each independently selected from H, D, halogen, and —CN; and each instance of R* is each independently selected from H, D, halogen, and —CN.

5. The compound according to claim 1, or a tautomer, stereoisomer, prodrug, crystal form, pharmaceutically acceptable salt, hydrate or solvate thereof, wherein the compound is of the following formula:

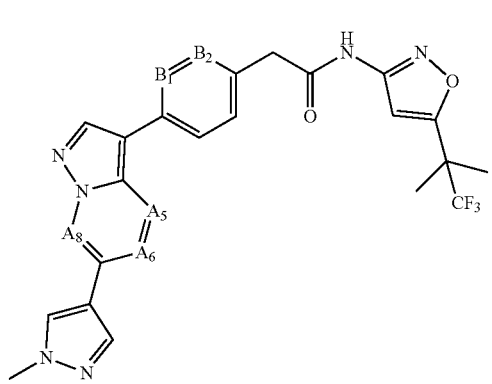

wherein

A₅ and A₆ are each independently selected from N atom and C atom, which are optionally substituted with R;

A₈ is selected from N atom and C atom, which are optionally substituted with R';

B₁ and B₂ are each independently selected from CR* and N;

wherein each instance of R is each independently selected from H, D, halogen, and —CN;

each instance of R* is each independently selected from H, D, halogen, and —CN; and at least one of A₅, A₆ and A₈ is N atom.

6. A compound, or a tautomer, stereoisomer, prodrug, crystal form, pharmaceutically acceptable salt, hydrate or solvate thereof, wherein the compound is selected from:

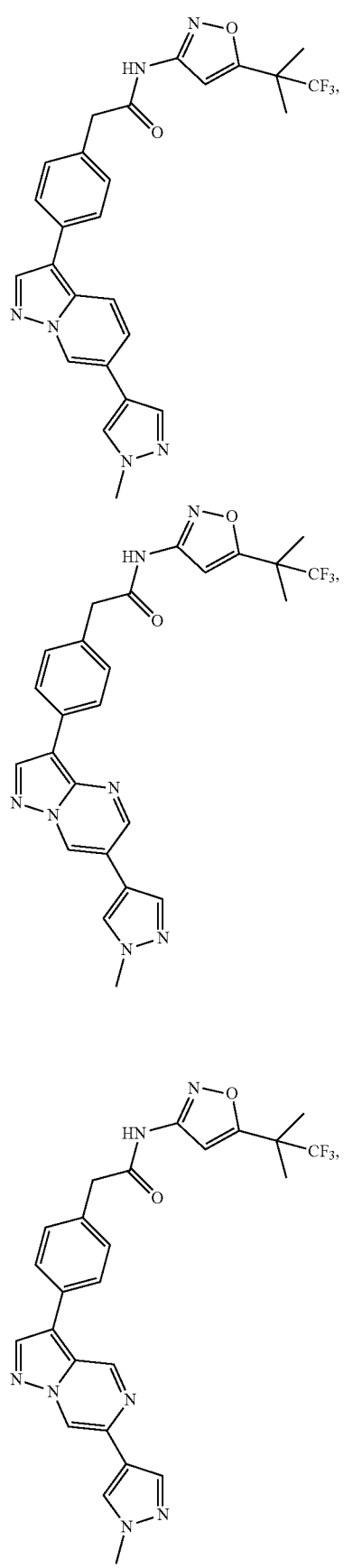

85
-continued
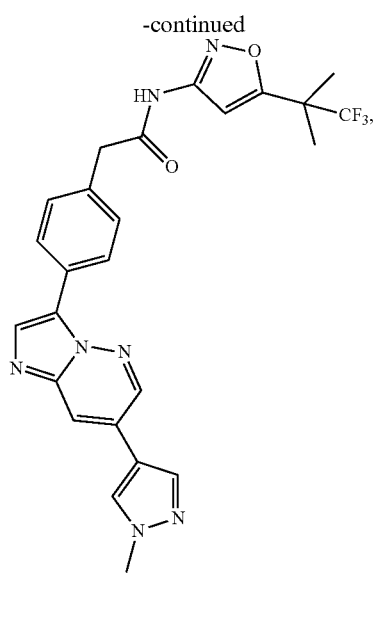
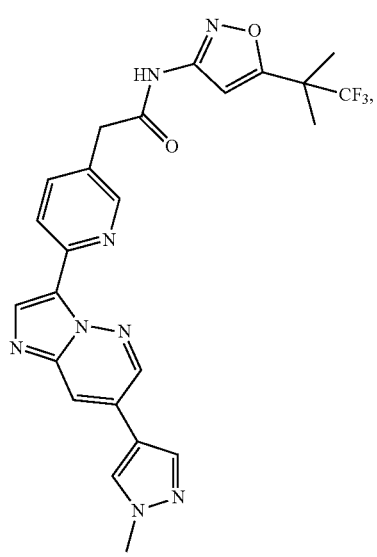
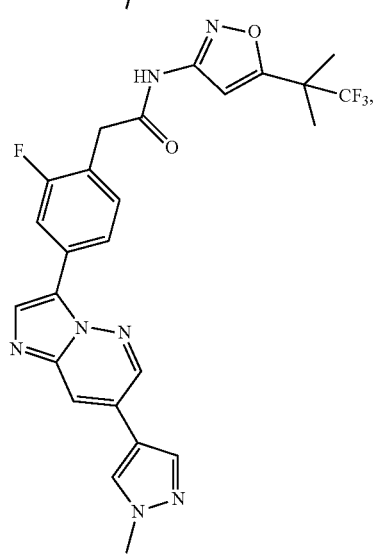
86
-continued
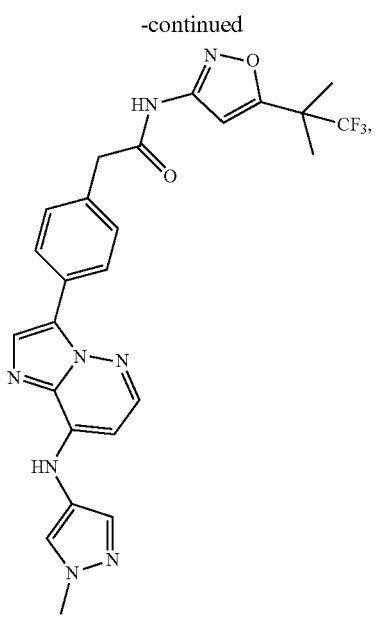
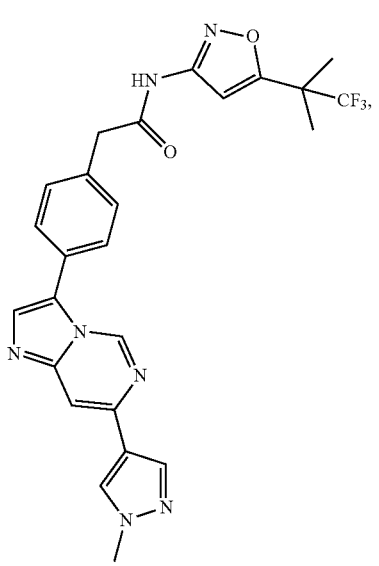
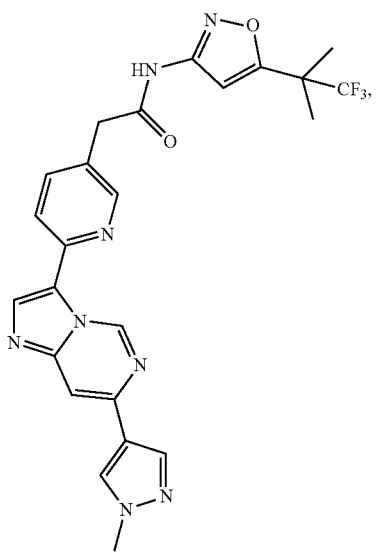

-continued

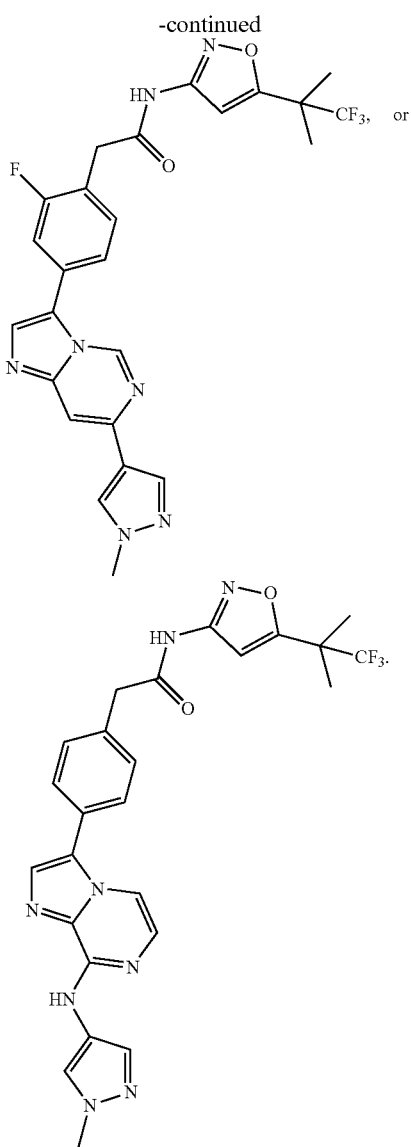

7. A pharmaceutical composition, which comprises a compound of claim 1, or a tautomer, stereoisomer, prodrug, crystal form, pharmaceutically acceptable salt, hydrate or solvate thereof, and pharmaceutically acceptable excipient(s).

8. A method for treating and/or preventing a disease mediated by a protein kinase in a subject, comprising administering to the subject a compound of claim 1, or a tautomer, stereoisomer, prodrug, crystal form, pharmaceutically acceptable salt, hydrate or solvate thereof.

9. The method according to claim 8, wherein the disease mediated by a protein kinase is a disease mediated by one or more kinases selected from the group consisting of wild-types and mutants of RET, KIF5B-RET, CCDC6-RET, Trk, FLT3, c-Kit, PDGFR, and VEGFR kinases.

10. The method according to claim 8, wherein the disease is selected from the group consisting of non-small cell lung cancer, papillary thyroid cancer, glioblastoma multiforme, acute myeloid leukemia, colorectal cancer, large cell neuroendocrine cancer, prostate cancer, colon cancer, acute lymphoblastic leukemia, sarcoma, pediatric glioma, intrahepatic cholangiocarcinoma, hairy cell astrocytoma, low grade glioma, lung adenocarcinoma, salivary gland cancer, secretory breast cancer, fibrosarcoma, nephroma, breast cancer, myelodysplastic syndrome, gastrointestinal stromal tumor, melanoma, seminoma, intracranial germ cell tumor, and mediastinal B-cell lymphoma.

11. The compound according to claim 4, or a tautomer, stereoisomer, prodrug, crystal form, pharmaceutically acceptable salt, hydrate or solvate thereof, wherein both of $B_1$ and $B_2$ are CR*.

12. The compound according to claim 5, or a tautomer, stereoisomer, prodrug, crystal form, pharmaceutically acceptable salt, hydrate or solvate thereof, wherein $A_5$ is N atom.

* * * * *